(12) United States Patent
Noguchi et al.

(10) Patent No.: US 11,173,213 B2
(45) Date of Patent: Nov. 16, 2021

(54) METHOD FOR SELECTIVELY MANUFACTURING ANTIBODY-DRUG CONJUGATE

(71) Applicant: DAIICHI SANKYO COMPANY, LIMITED, Tokyo (JP)

(72) Inventors: Shigeru Noguchi, Tokyo (JP); Ken Sakurai, Tokyo (JP); Daisuke Okajima, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 445 days.

(21) Appl. No.: 15/579,512

(22) PCT Filed: Jun. 28, 2016

(86) PCT No.: PCT/JP2016/069068
§ 371 (c)(1),
(2) Date: Dec. 4, 2017

(87) PCT Pub. No.: WO2017/002776
PCT Pub. Date: Jan. 5, 2017

(65) Prior Publication Data
US 2018/0147292 A1     May 31, 2018

(30) Foreign Application Priority Data

Jun. 29, 2015 (JP) .............................. JP2015-129692

(51) Int. Cl.
| | |
|---|---|
| *A61K 47/68* | (2017.01) |
| *A61K 31/4745* | (2006.01) |
| *A61K 31/40* | (2006.01) |
| *C07K 16/00* | (2006.01) |
| *A61K 39/395* | (2006.01) |
| *A61K 45/00* | (2006.01) |
| *A61P 35/00* | (2006.01) |
| *A61K 31/407* | (2006.01) |
| *C07K 16/32* | (2006.01) |
| *C07K 16/28* | (2006.01) |

(52) U.S. Cl.
CPC .......... *A61K 47/6803* (2017.08); *A61K 31/40* (2013.01); *A61K 31/407* (2013.01); *A61K 31/4745* (2013.01); *A61K 39/395* (2013.01); *A61K 45/00* (2013.01); *A61P 35/00* (2018.01); *C07K 16/00* (2013.01); *A61K 39/3955* (2013.01); *C07K 16/28* (2013.01); *C07K 16/2896* (2013.01); *C07K 16/32* (2013.01)

(58) Field of Classification Search
CPC ............ A61K 47/6803; A61K 47/6805; A61K 47/6807; A61K 47/6809; A61K 47/6811; A61K 47/6813; A61K 47/6815; A61K 47/6817; A61K 47/6819; A61K 47/6821; A61K 47/6823; A61K 47/6825; A61K 47/6827; A61K 47/6829; A61K 47/6831; A61K 47/6833
See application file for complete search history.

(56) References Cited

U.S. PATENT DOCUMENTS

| | | |
|---|---|---|
| 5,480,968 A | 1/1996 | Kraus et al. |
| 5,677,171 A | 10/1997 | Hudziak et al. |
| 5,821,337 A | 10/1998 | Carter et al. |
| 5,834,476 A | 11/1998 | Terasawa et al. |
| 5,837,673 A | 11/1998 | Tsujihara et al. |
| 5,892,043 A | 4/1999 | Tsujihara et al. |
| 5,968,511 A | 10/1999 | Akita et al. |
| 6,214,345 B1 | 4/2001 | Firestone et al. |
| 6,291,671 B1 | 9/2001 | Inoue et al. |
| 6,835,807 B1 | 12/2004 | Susaki et al. |
| 7,041,818 B2 | 5/2006 | Susaki et al. |
| 7,449,184 B2 | 11/2008 | Allison et al. |
| 7,585,491 B2 | 9/2009 | Govindan |
| 7,833,979 B2 | 11/2010 | Sullivan et al. |

(Continued)

FOREIGN PATENT DOCUMENTS

| | | |
|---|---|---|
| CA | 2927832 A1 | 11/2011 |
| CA | 2815154 A1 | 2/2012 |

(Continued)

OTHER PUBLICATIONS

Wiggins et al (Journal of Pharmaceutical Sciences, 2015, vol. 104, pp. 1362-1372) (Year: 2015).*
Zhu et al (Cancer Biology and Therapy, 2007, vol. 6, pp. 1960-1966) (Year: 2007).*
Stefano et al ("Micro-and Mid-Scale Maleimide-Based Conjugation for Cytotoxic Drugs to Antibody Hinge Region Thiols for Tumor Targeting", In: 'Antibody-Drug Conjugates', Methods in Molecular Biology, 2013, vol. 1045, pp. 145-165) (Year: 2013).*

(Continued)

*Primary Examiner* — Karen A. Canella
(74) *Attorney, Agent, or Firm* — Foley & Lardner LLP

(57) ABSTRACT

A method for producing an antibody-drug conjugate composition, comprising: (i) a step of reacting an antibody with a reducing agent in a buffer to reduce interchain disulfides, and (ii) a step of reacting drug linker intermediates with the antibody having thiol groups obtained in the step (i), wherein the reaction temperature in the step (i) is −10° C. to 10° C., and the average number of bound drugs in the produced antibody-drug conjugate composition is 3.5 to 4.5, and the content of antibody-drug conjugates in which four drug linkers are bound to heavy-light interchain thiols, in the produced antibody-drug conjugate composition is 50% or more; and an antibody-drug conjugate composition, wherein the content of antibody-drug conjugates wherein the average number of bound drugs is 3.5 to 4.5, and the content of antibody-drug conjugates in which four drug linkers are bound to heavy-light interchain thiols, is 50% or more.

26 Claims, 17 Drawing Sheets
Specification includes a Sequence Listing.

(56) References Cited

U.S. PATENT DOCUMENTS

| | | |
|---|---|---|
| 7,837,980 B2 | 11/2010 | Alley et al. |
| 7,999,083 B2 | 8/2011 | Govindan et al. |
| 8,226,945 B2 | 7/2012 | Ebens, Jr. et al. |
| 8,268,319 B2 | 9/2012 | Govindan |
| 8,394,607 B2 | 3/2013 | Ebens, Jr. et al. |
| 8,425,912 B2 | 4/2013 | Govindan |
| 8,524,865 B2 | 9/2013 | Ebens, Jr. et al. |
| 8,741,291 B2 | 6/2014 | Bhat et al. |
| 8,802,820 B2 | 8/2014 | Chamberlain et al. |
| 8,907,071 B2 | 12/2014 | Sullivan et al. |
| 8,968,741 B2 | 3/2015 | Ebens et al. |
| 2003/0148931 A1 | 8/2003 | Takahashi et al. |
| 2003/0166513 A1 | 9/2003 | Imura et al. |
| 2004/0185053 A1 | 9/2004 | Govindan |
| 2005/0123536 A1 | 6/2005 | Law et al. |
| 2005/0228007 A1 | 10/2005 | Jagtap et al. |
| 2005/0271671 A1 | 12/2005 | Griffiths |
| 2005/0276812 A1 | 12/2005 | Ebens, Jr. et al. |
| 2006/0018899 A1 | 1/2006 | Kao et al. |
| 2006/0193865 A1 | 8/2006 | Govindan |
| 2007/0071764 A1 | 3/2007 | Sullivan et al. |
| 2008/0050310 A1 | 2/2008 | Ebens, Jr. et al. |
| 2008/0131363 A1 | 6/2008 | Govindan et al. |
| 2008/0161245 A1 | 7/2008 | Kratz et al. |
| 2008/0305044 A1 | 12/2008 | McDonagh et al. |
| 2009/0010945 A1 | 1/2009 | Alley et al. |
| 2009/0274713 A1 | 11/2009 | Chari et al. |
| 2009/0286258 A1 | 11/2009 | Kaur et al. |
| 2009/0291093 A1 | 11/2009 | Govindan |
| 2010/0068181 A1 | 3/2010 | Paliwal et al. |
| 2010/0120816 A1 | 5/2010 | Fontana et al. |
| 2011/0045587 A1 | 2/2011 | Sullivan et al. |
| 2011/0059076 A1 | 3/2011 | Mcdonagh et al. |
| 2011/0070248 A1 | 3/2011 | Ichikawa et al. |
| 2011/0229406 A1 | 9/2011 | Hettmann et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2012/0328634 A1 | 12/2012 | Govindan |
| 2013/0078234 A1* | 3/2013 | Takahashi ............... A61P 35/00 424/131.1 |
| 2013/0089872 A1 | 4/2013 | Nakamura et al. |
| 2013/0123178 A1 | 5/2013 | Dimarchi et al. |
| 2013/0216561 A1 | 8/2013 | Govindan |
| 2014/0004078 A1 | 1/2014 | Govindan |
| 2015/0297748 A1 | 10/2015 | Masuda et al. |
| 2015/0337042 A1* | 11/2015 | Reilly ............... A61K 47/6857 424/183.1 |
| 2015/0352224 A1 | 12/2015 | Naito et al. |
| 2016/0279259 A1 | 9/2016 | Masuda et al. |
| 2016/0287722 A1 | 10/2016 | Govindan |
| 2016/0297890 A1 | 10/2016 | Agatsuma et al. |
| 2016/0333112 A1 | 11/2016 | Naito et al. |
| 2017/0021031 A1 | 1/2017 | Hettmann et al. |
| 2017/0035906 A1 | 2/2017 | Naito et al. |
| 2019/0151328 A1 | 5/2019 | Hettmann et al. |

FOREIGN PATENT DOCUMENTS

| | | | |
|---|---|---|---|
| CA | 2859255 A1 | 6/2013 | |
| CN | 1227499 A | 9/1999 | |
| CN | 1764478 A | 4/2006 | |
| CN | 101023100 A | 8/2007 | |
| CN | 101490087 A | 7/2009 | |
| CN | 102481364 A | 5/2012 | |
| EP | 0 495 432 A1 | 7/1992 | |
| EP | 0 737 686 A1 | 10/1996 | |
| EP | 0 916 348 A1 | 5/1999 | |
| EP | 1 155 702 A1 | 11/2001 | |
| EP | 2 594 589 A1 | 5/2013 | |
| EP | 2 799 452 A1 | 11/2014 | |
| EP | 2 907 824 A1 | 8/2015 | |
| EP | 2 910 573 A1 | 8/2015 | |
| JP | H05-059061 A | 3/1993 | |
| JP | H06-87746 A | 3/1994 | |
| JP | H08-337584 A | 12/1996 | |
| JP | H10-095802 A | 4/1998 | |
| JP | H11-171280 A | 3/1999 | |
| JP | H11-092405 A | 4/1999 | |
| JP | 2002-060351 A | 2/2002 | |
| JP | 2005-511627 A | 4/2005 | |
| JP | 2006-511526 A | 4/2006 | |
| JP | 2007-527872 A | 10/2007 | |
| JP | 2008-500961 A | 1/2008 | |
| JP | 2008-521828 A | 6/2008 | |
| JP | 2009-538629 A | 11/2009 | |
| JP | 2010-513524 A | 4/2010 | |
| JP | 2011-519864 A | 7/2011 | |
| JP | 2011-524001 A | 8/2011 | |
| JP | 2012-509259 A | 4/2012 | |
| JP | 2012-100671 A | 5/2012 | |
| JP | 2013-500253 A | 1/2013 | |
| JP | 2013-534535 A | 9/2013 | |
| JP | 2013-534906 A | 9/2013 | |
| JP | 2017-503784 A | 2/2017 | |
| KR | 1020010052385 A | 6/2001 | |
| KR | 1020110044808 A | 4/2011 | |
| RU | 2404810 C2 | 7/2008 | |
| RU | 2450008 C2 | 7/2010 | |
| TW | I232930 | 5/2005 | |
| TW | 200817434 A | 4/2008 | |
| WO | WO-97/46260 A1 | 12/1997 | |
| WO | WO-00/25825 A1 | 5/2000 | |
| WO | WO-01/00244 A2 | 1/2001 | |
| WO | WO-02/00734 A1 | 1/2002 | |
| WO | WO-03/013602 A1 | 2/2003 | |
| WO | WO 03/015826 A1 | 2/2003 | |
| WO | WO 03/043583 A2 | 5/2003 | |
| WO | WO-03/074566 A2 | 9/2003 | |
| WO | WO-2005/112919 A2 | 12/2005 | |
| WO | WO 2006/065533 A2 | 6/2006 | |
| WO | WO 2006/092230 A2 | 9/2006 | |
| WO | WO-2007/077028 A2 | 7/2007 | |
| WO | WO-2008/100624 A2 | 8/2008 | |
| WO | WO-2008/116219 A2 | 9/2008 | |
| WO | WO-2008/144891 A1 | 12/2008 | |
| WO | WO-2011/011474 A1 | 1/2011 | |
| WO | WO 2011/021397 A1 | 2/2011 | |
| WO | WO-2011/068845 A1 | 6/2011 | |
| WO | WO-2011-109308 A1 | 9/2011 | |
| WO | WO-2011/145744 A1 | 11/2011 | |
| WO | WO-2011/155579 A1 | 12/2011 | |
| WO | WO-2011-157741 A2 | 12/2011 | |
| WO | WO-2012/019024 A2 | 2/2012 | |
| WO | WO-2012/047724 A1 | 4/2012 | |
| WO | WO-2012/064733 A2 | 5/2012 | |
| WO | WO-2012/147713 A1 | 11/2012 | |
| WO | WO-2013/068946 A2 | 5/2013 | |
| WO | WO-2013/077458 A1 | 5/2013 | |
| WO | WO-2013093809 A1 * | 6/2013 | ......... C07K 16/2863 |
| WO | WO 2013/163229 A1 | 10/2013 | |
| WO | WO 2013/188740 A1 | 12/2013 | |
| WO | WO-2014/006124 A1 | 1/2014 | |
| WO | WO-2014/057687 A1 | 4/2014 | |
| WO | WO-2014/061277 A1 | 4/2014 | |
| WO | WO-2014-100762 A1 | 6/2014 | |
| WO | WO-2014/107024 A1 | 7/2014 | |
| WO | WO-2015/098099 A1 | 7/2015 | |
| WO | WO-2015/115091 A1 | 8/2015 | |
| WO | WO-2015/146132 A1 | 10/2015 | |
| WO | WO-2015/155976 A1 | 10/2015 | |
| WO | WO-2015/155998 A1 | 10/2015 | |

OTHER PUBLICATIONS

Alley et al, Antibody-drug conjugates: targeted drug delivery for cancer, Current Opinion in Chemical Biology, 2010, pp. 529-537, vol. 14.

Badescu et al, Bridging Disulfides for Stable and Defined Antibody Drug Conjugates, Bioconjugate Chemistry, 2014, pp. 1124-1136.

(56) References Cited

OTHER PUBLICATIONS

Damle, Nitin K, Tumour-targeted chemotherapy with immunoconjugates of calicheamicin, Expert Opinion on Biological Therapy, 2004, pp. 1445-1452, vol. 4.
Ducry et al, Antibody-Drug Conjugates: Linking Cytotoxic Payloads to Monoclonal Antibodies, Bioconjugate Chemistry, 2010, pp. 5-13.
Nakada et al, Novel antibody drug conjugates containing exatecan derivative-based cytotoxic payloads, Bioorganic & Medicinal Chemistry Letters, 2016, pp. 1542-1545, vol. 26.
Ogitani et al, Wide application of a novel topoisomerase I inhibitor-based drug conjugation technology, Bioorganic & Medicinal Chemistry Letters, pp. 5069-5072, vol. 26.
Abdollahpour-Alitappeh et al, Evaluation of Factors Influencing Antibody Reduction for Development of Antibody Drug Conjugates, Iranian Biomedical Journal, 2017, vol. 21, No. 4, pp. 270-274.
Extended European Search Report dated Jan. 15, 2019 in corresponding application No. 16817884.6.
Acchione et al., "Impact of linker and conjugation chemistry on antigen binding, Fc receptor binding and thermal stability of model antibody-drug conjugates," mAbs, vol. 4, No. 3, May/Jun. 2012, pp. 362-372.
Adams et al., "Humanization of a recombinant monoclonal antibody to produce a therapeutic HER dimerization inhibitor, pertuzumab," Cancer Immunol. Immunother., vol. 55, 2006, pp. 717-727.
Alimandi et al., "Cooperative signaling of ErbB3 and ErbB2 in neoplastic transformation and human mammary carcinomas," Oncogene 10:1813-1821 (1995).
"Appeal for Reposition against Resolution 12260 of Feb. 21 of 2018, by which a patent of invention is granted," filed in Colombian Patent Office in connection with Colombian Patent Application No. NC2016/0000187.
Barginear et al., "Trastuzumab-DM1: A Review of the Novel Immuno-Conjugate for HER2-Overexpressing Breast Cancer," The Open Breast Cancer Journal, vol. 1, 2009, pp. 25-30.
Barok et al., "Trastuzumab-DM1 is highly effective in preclinical models of HER2-positive gastric cancer," Cancer Letters, vol. 306, 2011, pp. 172-179.
Baselga et al., "Phase II Study of Weekly Intravenous Recombinant Humanized Anti-p185$^{HER2}$ Monoclonal Antibody in Patients with HER2/neu-Overexpressing Metastatic Breast Cancer," Journal of Clinical Oncology, vol. 14, No. 3, Mar. 1996, pp. 737-744.
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Beck, Alain, "The Next Generation of Antibody-drug Conjugates Comes of Age," Discovery Medicine, vol. 10, No. 53, Oct. 16, 2010 (8 pages).
Behrens et al., "Methods for site-specific drug conjugation to antibodies," mAbs, vol. 6, No. 1, 2014, pp. 46-53.
Bouchard et al., "Antibody-drug conjugates-A new wave of cancer drugs," Bioorganic & Medicinal Chemistry Letters, vol. 24, 2014, pp. 5357-5363.
Burke et al., "Design, Synthesis, and Biological Evaluation of Antibody-Drug Conjugates Comprised of Potent Camptothecin Analogues", Bioconjugate Chemistry, vol. 20, No. 6, 2009, pp. 1242-1250.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.
Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Canadian Intellectual Property Office, "Interview Summary," issued in connection with Canadian Patent Application No. 2,885,800, dated Mar. 28, 2017.

Canadian Intellectual Property Office, "Office Action," issued in connection with Canadian Patent Application No. 2,939,802, dated Apr. 13, 2018.
Cardillo et al., "Humanized Anti-Trop-2 IgG—SN-38 Conjugate for Effective Treatment of Diverse Epithelial Cancers: Preclinical Studies in Human Cancer Xenograft Models and Monkeys," Clinical Cancer Research, vol. 17, No. 10, Mar. 3, 2011, pp. 3157-3169.
Coussens et al., "Tyrosine Kinase Receptor with Extensive Homology to EGF Receptor Shares Chromosomal Location with *neu* Oncogene," Science, vol. 230, Dec. 1985, pp. 1132-1139.
De Jager et al., "DX-8951f: Summary of Phase I Clinical Trials," Ann. N.Y. Acad. Sci., vol. 922, 2000, pp. 260-273.
Defazio et al., "Expression of c-*erb*B Receptors, Heregulin and Oestrogen Receptor in Human Breast Cell Lines," Int. J. Cancer 87:487-498 (2000).
Di Fiore et al., "*erb*B-2 Is a Potent Oncogene When Overexpressed in NIH/3T3 Cells," Science, vol. 237, Jul. 1987, pp. 178-182.
Dosio et al., "Antibody-targeted leucinostatin A", Journal of Controlled Release, No. 32, (1994), pp. 37-44.
El Sewedy et al., "Cloning of the Murine *Trop2* Gene: Conservation of a $PIP_2$-Binding Sequence in the Cytoplasmic Domain of Trop-2," Int. J. Cancer 75(2):324-330 (1998).
Esteva et al., "A Phase II Study of Intravenous Exatecan Mesylate (DX-8951f) Administered Daily for 5 Days Every 3 Weeks to Patients with Metastatic Breast Carcinoma," American Cancer Society, 2003, 900-907.
European Patent Office, "Communication with extended European Search Report," issued in connection with European Patent Application No. 13845596.9, dated May 6, 2016.
European Patent Office, "Communication with extended European Search Report," issued in connection with European Patent Application No. 13847461.4, dated May 13, 2016.
European Search Report issued in corresponding application No. 14874745.4 dated May 10, 2017.
Extended European Search Report issued in European Patent Application No. 15743738.5 dated Aug. 9, 2017.
Extended European Search Report issued in European Patent Application No. 15776810.2 dated Aug. 11, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/*neu* Gene Product," Cancer Research, vol. 50, Mar. 1, 1990, pp. 1550-1558.
Fong et al., "High expression of TROP2 correlates with poor prognosis in pancreatic cancer," Br. J. Cancer 99(8): 1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-*erb*B-Related Gene, c-*erb*B-2, on Human Chromosome 17 and Its Amplification in a Gastric Cancer Cell Line," Molecular and Cellular Biology, vol. 6, No. 3, Mar. 1986, pp. 955-958.
Gomez-Monterrey et al., "Design, Synthesis, and Cytotoxic Evaluation of Acyl Derivatives of 3-Aminonaphtho[2,3-*b*]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," The EMBO Journal, vol. 16, No. 7, 1997, pp. 1647-1655.
Gravalos et al., "HER2 in gastric cancer: a new prognostic factor and a novel therapeutic target," Annals of Oncology, vol. 19, 2008, pp. 1523-1529.
Hardwick et al., "Immunohistochemical detection of p53 and c-*erb*B-2 in oesophageal carcinoma; no correlation with prognosis," European Journal of Surgical Oncology, vol. 23, 1997, pp. 30-35.
Hudis, M.D., Clifford A., "Trastuzumab—Mechanism of Action and Use in Clinical Practice," The New England Journal of Medicine, vol. 357, No. 1, 2007, pp. 39-51.

(56) References Cited

OTHER PUBLICATIONS

Hudziak et al., "Increased expression of the putative growth factor receptor p185HER2 causes transformation and tumorigenesis of NIH 3T3 cells," Proc. Natl. Acad. Sci. USA, vol. 84, Oct. 1987, pp. 7159-7163.

Inoue et al., "CM-Dextran-Polyalcohol-Camptothecin Conjugate: DE-310 with A Novel Carrier System and Its Preclinical Data," Polymer Drugs in the Clinical Stage, 2003, pp. 145-153.

Intellectual Property Office of Singapore, "Invitation to Respond to Written Opinion," issued in connection with Singaporean Patent Application No. 11201502887W, dated Apr. 22, 2016.

International Search Report for PCT/JP2014/006421 dated Mar. 17, 2015.

International Search Report issued in International Patent Application No. PCT/JP2015/000355 dated Apr. 21, 2015.

International Search Report with English language translation and Written Opinion issued in International Application No. PCT/JP2015/002020 dated Jul. 20, 2015.

International Search Report with English language translation and Written Opinion issued in International Application No. PCT/JP2017/036215 dated Nov. 21, 2017.

International Searching Authority, "International Search Report," issued in connection with International Patent Application No. PCT/JP2013/006069, dated Dec. 17, 2013.

International Searching Authority, "International Search Report," issued in connection with International Patent Application No. PCT/JP2013/006178, dated Dec. 17, 2013.

Japanese Patent Office, "Decision to Grant a Patent," in connection with Japanese Patent Application No. 2016-166850, dated Oct. 18, 2016.

Japanese Patent Office, "Decision to Grant Patent," issued in connection with Japanese Patent Application No. 2016-117096, dated Jul. 4, 2017.

Japanese Patent Office, "Notification of Reasons for Refusal," in connection with Japanese Patent Application No. 2016-540705, dated Dec. 6, 2016.

Joto et al., "DX-8951F, A Water-Soluble Camptothecin Analog, Exhibits Potent Antitumor Activity Against a Human Lung Cancer Cell Line and its SN-38-Resistant Variant," Int. J. Cancer, vol. 72, 1997, pp. 680-686.

Kamath et al., "Challenges and advances in the assessment of the disposition of antibody-drug conjugates," Biopharmaceutics & Drug Disposition, 2015, 9 pages.

Kaptain et al., "Her-2/neu and Breast Cancer," Diagnostic Molecular Pathology, vol. 10, No. 3, 2001, pp. 139-152.

Karunagaran et al., "ErbB-2 is a common auxiliary subunit of NDF and EGF receptors: implications for breast cancer," The EMBO Journal, vol. 15, No. 2, 1996, pp. 254-264.

Korkaya et al., "HER2 regulates the mammary stem/progenitor cell population driving tumorigenesis and invasion," Oncogene, vol. 27, 2008, pp. 6120-6130.

Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993).

Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989).

Kumazawa et al., "Antitumor activity of DX-8951f: a new camptothecin derivative," Exp. Opin. Invest. Drugs 7(4):625-632 (1998).

Kumazawa et al., "DE-310, a novel macromolecular carrier system for the camptothecin analog DX-8951f: Potent antitumor activities in various murine tumor models," Cancer Sci., vol. 95, No. 2, Feb. 2004, pp. 168-175.

Kumazawa et al., "Potent and broad antitumor effects of DX-8951f, a water-soluble camptothecin derivative, against various human tumors xenografted in nude mice," Cancer Chemother. Pharmacol., vol. 42, 1998, pp. 210-220.

Linnenbach et al., "Sequence investigation of the major gastrointestinal tumor-associated antigen gene family, GA733," Proc. Natl. Acad. Sci. 86(1):27-31 (Jan. 1989).

Lipinski et al., "Human trophoblast cell-surface antigens defined by monoclonal antibodies," Proc. Natl. Acad. Sci. 78(8):5147-5150 (Aug. 1981).

Loo et al., "Development of an Fc-Enhanced Anti-B7-H3 Monoclonal Antibody with Potent Antitumor Activity," Clinical Cancer Research, vol. 18, No. 4, Jul. 15, 2012, pp. 3834-3845.

Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.

McDonagh et al., "Engineered antibody-drug conjugates with defined sites and stoichiometries of drug attachment," Protein Engineering, Design & Selection, 2006, 19(7):299-307.

Mitsui et al., "A New Water-soluble Camptothecin Derivative, DX-8951f, Exhibits Potent Antitumor Activity against Human Tumors in vitro and in vivo," Jpn. J. Cancer Res, vol. 86, Aug. 1995, pp. 776-782.

Mühlmann et al., "TROP2 expression as prognostic marker for gastric carcinoma," J. Clin. Pathol. 62(2):152-158 (2009).

Naidu et al., "Expression of c-erbB3 protein in primary breast carcinomas," British Journal of Cancer 78(10): 1385-1390 (1998).

Ning et al., "TROP2 expression and its correlation with tumor proliferation and angiogenesis in human gliomas," Neurol. Sci. 34(10):1745-1750 (2013).

Ochi et al., "A possible mechanism for the long-lasting antitumor effect of the macromolecular conjugate DE-310: mediation by cellular uptake and drug release of its active camptothecin analog DX-8951," Cancer Chemother Pharmacol, vol. 55, 2005, pp. 323-332.

Office Action with Search Report dated Aug. 29, 2017, in RU 2015113767.

Oguma et al., "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry," Biomedical Chromatography, vol. 19, 2005, pp. 19-26.

Ohmachi et al., "Clinical Significance of TROP2 Expression in Colorectal Cancer," Clin. Cancer Res. 12(10):3057-3063 (May 15, 2006).

Opposition dated May 9, 2017, against CO NC2016/0000187, with partial English translation.

Plowman et al., "Molecular cloning and expression of an additional epidermal growth factor receptor-related gene," Proc. Natl. Acad. Sci. USA 87:4905-4909 (Jul. 1990).

Ripani et al., "Human Trop-2 is a Tumor-Associated Calcium Signal Transducer," Int. J. Cancer 76(5):671-676 (1998).

Rowinsky et al., "Preclinical and Clinical Development of Exatecan (DX-8951f), A Hexacyclic Camptothecin Analog," Camptothecins in Cancer Therapy, Chapter 14, 2005, pp. 317-341.

Russian Office Action dated Oct. 11, 2018 in corresponding application No. 2016123597.

Senter et al., "The discovery and development of brentuximab vedotin for use in relapsed Hodgkin lymphoma and systemic anaplastic large cell lymphoma," Nature Biotechnology 30(7):631-637 (Jul. 2012).

Shen et al., "Conjugation site modulates the in vivo stability and therapeutic activity of antibody-drug conjugates," Nature Biotechnology, vol. 30, Jan. 22, 2012, pp. 184-189.

Shiose et al., "Systematic Research of Peptide Spacers Controlling Drug Release from Macromolecular Prodrug System, Carboxymethyldextran Polyalcohol-Peptide-Drug Conjugates," Bioconjugate Chem., vol. 20, 2009, pp. 60-70.

Shiose et al., "Relationship between Drug Release of DE-310, Macromolecular Prodrug of DX-8951f, and Cathepsins Activity in Several Tumors," Biol. Pharm. Bull., 2007, 30(12):2365-2370.

Sliwkowski et al., "Coexpression of erbB2 and erbB3 Proteins Reconstitutes a High Affinity Receptor for Heregulin." The Journal of Biological Chemistry, vol. 269, No. 20, 1994, pp. 14661-14665.

(56) References Cited

OTHER PUBLICATIONS

Sliwkowski et al., "Nonclinical Studies Addressing the Mechanism of Action of Trastuzumab (Herceptin)," Seminars in Oncology, vol. 26, No. 4, Suppl. 12, Aug. 1999, No. 60-70.
Soepenberg et al., "Liquid chromatographic assays for DE-310, a novel camptothecin analog, and two major enzymatic products in human matrices," Journal of Chromatography B, vol. 799, 2004, pp. 15-22.
Soepenberg et al., "Phase I and Pharmacokinetic Study of DE-310 in Patients with Advanced Solid Tumors," Clinical Cancer Research, vol. 11, Jan. 15, 2005, pp. 703-711.
Taiwanese Office Action dated Jul. 30, 2018 in corresponding application No. 104111534.
Taiwanese Office Action dated May 15, 2017 in corresponding application No. 102136742.
Taiwanese Patent Office, "Allowance", issued in connection with Taiwanese Patent Application No. 104103127,dated Apr. 11, 2018.
Takiguchi et al., "Antitumor Effect of DX-8951, a Novel Camptothecin Analog, on Human Pancreatic Tumor Cells and Their CPT-11-resistant Variants Cultured in vitro and Xenografted in Nude Mice," Jpn. J. Cancer Res., vol. 88, Aug. 1997, pp. 760-769.
The Korean Intellectual Property Office, "Notice of Grounds for Rejection," issued in connection with Korean Patent Application No. 10-2016-7015961, dated May 1, 2018.
The State Intellectual Property Office of People's Republic of China, "The First Office Action," issued in connection with Chinese Patent Application No. 201380053256.2, dated Nov. 1, 2016.
Vogel et al., "Efficacy and Safety of Trastuzumab as a Single Agent in First-Line Treatment of HER2-Overexpressing Metastatic Breast Cancer," Journal of Clinical Oncology, vol. 20, No. 3, Feb. 1, 2002, pp. 719-726.
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-l-inhibitor exatecan (DX-8951), in patients with operable solid tumors," Investigational New Drugs, vol. 23, 2005, pp. 339-347.
Yano et al., "Comparison of HER2 gene amplification assessed by fluorescence in situ hybridization and HER2 protein expression assessed by immunohistochemistry in gastric cancer," Oncology Reports, vol. 15, 2006, pp. 65-71.
English Translation of Office Action dated Jul. 16, 2020 for corresponding Taiwanese Patent Application No. 105120426.
Australian Intellectual Property Office, "Examination Report No. 2 for Standard Patent Application," Australian Patent Application No. 2014371934, dated Sep. 13, 2019.
Chinese Office Action dated Nov. 8, 2019 for corresponding Application No. 201580019138.9—4 pages.
Chinese Office Action issued to corresponding App. No. 201480071134.0—dated Aug. 20, 2019 (5 pages).
Extended European Search Report dated Feb. 4, 2020 for corresponding European Patent Application No. 19206764.3.
Final Office Action issued in U.S. Appl. No. 15/221,851 dated Nov. 13, 2017.
I. Sullivan, et al."Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
Indian Office Action issued in the corresponding Indian Patent Application Ser. No. 201647013640, dated Jul. 19, 2019.
International Search Report and Written Opinion for correspondence Application No. PCT/JP2018/007152 dated Apr. 24, 2018.

K. Yonesaka, et al., "Anti-HER3 monoclonal antibody patritumab sensitizes refractory non-small cell lung cancer to the epidermal growth factor receptor inhibitor erlotinib",Oncogene vol. 35, pp. 878-886, 2016 (10 pages.
Kang et al., Engineering multivalent antibodies to target heregulin-induced HER3 signaling in breast cancer cells, mAbs, 2013, vol. 64, No. 1, pp. 15-29.
Kawakami et al—"The anti-HER3 antibody patritumab abrogates cetuximab resistance mediated by heregulin in colorectal cancer cells", Oncotarget, vol. 5, No. 23, Dec.-May 2014, 11847-11856—10 pages.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
N.V. Sergina, et al. "Escape from HER-family tyrosine kinase inhibitor therapy by the kinase-inactive HER3", Nature, vol. 445, pp. 437-441, 2007 (6 pages).
Non-Final Office Action issued in U.S. Appl. No. 14/436,458 dated Jul. 19, 2016.
Non-Final Office Action issued in U.S. Appl. No. 14/435,114 dated Jul. 21, 2016.
Non-Final Office Action issued in U.S. Appl. No. 15/180,203 dated Jul. 25, 2016.
Non-Final Office Action issued in U.S. Appl. No. 15/187,179 dated Oct. 21, 2016.
Non-Final Office Action issued in U.S. Appl. No. 15/221,851 dated Jul. 7, 2017.
Non-Final Office Action issued in U.S. Appl. No. 15/821,697 dated Apr. 5, 2019.
Non-Final Office Action issued in U.S. Appl. No. 15/821,662 dated Jan. 17, 2018.
Notice of Allowance issued in U.S. Appl. No. 15/221,851 dated Jun. 13, 2018.
Notice of Allowance issued in U.S. Appl. No. 15/821,662 dated Nov. 2, 2018.
Office Action dated Jun. 9, 2020 for corresponding Japanese Patent Application No. 2017-526351.
Opposition dated May 3, 2017, against corresponding Colombian Patent Application No. NC2016/0000187.
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Russian Office Action dated Mar. 5, 2019 in corresponding application No. 2016143351.
Sievers et al., Antibody-Drug Conjugates in Cancer Therapy, Annual Review of Medicine, 2013, vol. 64, No. 1, pp. 15-29 (18 pages).
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Notice of Allowance issued in U.S. Appl. No. 15/187,179 dated May 18, 2017.
Notice of Allowance issued in U.S. Appl. No. 15/187,179 dated Aug. 25, 2017.
Examination Report dated Sep. 30, 2020 for corresponding European Patent Application No. 16817884.6.
Katherine Cumnock et al: "Trisulfide Modification Impacts the Reduction Step in Antibody-Drug Conjugation Process", Bioconjugate Chemistry, vol. 24, No. 7, Jul. 17, 2013, pp. 1154-1160.

* cited by examiner

[Figure 1]

SEQ ID NO: 1: Nucleotide sequence of humanized anti-TROP2 antibody heavy chain (hTINA1-H1)
atgaaacacctgtggttcttcctcctgctggtggcagctcccagatgggtgctgagccaggtgcagctggtg
cagtctggcgccgaagtgaagaaaccaggcgccagcgtgaaggtgtcctgcaaggccagcggctacacctttt
accaccgccggcatgcagtgggtgcgccaggctcctggacagggcctggaatggatgggctggatcaacacc
cacagcggcgtgcccaaatacgccgaggacttcaagggcagagtgaccatcagcgccgacaccagcacctcc
acagcctacctgcagctgagcagcctgaagtccgaggacaccgccgtgtactactgcgccagaagcggcttc
ggcagcagctactggtacttcgacgtgtggggccagggcaccctcgtgaccgtcagctcagcctccaccaag
ggcccaagcgtcttccccctggcaccctcctccaagagcacctctggcggcacagccgccctgggctgcctg
gtcaaggactacttccccgaacccgtgaccgtgagctggaactcaggcgccctgaccagcggcgtgcacacc
ttccccgctgtcctgcagtcctcaggactctactccctcagcagcgtggtgaccgtgccctccagcagcttg
ggcacccagacctacatctgcaacgtgaatcacaagcccagcaacaccaaggtggacaagagagttgagccc
aaatcttgtgacaaaactcacacatgcccaccctgcccagcacctgaactcctgggggaccctcagtcttc
ctcttccccccaaaacccaaggacacccctcatgatctcccggacccctgaggtcacatgcgtggtggtggac
gtgagccacgaagaccctgaggtcaagttcaactggtacgtggacggcgtggaggtgcataatgccaagaca
aagccccgggaggagcagtacaacagcacgtaccgggtggtcagcgtcctcaccgtcctgcaccaggactgg
ctgaatggcaaggagtacaagtgcaaggtctccaacaaagccctcccagcccccatcgagaaaaccatctcc
aaagccaaaggccagccccgggaaccacaggtgtacaccctgcccccatcccgggaggagatgaccaagaac
caggtcagcctgacctgcctggtcaaaggcttctatcccagcgacatcgccgtggagtgggagagcaatggc
cagcccgagaacaactacaagaccaccctcccgtgctggactccgacggctccttcttcctctacagcaag
ctcaccgtggacaagagcaggtggcagcagggcaacgtcttctcatgctccgtgatgcatgaggctctgcac
aaccactacacccagaagagcctctccctgtctccggcaaa
Signal sequence (1-57), variable region (58-420), constant region (421-1410)

SEQ ID NO: 2: Amino acid sequence of humanized anti-TROP2 antibody heavy chain (hTINA1-H1)
MKHLWFFLLLVAAPRWVLSQVQLVQSGAEVKKPGASVKVSCKASGYTFTTAGMQWVRQAPGQGLEWMGWINT
HSGVPKYAEDFKGRVTISADTSTSTAYLQLSSLKSEDTAVYYCARSGFGSSYWYFDVWGQGTLVTVSSASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK
Signal sequence (1-19), variable region (20-140), constant region (141-470)

[Figure 2]

SEQ ID NO: 3: Nucleotide sequence of humanized anti-TROP2 antibody light chain (hTINA1-L1)

atggtgctgcagacccaggtgttcatctccctgctgctgtggatctccggcgcgtacggcgacatccagatg
acccagagccctagcagcctgagcgccagcgtgggcgacagagtgaccatcacatgcaaggccagccaggac
gtgtccacagccgtggcctggtatcagcagaagcctggcaaggcccccaagctgctgatctacagcgccagc
taccggtacaccggcgtgcccagcagatttctggcagcggctccggcaccgacttcaccctgacaatcagc
agcctgcagcccgaggacttcgccgtgtactactgccagcagcactacatcacccccctgacctttggccag
ggcaccaagctggaaatcaagcgtacggtggccgcccctccgtgttcatcttcccccctccgacgagcag
ctgaagtccggcaccgcctccgtggtgtgcctgctgaataacttctacccagagaggccaaggtgcagtgg
aaggtggacaacgccctgcagtccgggaactcccaggagagcgtgaccgagcaggacagcaaggacagcacc
tacagcctgagcagcaccctgaccctgagcaaagccgactacgagaagcacaaggtgtacgcctgcgaggtg
acccaccagggcctgagctcccccgtcaccaagagcttcaacagggggagtgt Signal sequence (1-60), variable region (61-387), constant region (388-702)

SEQ ID NO: 4: Amino acid sequence of humanized anti-TROP2 antibody light chain (hTINA1-L1)

MVLQTQVFISLLLWISGAYGDIQMTQSPSSLSASVGDRVTITCKASQDVSTAVAWYQQKPGKAPKLLIYSAS
YRYTGVPSRFSGSGSGTDFTLTISSLQPEDFAVYYCQQHYITPLTFGQGTKLEIKRTVAAPSVFIFPPSDEQ
LKSGTASVVCLLNNFYPREAKVQWKVDNALQSGNSQESVTEQDSKDSTYSLSSTLTLSKADYEKHKVYACEV
THQGLSSPVTKSFNRGEC

Signal sequence (1-20), variable region (21-129), constant region (130-234)

[Figure 3]

SEQ ID NO: 11: Nucleotide sequence of humanized anti-CD98 antibody heavy chain (hM23-H1)
atgaaacacctgtggttcttcctcctgctggtggcagctcccagatgggtgctgagccaggtgcagctggtg
cagtctggcgccgaagtgaagaaaccaggcgccagcgtgaaggtgtcctgcaaggccagcggctacgccttc
agcaactacctgatcgagtgggtgcgccaggcccctggacagggactggaatggatgggcgtgatcaaccct
ggcagcggcgtgaccaactacaacgagaagttcaagggcagagtgaccatcaccgccgacaccagcacctcc
accgcctacatggaactgagcagcctgcggagcgaggacaccgccgtgtactattgtgccagagccgaggct
tggtttgcctactggggccagggaaccctcgtgaccgtcagctcagcctccaccaagggcccaagcgtcttc
cccctggcacccctcctccaagagcacctctggcggcacagccgccctgggctgcctggtcaaggactacttc
cccgaacccgtgaccgtgagctggaactcaggcgccctgaccagcggcgtgcacaccttccccgctgtcctg
cagtcctcaggactctactccctcagcagcgtggtgaccgtgccctccagcagcttgggcacccagacctac
atctgcaacgtgaatcacaagcccagcaacaccaaggtggacaagagagttgagcccaaatcttgtgacaaa
actcacacatgcccaccctgcccagcacctgaactcctggggggaccctcagtcttcctcttccccccaaaa
cccaaggacaccctcatgatctcccggacccctgaggtcacatgcgtggtggtggacgtgagccacgaagac
cctgaggtcaagttcaactggtacgtggacggcgtggaggtgcataatgccaagacaaagccccgggaggag
cagtacaacagcacgtaccgggtggtcagcgtcctcaccgtcctgcaccaggactggctgaatggcaaggag
tacaagtgcaaggtctccaacaaagccctcccagcccccatcgagaaaaccatctccaaagccaaaggccag
ccccgggaaccacaggtgtacaccctgcccccatcccgggaggagatgaccaagaaccaggtcagcctgacc
tgcctggtcaaaggcttctatcccagcgacatcgccgtggagtgggagagcaatggccagcccgagaacaac
tacaagaccacccctcccgtgctggactccgacggctccttcttcctctacagcaagctcaccgtggacaag
agcaggtggcagcagggcaacgtcttctcatgctccgtgatgcatgaggctctgcacaaccactacacccag
aagagcctctccctgtctccggcaaa
Signal sequence (1-57), variable region (58-405), constant region (406-1395)

SEQ ID NO: 12: Amino acid sequence of humanized anti-CD98 antibody heavy chain (hM23-H1)
MKHLWFFLLLVAAPRWVLSQVQLVQSGAEVKKPGASVKVSCKASGYAFSNYLIEWVRQAPGQGLEWMGVINP
GSGVTNYNEKFKGRVTITADTSTSTAYMELSSLRSEDTAVYYCARAEAWFAYWGQGTLVTVSSASTKGPSVF
PLAPSSKSTSGGTAALGCLVKDYFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK
Signal sequence (1-19), variable region (20-135), constant region (136-465)

[Figure 4]

SEQ ID NO: 13: Nucleotide sequence of humanized anti-CD98 antibody light chain (hM23-L1)

atggtgctgcagacccaggtgttcatctccctgctgctgtggatctccggcgcgtacggcgacatcgtgatg
acccagagccctgacagcctggccgtgtctctgggagagagagccaccatcaactgcaagagcagccagagc
ctgctgtactccagcaaccagaagaactacctggcctggtatcagcagaagcccggccagcctcccaagctg
ctgatctactgggccagcaccagagaaagcggcgtgcccgatagattcagcggcagcggaagcggcaccgac
ttcaccctgacaatcagctccctgcaggccgaggacgtggccgtgtactactgccagcggtactacggctac
ccctggacctttggccagggcaccaaggtggaaatcaagcgtacggtggccgccccctccgtgttcatcttc
ccccctccgacgagcagctgaagtccggcaccgcctccgtggtgtgcctgctgaataacttctaccccaga
gaggccaaggtgcagtggaaggtggacaacgccctgcagtccgggaactcccaggagagcgtgaccgagcag
gacagcaaggacagcacctacagcctgagcagcaccctgaccctgagcaaagccgactacgagaagcacaag
gtgtacgcctgcgaggtgacccaccagggcctgagctcccccgtcaccaagagcttcaacagggggagtgt Signal sequence (1-60), variable region (61-405), constant region (406-720)

SEQ ID NO: 14: Amino acid sequence of humanized anti-CD98 antibody light chain (hM23-L1)

MVLQTQVFISLLLWISGAYGDIVMTQSPDSLAVSLGERATINCKSSQSLLYSSNQKNYLAWYQQKPGQPPKL
LIYWASTRESGVPDRFSGSGSGTDFTLTISSLQAEDVAVYYCQRYYGYPWTFGQGTKVEIKRTVAAPSVFIF
PPSDEQLKSGTASVVCLLNNFYPREAKVQWKVDNALQSGNSQESVTEQDSKDSTYSLSSTLTLSKADYEKHK
VYACEVTHQGLSSPVTKSFNRGEC

Signal sequence (1-20), variable region (21-135), constant region (136-240)

[Figure 5]
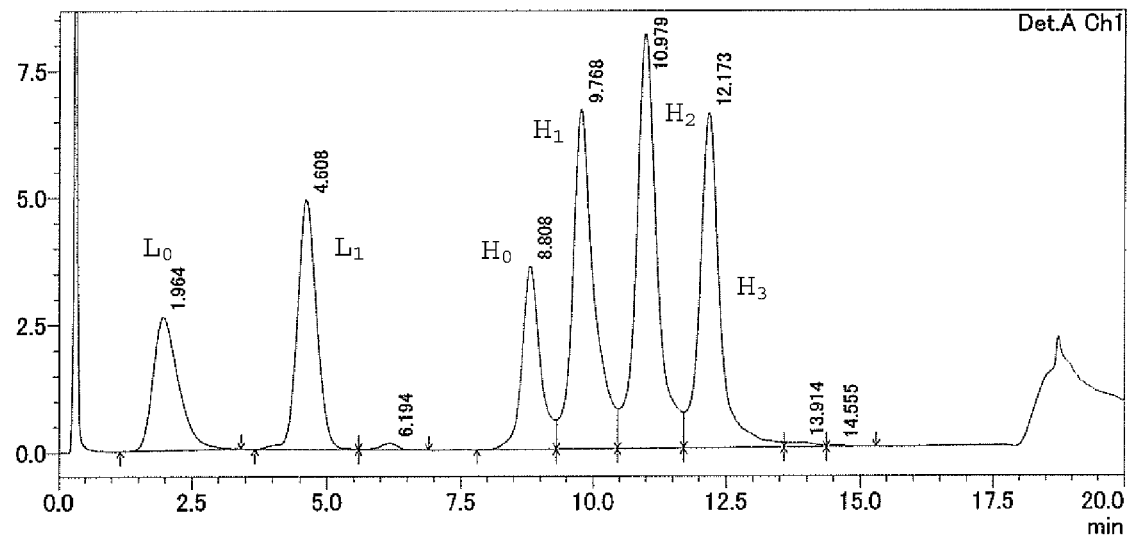
[Figure 6]
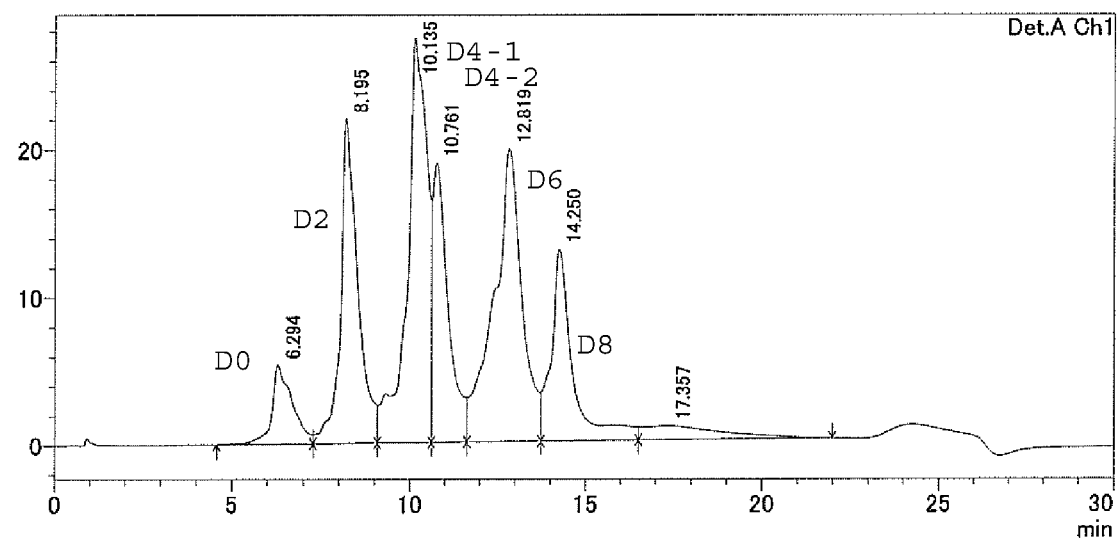

[Figure 7]
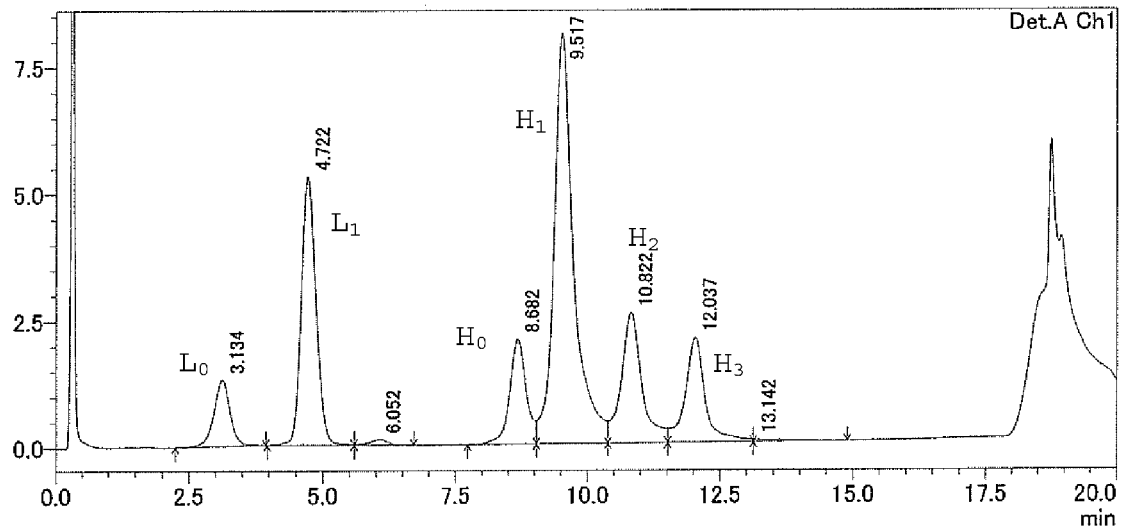
[Figure 8]
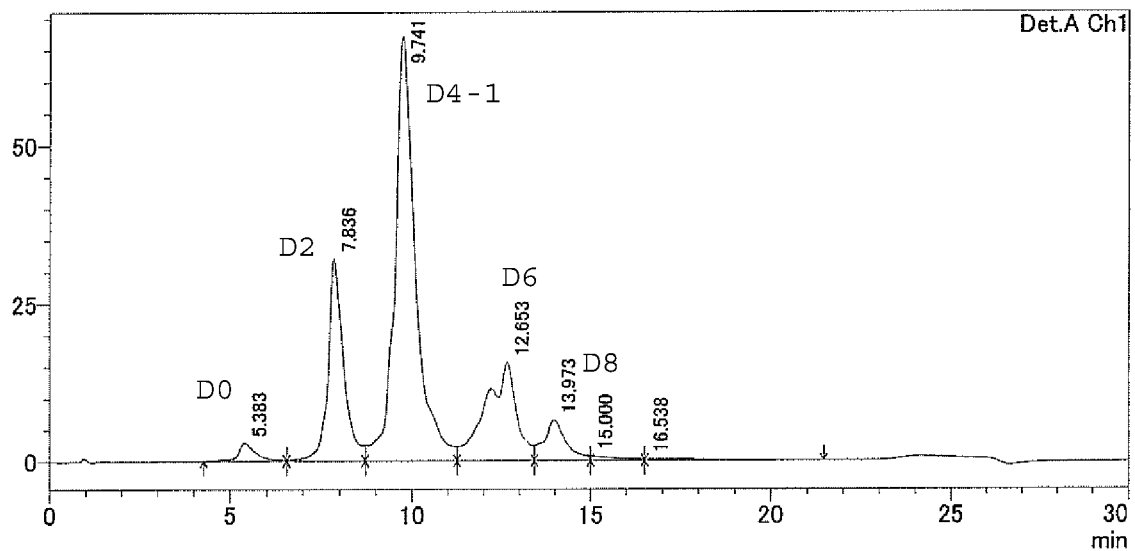

[Figure 9]
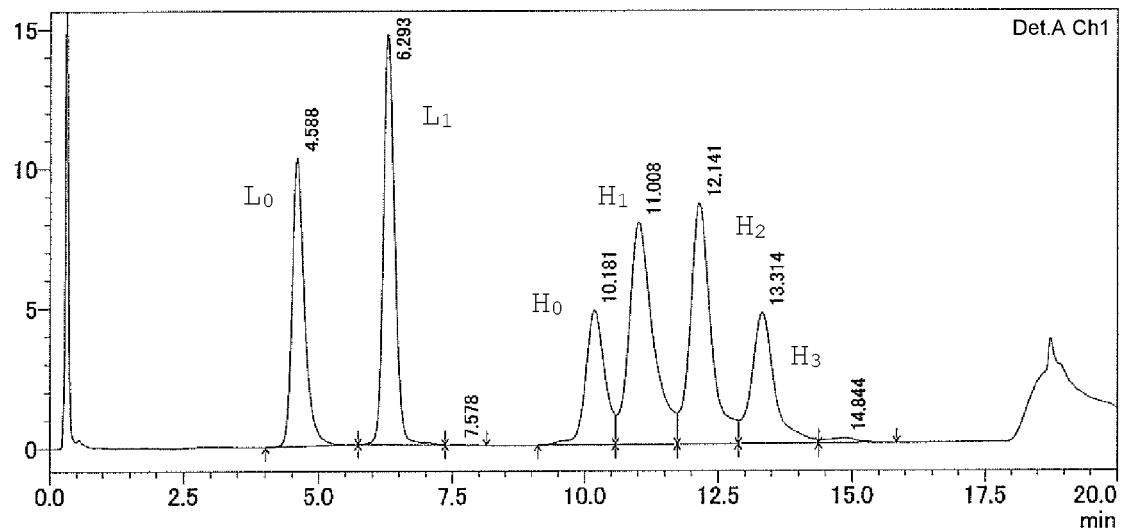
[Figure 10]
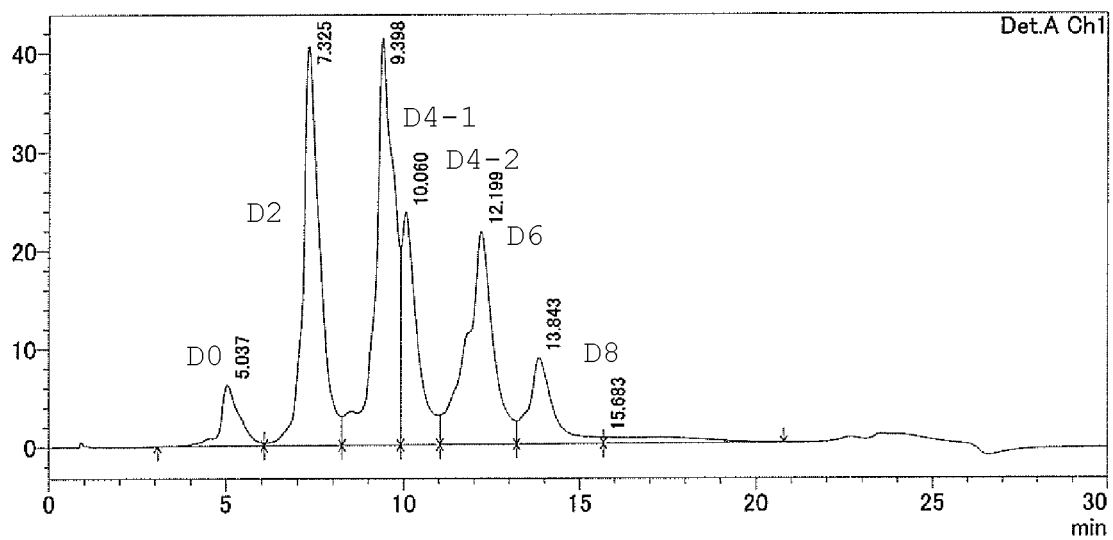

[Figure 11]
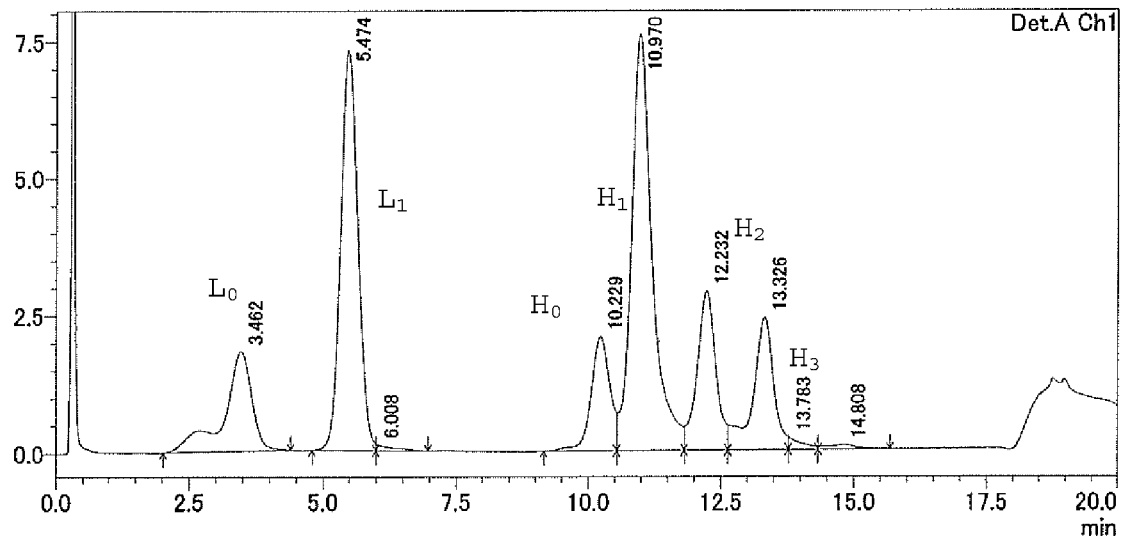
[Figure 12]
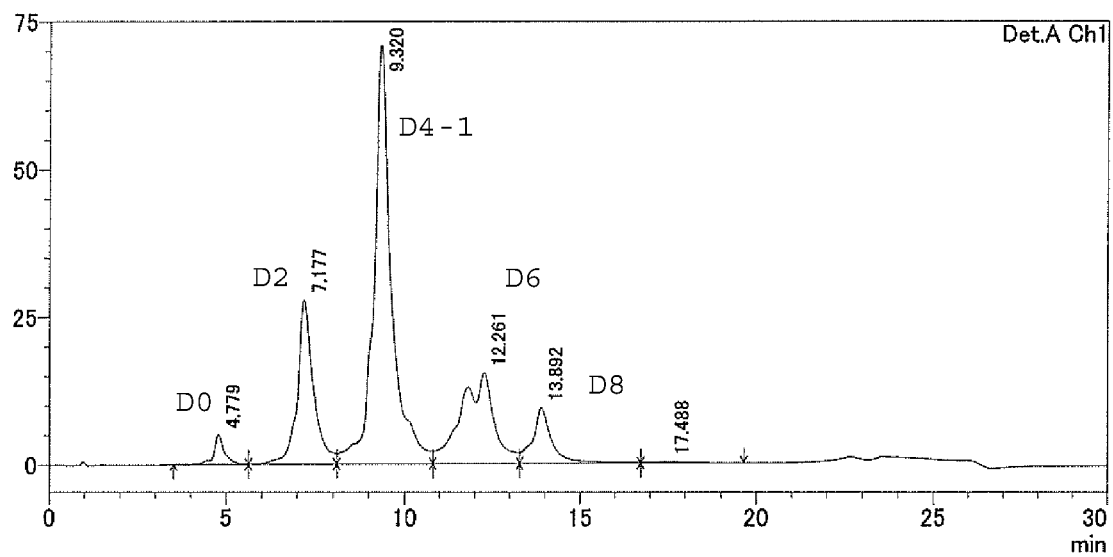

[Figure 13]

SEQ ID NO: 25: Amino acid sequence of humanized anti-B7-H3 antibody heavy chain (M30-H1)

MKHLWFFLLLVAAPRWVLSQVQLVQSGAEVKKPGSSVKVSCKASGYTFTNYVMHWVRQAPGQG
LEWMGYINPYNDDVKYNEKFKGRVTITADESTSTAYMELSSLRSEDTAVYYCARWGYYGSPLY
YFDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRW
QQGNVFSCSVMHEALHNHYTQKSLSLSPGK

Signal sequence (1-19), variable region (20-141), constant region (142-471)

[Figure 14]

SEQ ID NO: 26: Amino acid sequence of humanized anti-B7-H3 antibody light chain (M30-L4)

MVLQTQVFISLLLWISGAYGEIVLTQSPATLSLSPGERATLSCRASSRLIYMHWYQQKPGQAP
RPLIYATSNLASGIPARFSGSGSGTDFTLTISSLEPEDFAVYYCQQWNSNPPTFGQGTKVEIK
RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Signal sequence (1-20), variable region (21-128), constant region (129-233)

[Figure 15]
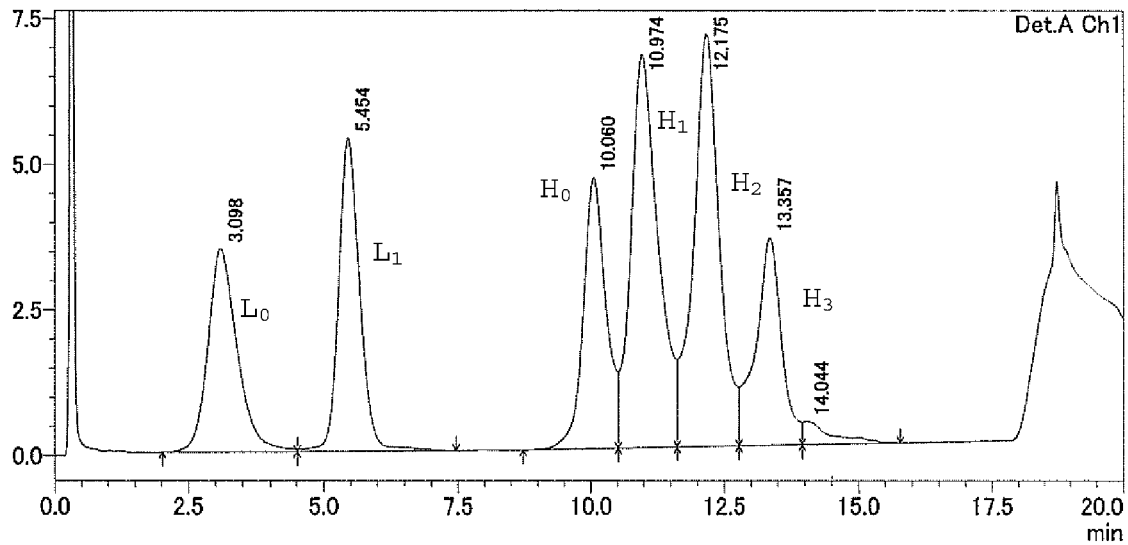
[Figure 16]
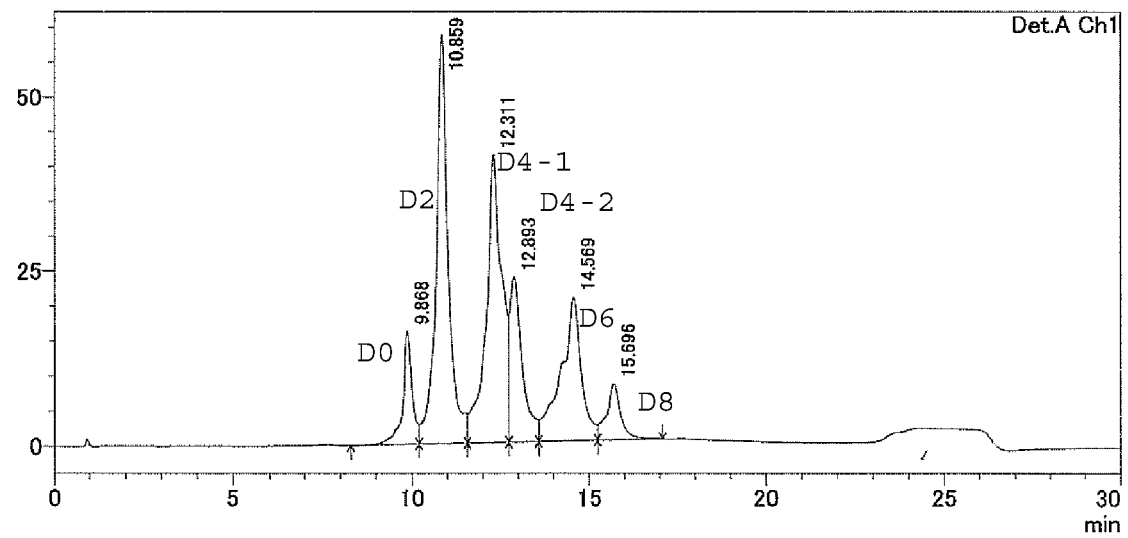

[Figure 17]
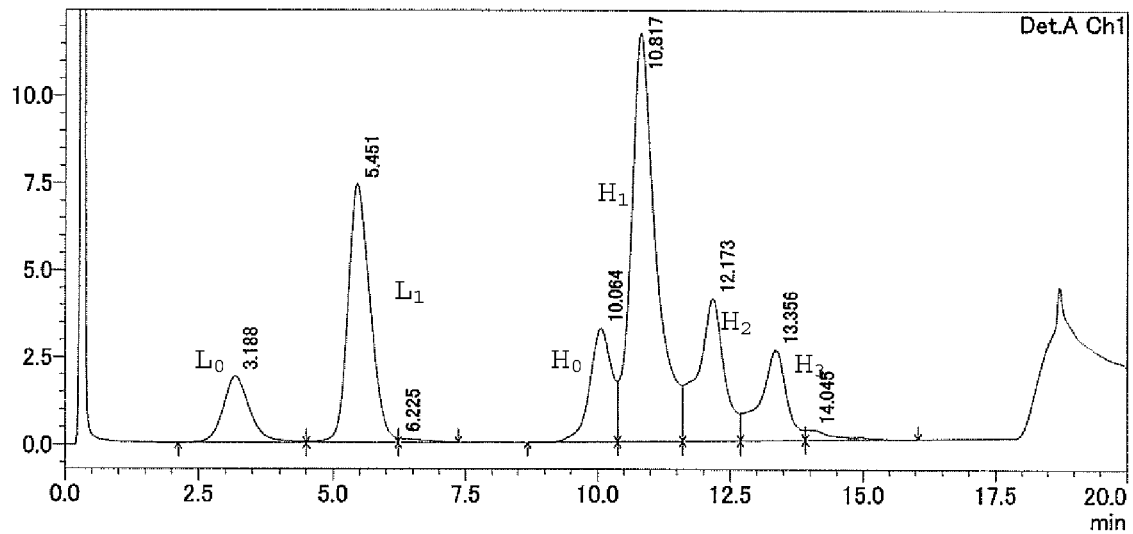
[Figure 18]
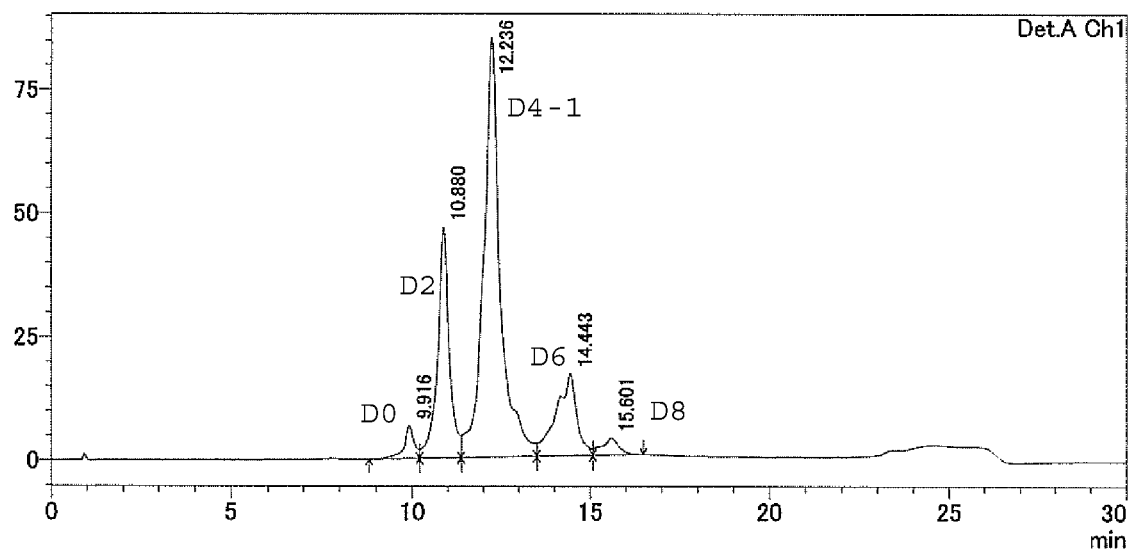

[Figure 19]

SEQ ID NO: 33: Amino acid sequence of humanized anti-HER2 antibody heavy chain

EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYWGQGTLVTVSSASTKGP
SVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQ
KSLSLSPGK

[Figure 20]

SEQ ID NO: 34: Amino acid sequence of humanized anti-HER2 antibody light chain

DIQMTQSPSSLSASVGDRVTITCRASQDVNTAVAWYQQKPGKAPKLLIYSASFLYSGVPSRFS
GSRSGTDFTLTISSLQPEDFATYYCQQHYTTPPTFGQGTKVEIKRTVAAPSVFIFPPSDEQLK
SGTASVVCLLNNFYPREAKVQWKVDNALQSGNSQESVTEQDSKDSTYSLSSTLTLSKADYEKH
KVYACEVTHQGLSSPVTKSFNRGEC

[Figure 21]
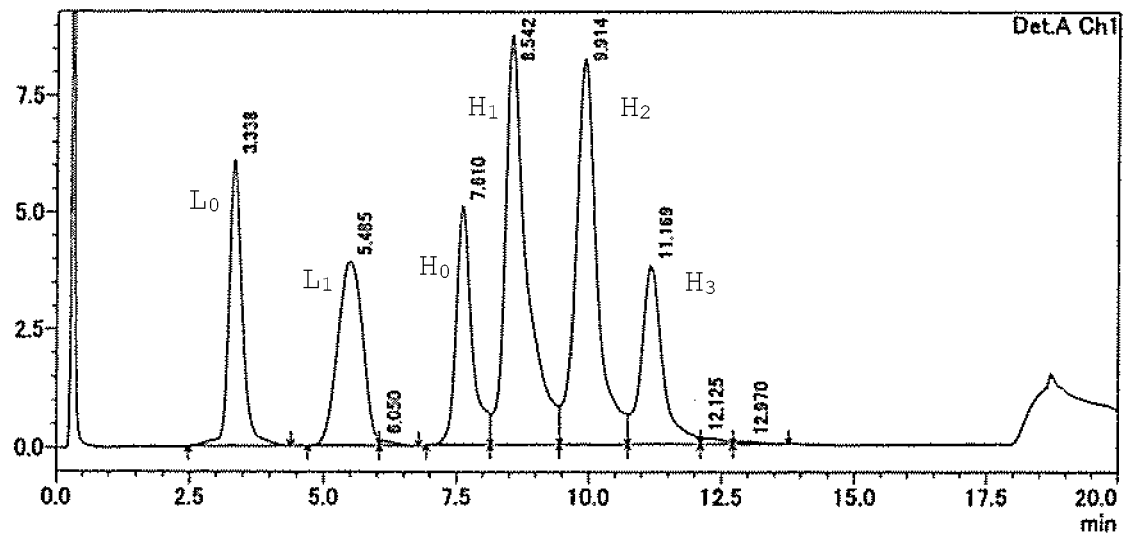
[Figure 22]
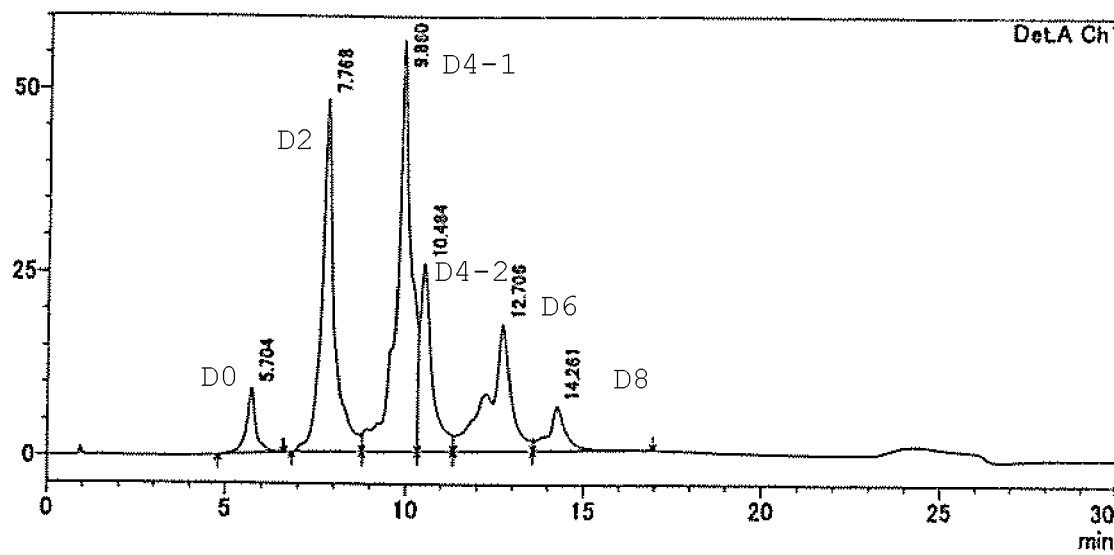

[Figure 23]
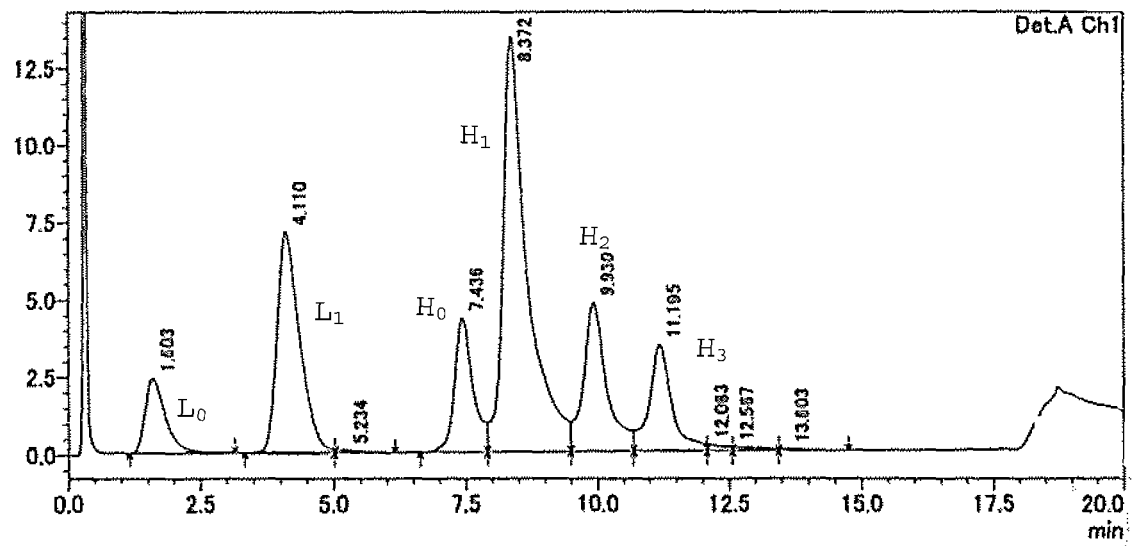
[Figure 24]
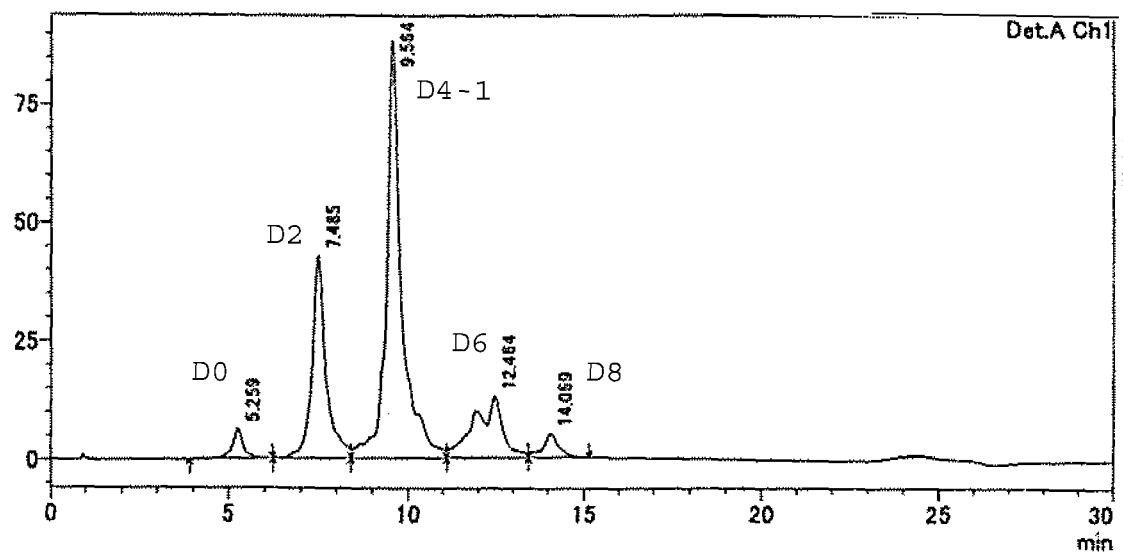

[Figure 25]
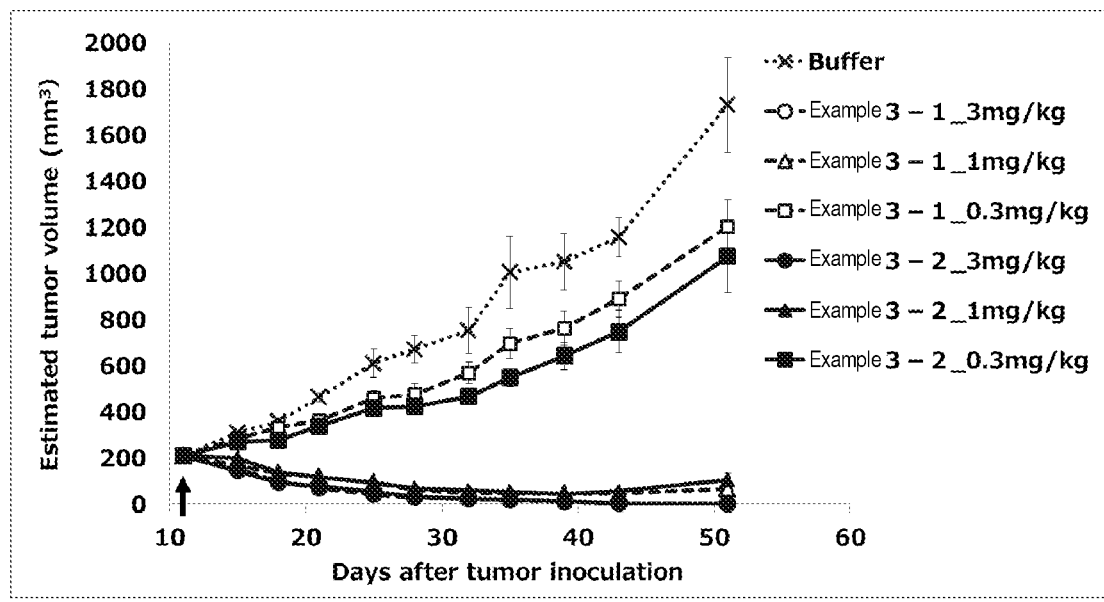

[Formula 19]

D2-1    D2-2

[Formula 20]

D4-1    D4-2    D4-3

[Formula 21]

D6-1    D6-2

Figure 29
[Formula 22]
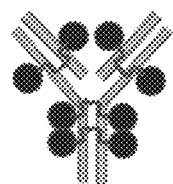
D8
Figure 30
[Formula 28]
$L_0$  $L_1$
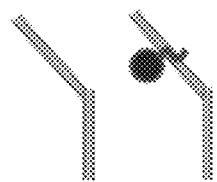
$H_0$  $H_1$  $H_2$  $H_2$  $H_3$

METHOD FOR SELECTIVELY MANUFACTURING ANTIBODY-DRUG CONJUGATE

CROSS-REFERENCE TO RELATED APPLICATIONS

The present application is a U.S. national stage application of International Patent Application No. PCT/JP2016/069068, filed Jun. 28, 2016, which claims the benefit of priority to Japanese Patent Application No. 2015-129692, filed Jun. 29, 2015, the entireties of which are incorporated herein by reference.

SEQUENCE LISTING

The instant application contains a Sequence Listing which has been submitted electronically in ASCII format and is hereby incorporated by reference in its entirety. Said ASCII copy, created on Feb. 25, 2021, is named 122622-0102_SL.txt and is 49,809 bytes in size.

TECHNICAL FIELD

The present invention relates to a method for producing an antibody-drug conjugate composition, in which the number of bound drugs and the binding sites are controlled, and an antibody-drug conjugate composition, in which the number of bound drugs and the binding sites are controlled.

BACKGROUND ART

It can be anticipated that an antibody-drug conjugate (hereinafter also referred to as "ADC") formed by binding a drug having cytotoxicity to an antibody that binds to an antigen capable of being expressed on the surface of a cancer cell, and by internalizing in the cell will be able to selectively deliver the drug to the cancer cell, so that it causes the drug to accumulate in the cancer cell and kill the cancer cell (see Non-Patent Literatures 1 to 3). As such an antibody-drug conjugate, an antibody-drug conjugate formed by binding exatecan that is a camptothecin derivative to an anti-B7-H3 antibody, or the like, is known (Patent Literature 1).

An antibody has four interchain disulfides. These interchain disulfides are approached by solvents more easily than other disulfides, and are easily reduced. Hence, such an interchain disulfide can be used as a binding site to a drug (or a drug linker) in an antibody-drug conjugate. Such an interchain disulfide in an antibody is reduced, and a drug is then allowed to bind to thus generated thiol groups, so as to produce an antibody-drug conjugate in which 2 to 8 drugs bind to a single antibody molecule. Moreover, there is known a method for selectively producing an antibody-drug conjugate having four drug linkers bound to heavy-heavy interchain thiols, wherein the method comprises first completely reducing interchain disulfides in an antibody, re-oxidizing some of the generated interchain thiols to return them to disulfides, and then allowing drugs to bind to the remaining interchain thiols (Patent Literature 2). However, a method for selectively producing an antibody-drug conjugate having four drug linkers bound to heavy-light interchain thiols, is not yet known.

CITATION LIST

Patent Literature

Patent Literature 1: International Publication No. WO2014/057687
Patent Literature 2: International Publication No. WO2005/084390

Non-Patent Literature

Non-Patent Literature 1: Ducry, L., et al., Bioconjugate Chem. (2010) 21, 5-13.
Non-Patent Literature 2: Alley, S. C., et al., Current Opinion in Chemical Biology (2010) 14, 529-537.
Non-Patent Literature 3: Damle N. K., Expert Opin. Biol. Ther. (2004) 4, 1445-1452.

SUMMARY OF INVENTION

Technical Problem

An antibody-drug conjugate, in which 8 drugs are bound to a single antibody molecule, is excellent in terms of antitumor effects, but may cause problems in terms of safety, such as side effects and toxicity, in some cases. Hence, in order to reduce side effects or toxicity, while maintaining therapeutic efficacy, there are cases where an antibody-drug conjugate, in which the average number of bound drugs is less than 8, is used. Such an antibody-drug conjugate, in which the average number of bound drugs is less than 8, can be obtained, for example, by reacting drugs with an antibody, with controlling the amount of drugs per antibody molecule. The reaction products are antibody-drug conjugate compositions, in which the numbers of bound drugs are 2, 4, 6 and 8. Accordingly, there is the possible case where, even if antibody-drug conjugate compositions have the same average number of bound drugs as each other, their therapeutic efficacy and toxicity are different from each other, if they each have a different distribution of the number of bound drugs. That is to say, when the content of antibody-drug conjugates in which the number of bound drugs is 0 and 8 is high in an antibody-drug conjugate composition in which the average number of bound drugs is 4, its therapeutic efficacy may be reduced and strong toxicity may be expressed, when compared with the case where the content of antibody-drug conjugates in which the number of bound drugs is 4 is high. In addition, there is also the possible case where, even if the antibody-drug conjugates have the same number of bound drugs as each other, their therapeutic efficacy and toxicity are different from each other due to a difference in the binding sites of the drugs. Therefore, it has been desired to develop a method for producing an antibody-drug conjugate composition in which the number of bound drugs and the binding sites are controlled in the production of the antibody-drug conjugate composition.

Solution to Problem

As a result of intensive studies directed towards achieving the aforementioned object, the present inventors have found a method for producing an antibody-drug conjugate composition in which the number of bound drugs and the binding sites are controlled, with more simple operations. That is, the inventors have found that an antibody-drug conjugate composition, wherein the content of antibody-drug conjugates in which the average number of bound drugs is 3.5 to 4.5, and four drug linkers are bound to heavy-light interchain thiols, is 50% or more, can be produced by reducing an antibody using a reducing agent in a buffer at a temperature of −10° C. to 10° C., and then reacting drug linker intermediates with the obtained antibody having thiol groups. Moreover, the present inventors have also found that the antibody-drug conjugate composition of the present invention has more excellent safety than antibody-drug conjugate compositions produced by the conventional production method (i.e., an antibody-drug conjugate composition, wherein the content of antibody-drug conjugates in which the average number of bound drugs is 3.5 to 4.5, and four drug linkers are bound to heavy-light interchain thiols, is 35% or less), thereby completing the present invention.

Specifically, the invention of the present application relates to the following (1) to (77):

(1)

A method for producing an antibody-drug conjugate composition, comprising:

(i) a step of reacting an antibody with a reducing agent in a buffer to reduce interchain disulfides; and (ii) a step of reacting drug linker intermediates with the antibody having thiol groups obtained in the step (i), wherein the reaction temperature in the step (i) is −10° C. to 10° C., and the average number of bound drugs in the produced antibody-drug conjugate composition is 3.5 to 4.5, and the content of antibody-drug conjugates in which four drug linkers are bound to heavy-light interchain thiols, in the produced antibody-drug conjugate composition is 50% or more.

(2)

The production method according to the above (1), wherein the average number of bound drugs in the produced antibody-drug conjugate composition is 4.0 to 4.1.

(3)

The production method according to the above (1) or (2), wherein the content of antibody-drug conjugates in which four drug linkers are bound to heavy-light interchain thiols, in the produced antibody-drug conjugate composition is in the range of 50% to 90%.

(4)

The production method according to the above (3), wherein the content of antibody-drug conjugates in which four drug linkers are bound to heavy-light interchain thiols, in the produced antibody-drug conjugate composition is in the range of 50% to 80%.

(5)

The production method according to the above (4), wherein the content of antibody-drug conjugates in which four drug linkers are bound to heavy-light interchain thiols, in the produced antibody-drug conjugate composition is in the range of 50% to 70%.

(6)

The production method according to the above (5), wherein the content of antibody-drug conjugates in which four drug linkers are bound to heavy-light interchain thiols, in the produced antibody-drug conjugate composition is in the range of 50% to 60%.

(7)

The production method according to any one of the above (1) to (6), wherein the content of antibody-drug conjugates in which four drug linkers are bound to heavy-heavy interchain thiols, in the produced antibody-drug conjugate composition is 5% or less.

(8)

The production method according to the above (7), wherein the content of antibody-drug conjugates in which four drug linkers are bound to heavy-heavy interchain thiols, in the produced antibody-drug conjugate composition is 1% or less.

(9)

The production method according to any one of the above (1) to (8), wherein the content of antibody-drug conjugates in which two drug linkers are bound to heavy-heavy interchain thiols and two drug linkers are bound to heavy-light interchain thiols, in the produced antibody-drug conjugate composition is 5% or less.

(10)

The production method according to any one of the above (1) to (8), wherein the content of antibody-drug conjugates in which two drug linkers are bound to heavy-heavy interchain thiols and two drug linkers are bound to heavy-light interchain thiols, in the produced antibody-drug conjugate composition is 1% or less.

(11)

The production method according to any one of the above (1) to (10), wherein the reaction temperature in the step (i) is −5° C. to 5° C.

(12)

The production method according to the above (11), wherein the reaction temperature in the step (i) is −3° C. to 3° C.

(13)

The production method according to the above (12), wherein the reaction temperature in the step (i) is 0° C. to 2° C.

(14)

The production method according to the above (13), wherein the reaction temperature in the step (i) is 0° C. to 1° C.

(15)

The production method according to any one of the above (1) to (14), wherein the reaction temperature in the step (ii) is 0° C. to 2° C.

(16)

The production method according to any one of the above (1) to (15), wherein the reducing agent is used in an amount of 2 to 3 molar equivalents per molecule of the antibody.

(17)

The production method according to any one of the above (1) to (16), wherein the reducing agent is tris(2-carboxyethyl)phosphine or a salt thereof.

(18)

The production method according to the above (17), wherein the salt of tris(2-carboxyethyl)phosphine is tris(2-carboxyethyl)phosphine hydrochloride.

(19)

The production method according to any one of the above (1) to (18), wherein the buffer is a histidine buffer.

(20)

The production method according to any one of the above (1) to (19), wherein the buffer comprises a chelating agent.

(21)

The production method according to the above (20), wherein the chelating agent is ethylenediaminetetraacetic acid.

(22)

The production method according to any one of the above (1) to (21), wherein the antibody is an anti-TROP2 antibody, an anti-CD98 antibody, an anti-B7-H3 antibody, or an anti-HER2 antibody.

(23)

The production method according to the above (22), wherein the antibody is an anti-TROP2 antibody.

(24)

The production method according to the above (22), wherein the antibody is an anti-CD98 antibody.

(25)

The production method according to the above (22), wherein the antibody is an anti-B7-H3 antibody.

(26)

The production method according to the above (22), wherein the antibody is an anti-HER2 antibody.

(27)

The production method according to any one of the above (1) to (26), wherein the drug linker intermediate has an N-substituted maleimidyl group.

(28)

The production method according to the above (27), wherein
the drug linker intermediate is
Formula 1 discloses "GGFG" as SEQ ID NO: 35.

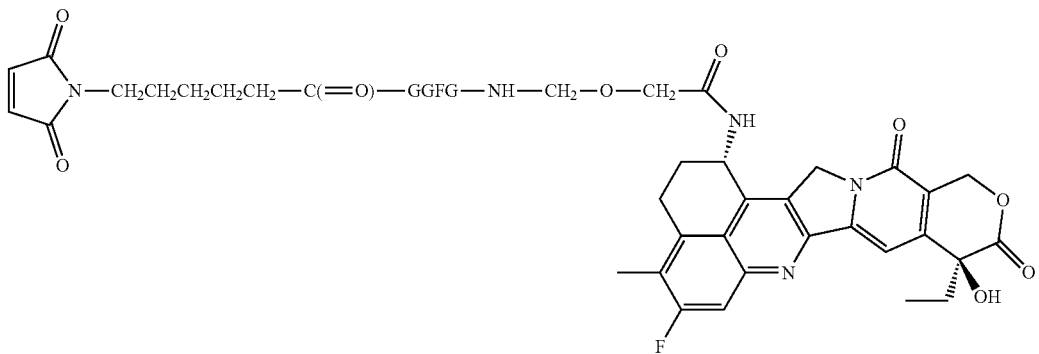

Formula 2 discloses "GGFG" as SEQ ID NO: 35.

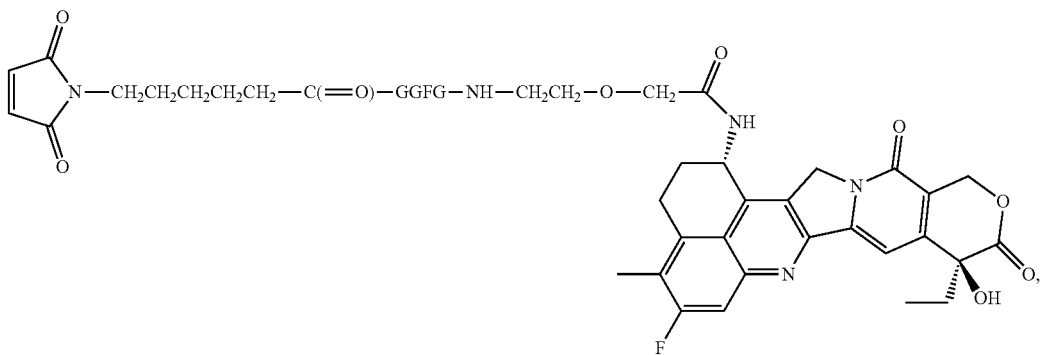

Formula 3 discloses "GGFG" as SEQ ID NO: 35.

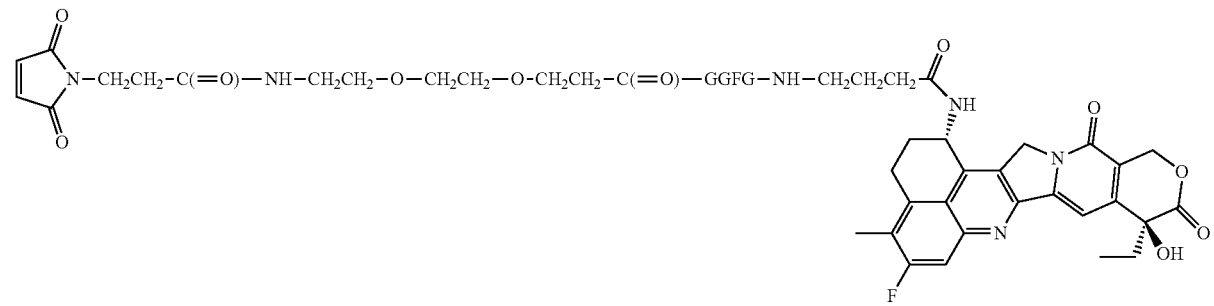

wherein -GGFG- represents a tetrapeptide residue consisting of glycine-glycine-phenylalanine-glycine (SEQ ID NO: 35).

(29)

The production method according to the above (28), wherein the drug linker intermediate is Formula 4 discloses "GGFG" as SEQ ID NO: 35.

lp;2p

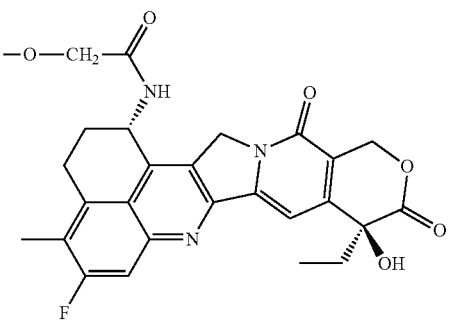

wherein -GGFG- represents a tetrapeptide residue consisting of glycine-glycine-phenylalanine-glycine (SEQ ID NO: 35).

(30)

An antibody-drug conjugate composition produced by the production method according to any one of the above (1) to (29).

(31)

An antibody-drug conjugate composition, wherein the average number of bound drugs is 3.5 to 4.5, and the content of antibody-drug conjugates in which four drug linkers are bound to heavy-light interchain thiols is 50% or more.

(32)

The antibody-drug conjugate composition according to the above (31), wherein the average number of bound drugs is 4.0 to 4.1.

(33)

The antibody-drug conjugate composition according to the above (31) or (32), wherein the content of antibody-drug conjugates in which four drug linkers are bound to heavy-light interchain thiols, is in the range of 50% to 90%.

(34)

The antibody-drug conjugate composition according to the above (33), wherein the content of antibody-drug conjugates in which four drug linkers are bound to heavy-light interchain thiols, is in the range of 50% to 80%.

(35)

The antibody-drug conjugate composition according to the above (34), wherein the content of antibody-drug conjugates in which four drug linkers are bound to heavy-light interchain thiols, is in the range of 50% to 70%.

(36)

The antibody-drug conjugate composition according to the above (35), wherein the content of antibody-drug conjugates in which four drug linkers are bound to heavy-light interchain thiols, is in the range of 50% to 60%.

(37)

The antibody-drug conjugate composition according to any one of the above (31) to (36), wherein the content of antibody-drug conjugates in which four drug linkers are bound to heavy-heavy interchain thiols, is 5% or less.

(38)

The antibody-drug conjugate composition according to the above (37), wherein the content of antibody-drug conjugates in which four drug linkers are bound to heavy-heavy interchain thiols, is 1% or less.

(39)

The antibody-drug conjugate composition according to any one of the above (31) to (38), wherein the content of antibody-drug conjugates in which two drug linkers are bound to heavy-heavy interchain thiols and two drug linkers are bound to heavy-light interchain thiols, is 5% or less.

(40)

The antibody-drug conjugate composition according to the above (39), wherein the content of antibody-drug conjugates in which two drug linkers are bound to heavy-heavy interchain thiols and two drug linkers are bound to heavy-light interchain thiols, is 1% or less.

(41)

The antibody-drug conjugate composition according to any one of the above (31) to (40), wherein the antibody is an anti-TROP2 antibody, an anti-CD98 antibody, an anti-B7-H3 antibody, or an anti-HER2 antibody.

(42)

The antibody-drug conjugate composition according to the above (41), wherein the antibody is an anti-TROP2 antibody.

(43)

The antibody-drug conjugate composition according to the above (41), wherein the antibody is an anti-CD98 antibody.

(44)

The antibody-drug conjugate composition according to the above (41), wherein the antibody is an anti-B7-H3 antibody.

(45)

The antibody-drug conjugate composition according to the above (41), wherein the antibody is an anti-HER2 antibody.

(46)
The antibody-drug conjugate composition according to any one of the above (31) to (45), wherein
the drug linker is
Formula 5 discloses "GGFG" as SEQ ID NO: 35.
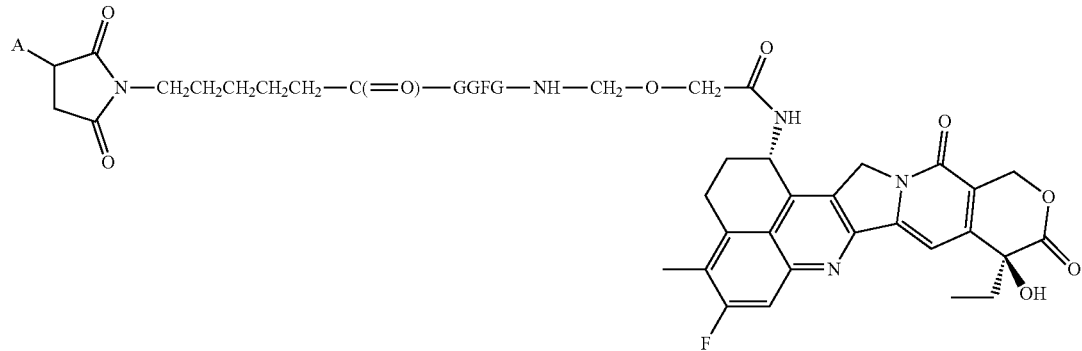
Formula 6 discloses "GGFG" as SEQ ID NO: 35.
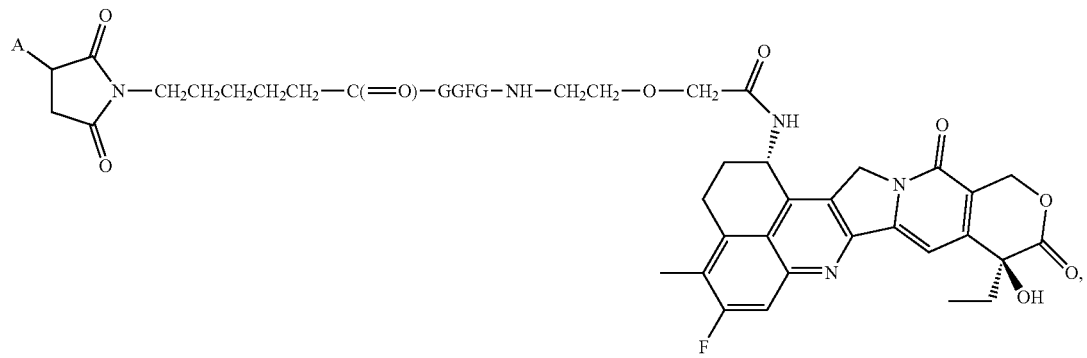
Formula 7 discloses "GGFG" as SEQ ID NO: 35.
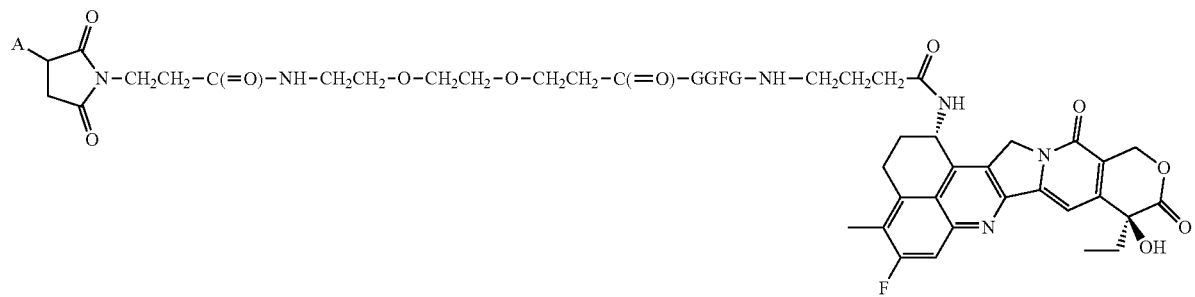

wherein A represents a binding site to the antibody, and -GGFG- represents a tetrapeptide residue consisting of glycine-glycine-phenylalanine-glycine (SEQ ID NO: 35).

(47) The antibody-drug conjugate composition according to the above (46), wherein
the drug linker is
Formula 8 discloses "GGFG" as SEQ ID NO: 35.

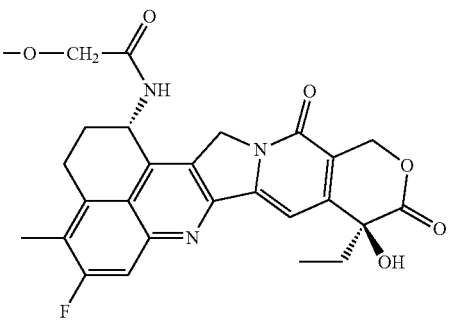

wherein A represents a binding site to the antibody, and -GGFG- represents a tetrapeptide residue consisting of glycine-glycine-phenylalanine-glycine (SEQ ID NO: 35).

(48) A pharmaceutical composition comprising the antibody-drug conjugate composition according to any one of the above (30) to (47).

(49) The pharmaceutical composition according to the above (48) for use in the treatment of tumor and/or cancer.

(50) The pharmaceutical composition according to the above (49) for use in the treatment of lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, cervical cancer, uterine cancer, head and neck cancer, esophageal cancer, bile duct cancer, thyroid cancer, lymphoma, acute myelocytic leukemia, acute lymphocytic leukemia, chronic myelogenous leukemia, and/or multiple myeloma.

(51) A method for treating tumor and/or cancer, comprising administration of the antibody-drug conjugate composition according to any one of the above (30) to (47).

(52) The treatment method according to the above (51), which is a method for treating lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, cervical cancer, uterine cancer, head and neck cancer, esophageal cancer, bile duct cancer, thyroid cancer, lymphoma, acute myelocytic leukemia, acute lymphocytic leukemia, chronic myelogenous leukemia, and/or multiple myeloma.

(53) A method for producing an antibody having thiol groups, comprising the step of reacting an antibody with a reducing agent in a buffer to reduce interchain disulfides, wherein the reaction temperature is −10° C. to 10° C., and
the produced antibody having thiol groups is used to produce an antibody-drug conjugate composition, wherein the average number of bound drugs is 3.5 to 4.5, and the content of antibody-drug conjugates in which four drug linkers are bound to heavy-light interchain thiols is 50% or more.

(54) The production method according to the above (53), wherein the produced antibody having thiol groups is used to produce an antibody-drug conjugate composition, wherein the average number of bound drugs is 4.0 to 4.1.

(55) The production method according to the above (53) or (54), wherein the produced antibody having thiol groups is used to produce an antibody-drug conjugate composition, wherein the content of antibody-drug conjugates in which four drug linkers are bound to heavy-light interchain thiols, is in the range of 50% to 90%.

(56) The production method according to the above (55), wherein the produced antibody having thiol groups is used to produce an antibody-drug conjugate composition, wherein the content of antibody-drug conjugates in which four drug linkers are bound to heavy-light interchain thiols, is in the range of 50% to 80%.

(57) The production method according to the above (56), wherein the produced antibody having thiol groups is used to produce an antibody-drug conjugate composition, wherein the content of antibody-drug conjugates in which four drug linkers are bound heavy-light interchain thiols, is in the range of 50% to 70%.

(58) The production method according to the above (57), wherein the produced antibody having thiol groups is used to produce an antibody-drug conjugate composition, wherein the content of antibody-drug conjugates in which four drug linkers are bound to heavy-light interchain thiols, is in the range of 50% to 60%.

(59) The production method according to any one of the above (53) to (58), wherein the produced antibody having thiol groups is used to produce an antibody-drug conjugate composition, wherein the content of antibody-drug conjugates in which four drug linkers are bound to heavy-heavy interchain thiols, is in the range of 5% or less.

(60)

The production method according to the above (59), wherein the produced antibody having thiol groups is used to produce an antibody-drug conjugate composition, wherein the content of antibody-drug conjugates in which four drug linkers are bound to heavy-heavy interchain thiols, is in the range of 1% or less.

(61)

The production method according to any one of the above (53) to (60), wherein the produced antibody having thiol groups is used to produce an antibody-drug conjugate composition, wherein the content of antibody-drug conjugates in which two drug linkers are bound to heavy-heavy interchain thiols and two drug linkers are bound to heavy-light interchain thiols, is 5% or less.

(62)

The production method according to the above (61), wherein the produced antibody having thiol groups is used to produce an antibody-drug conjugate composition, wherein the content of antibody-drug conjugates in which two drug linkers are bound to heavy-heavy interchain thiols and two drug linkers are bound to heavy-light interchain thiols, is 1% or less.

(63)

The production method according to any one of the above (53) to (62), wherein the reaction temperature is −5° C. to 5° C.

(64)

The production method according to the above (63), wherein the reaction temperature is −3° C. to 3° C.

(65)

The production method according to the above (64), wherein the reaction temperature is 0° C. to 2° C.

(66)

The production method according to the above (65), wherein the reaction temperature is 0° C. to 1° C.

(67)

The production method according to any one of the above (53) to (66), wherein the reducing agent is used in an amount of 2 to 3 molar equivalents per molecule of the antibody.

(68)

The production method according to any one of the above (53) to (67), wherein the reducing agent is tris(2-carboxyethyl)phosphine or a salt thereof.

(69)

The production method according to the above (68), wherein the salt of tris(2-carboxyethyl)phosphine is tris(2-carboxyethyl)phosphine hydrochloride.

(70)

The production method according to any one of the above (53) to (69), wherein the buffer is a histidine buffer.

(71)

The production method according to any one of the above (53) to (70), wherein the buffer comprises a chelating agent.

(72)

The production method according to the above (71), wherein the chelating agent is ethylenediaminetetraacetic acid.

(73)

The production method according to any one of the above (53) to (72), wherein the antibody is an anti-TROP2 antibody, an anti-CD98 antibody, an anti-B7-H3 antibody, or an anti-HER2 antibody.

(74)

The production method according to the above (73), wherein the antibody is an anti-TROP2 antibody.

(75)

The production method according to the above (73), wherein the antibody is an anti-CD98 antibody.

(76)

The production method according to the above (73), wherein the antibody is an anti-B7-H3 antibody.

(77)

The production method according to the above (73), wherein the antibody is an anti-HER2 antibody.

Advantageous Effects of Invention

According to the present invention, there are provided a method for producing an antibody-drug conjugate composition in which the number of bound drugs and the binding sites are controlled, and an antibody-drug conjugate composition in which the number of bound drugs and the binding sites are controlled. The antibody-drug conjugate composition of the present invention is excellent in terms of safety, and is useful as a medicament for the treatment of tumor and/or cancer. In addition, since an antibody-drug conjugate composition in which the number of bound drugs and the binding sites are controlled to be constant can be obtained, it is also excellent in terms of quality control and thus, is preferable.

BRIEF DESCRIPTION OF DRAWINGS

FIG. 1 is a view showing the nucleotide sequence and amino acid sequence of a humanized anti-TROP2 antibody heavy chain (hTINA1-H1).

FIG. 2 is a view showing the nucleotide sequence and amino acid sequence of a humanized anti-TROP2 antibody light chain (hTINA1-L1).

FIG. 3 is a view showing the nucleotide sequence and amino acid sequence of a humanized anti-CD98 antibody heavy chain (h23M-H1).

FIG. 4 is a view showing the nucleotide sequence and amino acid sequence of a humanized anti-CD98 antibody light chain (h23M-L1).

FIG. 5 is a graph showing the peak area ratio (%) of each chain in a humanized anti-TROP2 antibody (hTINA1-H1L1) ADC composition produced by the conventional method.

FIG. 6 is a graph showing the distribution (%) of each number of bound drugs in a humanized anti-TROP2 antibody (hTINA1-H1L1) ADC composition produced by the conventional method.

FIG. 7 is a graph showing the peak area ratio (%) of each chain in a humanized anti-TROP2 antibody (hTINA1-H1L1) ADC composition produced by the method of the present invention.

FIG. 8 is a graph showing the distribution (%) of each number of bound drugs in a humanized anti-TROP2 antibody (hTINA1-H1L1) ADC composition produced by the method of the present invention.

FIG. 9 is a graph showing the peak area ratio (%) of each chain in a humanized anti-CD98 antibody (hM23-H1L1) ADC composition produced by the conventional method.

FIG. 10 is a graph showing the distribution (%) of each number of bound drugs in a humanized anti-CD98 antibody (hM23-H1L1) ADC composition produced by the conventional method.

FIG. 11 is a graph showing the peak area ratio (%) of each chain in a humanized anti-CD98 antibody (hM23-H1L1) ADC composition produced by the method of the present invention.

FIG. 12 is a graph showing the distribution (%) of each number of bound drugs in a humanized anti-CD98 antibody (hM23-H1L1) ADC composition produced by the method of the present invention.

FIG. 13 is a view showing the amino acid sequence of a humanized anti-B7-H3 antibody heavy chain (M30-H1).

FIG. 14 is a view showing the amino acid sequence of a humanized anti-B7-H3 antibody light chain (M30-L4).

FIG. 15 is a graph showing the peak area ratio (%) of each chain in a humanized anti-B7-H3 antibody (M30-H1-L4) ADC composition produced by the conventional method.

FIG. 16 is a graph showing the distribution (%) of each number of bound drugs in a humanized anti-B7-H3 antibody (M30-H1-L4) ADC composition produced by the conventional method.

FIG. 17 is a graph showing the peak area ratio (%) of each chain in a humanized anti-B7-H3 antibody (M30-H1-L4) ADC composition produced by the method of the present invention.

FIG. 18 is a graph showing the distribution (%) of each number of bound drugs in a humanized anti-B7-H3 antibody (M30-H1-L4) ADC composition produced by the method of the present invention.

FIG. 19 is a view showing the amino acid sequence of a humanized anti-HER2 antibody heavy chain.

FIG. 20 is a view showing the amino acid sequence of a humanized anti-HER2 antibody light chain.

FIG. 21 is a graph showing the peak area ratio (%) of each chain in a humanized anti-HER2 antibody ADC composition produced by the conventional method.

FIG. 22 is a graph showing the distribution (%) of each number of bound drugs in a humanized anti-HER2 antibody ADC composition produced by the conventional method.

FIG. 23 is a graph showing the peak area ratio (%) of each chain in a humanized anti-HER2 antibody ADC composition produced by the method of the present invention.

FIG. 24 is a graph showing the distribution (%) of each number of bound drugs in a humanized anti-HER2 antibody ADC composition produced by the method of the present invention.

FIG. 25 is a graph showing the tumor growth inhibitory effect of a humanized anti-TROP2 antibody ADC composition produced by the conventional method, and the tumor growth inhibitory effect of a humanized anti-TROP2 antibody ADC composition produced by the method of the present invention.

FIG. 29 shows Formula 22 which is an example of an antibody-drug conjugate in which eight drug linkers are bound to a single antibody molecule (hereinafter also referred to as "D8") is an antibody-drug conjugate in which four drug linkers are bound to heavy-light interchain thiols and four drug linkers are bound to heavy-heavy interchain thiols.

FIG. 30 shows Formula 28 which is a Data Analysis of the light chain ($L_0$) and heavy chain ($H_0$) of an antibody to which any drug is not bound, in the case of a light chain to which a drug is bound (a light chain to which one drug is bound: $L_1$) and heavy chains to which a drug(s) is(are) bound (a heavy chain to which one drug is bound: $H_1$, a heavy chain to which two drugs are bound: $H_2$, and a heavy chain to which three drugs are bound: $H_3$), hydrophobicity is increased in proportion to the number of bound drugs, and the retention time is prolonged.

DESCRIPTION OF EMBODIMENTS

DESCRIPTION OF EMBODIMENTS

Figure 26:
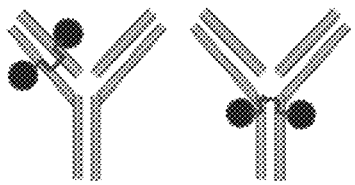
FIG. 26 shows Formula 19 which are examples of an antibody-drug conjugate in which two drugs bind to a single antibody molecule (hereinafter also referred to as "D2") include an antibody-drug conjugate in which two drug linkers are bound to heavy-light interchain thiols (hereinafter also referred to as "D2-1"), and an antibody-drug conjugate in which two drug linkers are bound to heavy-heavy interchain thiols (hereinafter also referred to as "D2-2").

In the present description, the term "cancer" is used to have the same meaning as that of the term "tumor".

In the present description, the term "gene" is used to include, not only DNA but also its mRNA and cDNA, and the cRNA thereof.

In the present description, the term "polynucleotide" is used to have the same meaning as that of a nucleic acid, and it includes DNA, RNA, a probe, an oligonucleotide, and a primer.

In the present description, the term "polypeptide" is used to have the same meaning as that of the term "protein".

In the present description, the term "cell" includes cells in an individual animal, and cultured cells.

In the present description, the term "interchain disulfide" is used to mean a disulfide located between two heavy chains in an antibody (a heavy-heavy interchain disulfide), or a disulfide located between a heavy chain and a light chain in an antibody (a heavy-light interchain disulfide).

In the present description, the term "interchain thiol" is used to mean a thiol group obtained by reducing an interchain disulfide of an antibody.

In the present description, the term "heavy-heavy interchain thiol" is used to mean a thiol group obtained by reducing a heavy-heavy interchain disulfide of an antibody.

In the present description, the term "heavy-light interchain thiol" is used to mean a thiol group obtained by reducing a heavy-light interchain disulfide of an antibody.

In the present description, the term "tumor-associated antigen (TAA)" is used to mean an antigen which is expressed in both normal cells and tumor cells, but the expression thereof is relatively restricted to tumor cells.

In the present description, the term "tumor-specific antigen (TSA)" is used to mean an antigen that is specific to tumor cells.

In the present description, the term "TROP2" is used to have the same meaning as that of a TROP2 protein.

In the present description, the term "CD98" is used to have the same meaning as that of a CD98 protein. Since CD98 consists of a heavy chain and a light chain, the terms "CD98 heavy chain" and "CD98 light chain" are used to have the same meanings as those of a CD98 heavy chain protein and a CD98 light chain protein, respectively. Moreover, in the present description, the term "CD98" is used in a manner interconvertible with any one of "CD98 heavy chain" and "CD98 light chain," or "CD98 heavy chain" or "CD98 light chain," unless otherwise specified.

In the present description, the term "anti-TROP2 antibody" is used to mean an antibody capable of binding to TROP2.

In the present description, the term "anti-CD98 antibody" is used to mean an antibody capable of binding to CD98.

In the present description, the term "anti-B7-H3 antibody" is used to mean an antibody capable of binding to B7-H3.

In the present description, the term "anti-HER2 antibody" is used to mean an antibody capable of binding to HER2.

In the present description, the term "cytotoxic" is used to mean that a pathologic change is given to cells by any given way. It does not only mean a direct external injury, but also means all types of structural or functional damages given to cells, such as DNA cleavage, formation of a base dimer, chromosomal cleavage, damage to a cell mitotic apparatus, and a reduction in the activities of various types of enzymes.

In the present description, the term "cytotoxicity" is used to mean an action to cause the above described cytotoxic phenomenon.

In the present description, the term "antibody-dependent cellular cytotoxicity" is used to means an "antibody dependent cellular cytotoxic (ADCC) activity", and this activity means the activity of NK cells to give a damage to target cells such as tumor cells, mediated by an antibody.

In the present description, the term "complement-dependent cytotoxicity" is used to mean a "complement dependent cytotoxic (CDC) activity", and this activity means the activity of a complement to give a damage to target cells such as tumor cells, mediated by an antibody.

In the present description, the term "epitope" is used to mean the partial peptide or partial three-dimensional structure of an antigen that binds to a specific antibody. Such an epitope, which is a partial peptide of an antigen, can be determined by methods well known to a person skilled in the art, such as an immunoassay, for example, by the following method. First, various partial structures of an antigen are produced. For production of such partial structures, a known oligopeptide synthesis technique can be applied. For example, a series of peptides, in which an antigen has been successively cut at an appropriate length from the C-terminus or N-terminus thereof, are produced by genetic recombination techniques well known to a person skilled in the art, and thereafter, the reactivity of an antibody with such polypeptides is studied, and recognition sites are roughly determined. Thereafter, further shorter peptides are synthesized, and the reactivity thereof with the aforementioned peptides is then studied, so as to determine an epitope. Moreover, an epitope, which is a partial three-dimensional structure of an antigen that binds to a specific antibody, can be determined by specifying the amino acid residues of an antigen adjacent to the above described antibody by X-ray structural analysis.

In the present description, the phrase "antibody binding to the same epitope" is used to mean a different antibody binding to a common epitope. If a second antibody binds to a partial peptide or a partial three-dimensional structure, to which a first antibody binds, it can be determined that the first antibody and the second antibody bind to the same epitope. In addition, by confirming that a second antibody competes with the binding of a first antibody to an antigen (i.e., a second antibody prevents a first antibody from binding to an antigen), it can be determined that the first antibody and the second antibody bind to the same epitope, although the specific sequence or structure of the epitope has not been determined. Furthermore, when a first antibody and a second antibody bind to the same epitope and further, the first antibody has special effects such as antitumor activity, the second antibody can be expected to have the same activity as that of the first antibody.

In the present description, the term "CDR" is used to mean a complementarity determining region (CDR). It is known that the heavy chain and light chain of an antibody molecule each have three CDRs. Such CDR is also referred to as a hypervariable domain, and is present in the variable region of the heavy chain and light chain of an antibody, in which the mutation of a primary structure is particularly high. The CDR is separated into three sites on the primary structure of a polypeptide chain in each of the heavy chain and light chain. In the present description, with regard to the CDR of an antibody, the CDRs of a heavy chain are referred to as CDRH1, CDRH2 and CDRH3, respectively, from the N-terminal side of the amino acid sequence of the heavy chain, whereas the CDRs of a light chain are referred to as CDRL1, CDRL2 and CDRL3, respectively, from the N-terminal side of the amino acid sequence of the light chain. These sites are located close to one another on the three-dimensional structure, and determine the specificity of the antibody to an antigen, to which the antibody binds.

In the present description, the term "several" is used to mean a number from 2 to 10. The number is preferably 2 to 9, more preferably 2 to 8, even more preferably 2 to 7, further preferably 2 to 6, still further preferably 2 to 5, still further preferably 2 to 4, much further preferably 2 or 3, and much further preferably 2.

In the present description, the term "antibody-drug conjugate composition" is used to mean a composition comprising, at any given ratio, an antibody-drug conjugate bound by two drug linkers, an antibody-drug conjugate bound by four drug linkers, an antibody-drug conjugate bound by six drug linkers, an antibody-drug conjugate bound by eight drug linkers, and an antibody not bound by any drug linker. In the present description, the "antibody-drug conjugate composition" is also referred to as an "ADC composition".

In the present description, the "average number of bound drugs" is also referred to as a drug-to-antibody ratio (DAR), and the average number of bound drugs means the average number of drugs that bind to a single antibody molecule in an antibody-drug conjugate composition.

In the present description, the term "content" is used to mean the content (molar % based on an antibody) of antibody-drug conjugates having a specific number of bound drugs and specific binding sites in an antibody-drug conjugate composition.

In the present description, the term "identity" is used to have the same meaning as that of the term "homology".

1. Antibody

The antibody used in the present invention can be generated with respect to an antigen of interest, for example, with respect to a tumor-specific antigen (TAA) or a tumor-associated antigen (TSA). Such an antibody has the property of being able to recognize tumor cells, the property of being able to bind to such tumor cells, and the property of being able to be incorporated into such tumor cells and then internalizing therein.

The type of such an antigen of interest is not particularly limited, as long as it is a tumor cell-associated antigen. Examples of the antigen of interest include B7-H3, CD3, CD30, CD33, CD37, CD56, CD98, DR5, EGFR, EPHA2, FGFR2, FGFR4, FOLR1 (Folate Receptor 1), HER2, HER3, TROP2, and VEGF.

The antibody used in the present invention can be obtained by the method described, for example, in WO2009/091048, WO2011/027808, or WO2012/133572. Specifically, a non-human animal is immunized with an antigen of interest, and lymph fluids, lymphoid tissues, blood cell samples or bone marrow-derived cells are then collected from the immunized animal. Thereafter, the plasma cells and/or plasmablasts of the non-human animal, which specifically bind to the antigen of interest, are selected. From the obtained plasma cells and/or plasmablasts, an antibody gene reacting against the antigen of interest is collected, and the nucleotide sequence of the antibody gene is then identified. Thereafter, the above described antibody or an antibody fragment thereof can be obtained based on the identified nucleotide sequence of the gene. The thus obtained antibodies are examined in terms of their binding activity to the antigen of interest, so that an antibody that is applicable to human diseases can be selected.

Alternatively, according to known methods (e.g., Kohler and Milstein, Nature (1975) 256, pp. 495-497; Kennet, R. ed., Monoclonal Antibodies, pp. 365-367, Plenum Press, N.Y. (1980)), antibody-producing cells that produce an antibody reacting against the antigen of interest are fused with myeloma cells to establish hybridomas, so as to obtain a monoclonal antibody. Specific examples of such methods are described in WO2009/048072 (published on Apr. 16, 2009) and WO2010/117011 (published on Oct. 14, 2010).

The antibody used in the present invention includes genetically recombinant antibodies, which are artificially modified for the purpose of reducing heterologous antigenicity against humans, for example, a chimeric antibody, a humanized antibody, and a human antibody. These antibodies can be produced according to known methods.

The chimeric antibody is, for example, an antibody whose variable region and constant region are heterologous to each other, such as a chimeric antibody formed by conjugating the variable region of a mouse- or rat-derived antibody to a constant region derived from a human (see Proc. Natl. Acad. Sci. U.S.A., 81, 6851-6855, (1984)).

Examples of the humanized antibody include an antibody formed by incorporating only CDR into a human-derived antibody (see Nature (1986) 321, pp. 522-525), and an antibody formed by transplanting the amino acid residues in some frameworks, as well as CDR, into a human antibody according to a CDR grafting method (International Publication No. WO90/07861).

Preferred examples of the antibody of the present invention include an anti-TROP2 antibody, an anti-CD98 antibody, an anti-B7-H3 antibody, and an anti-HER2 antibody.

An actual example of the humanized anti-TROP2 antibody can be any given combination of: a heavy chain comprising a heavy chain variable region consisting of any one of (1) an amino acid sequence consisting of amino acid residues at positions 20 to 140 of SEQ ID NO: 2, (2) an amino acid sequence having homology of at least 95% with respect to the amino acid sequence in the above (1), and (3) an amino acid sequence comprising a deletion, substitution or addition of one or several amino acids in the amino acid sequence in the above (1); and a light chain comprising a light chain variable region consisting of any one of (4) an amino acid sequence consisting of amino acid residues at positions 21 to 129 of SEQ ID NO: 4, (5) an amino acid sequence having homology of at least 95% with respect to the amino acid sequence in the above (4), and (6) an amino acid sequence comprising a deletion, substitution or addition of one or several amino acids in the amino acid sequence in the above (4).

An example of the above described antibody comprising a preferred combination of the heavy chain and the light chain can be an antibody (hTINA1-H1L1), which consists of a heavy chain consisting of an amino acid sequence consisting of amino acid residues at positions 20 to 470 of SEQ ID NO: 2, and a light chain consisting of an amino acid sequence consisting of amino acid residues at positions 21 to 234 of SEQ ID NO: 4.

The humanized anti-TROP2 antibody is not limited to a specific humanized antibody, as long as it retains CDRH1 consisting of the amino acid sequence shown in SEQ ID NO: 5 (TAGMQ), CDRH2 consisting of the amino acid sequence shown in SEQ ID NO: 6 (WINTHSGVPKYAEDFKG), CDRH3 consisting of the amino acid sequence shown in SEQ ID NO: 7 (SGFGSSYWYFDV), CDRL1 consisting of the amino acid sequence shown in SEQ ID NO: 8 (KASQDVSTAVA), CDRL2 consisting of the amino acid sequence shown in SEQ ID NO: 9 (SASYRYT), and CDRL3 consisting of the amino acid sequence shown in SEQ ID NO: 10 (QQHYITPLT), which are shown in the sequence listing.

An example of the humanized anti-CD98 antibody can be any given combination of: a heavy chain comprising a heavy chain variable region consisting of any one of (1) an amino acid sequence consisting of amino acid residues at positions 20 to 135 of SEQ ID NO: 12, (2) an amino acid sequence having identity of at least 95% with respect to the amino acid sequence in the above (1), and (3) an amino acid sequence comprising a deletion, substitution or addition of one or several amino acids in the amino acid sequence in the above (1); and a light chain comprising a light chain variable region consisting of any one of (4) an amino acid sequence consisting of amino acid residues at positions 21 to 135 of SEQ ID NO: 14, (5) an amino acid sequence having identity of at least 95% with respect to the amino acid sequence in the above (4), and (6) an amino acid sequence comprising a deletion, substitution or addition of one or several amino acids in the amino acid sequence in the above (4).

An example of the above described antibody comprising a preferred combination of the heavy chain and the light chain can be an antibody (hM23-H1L1), which consists of a heavy chain consisting of an amino acid sequence consisting of amino acid residues at positions 20 to 465 of SEQ ID NO: 12, and a light chain consisting of an amino acid sequence consisting of amino acid residues at positions 21 to 240 of SEQ ID NO: 14.

The humanized anti-CD98 antibody is not limited to a specific humanized antibody, as long as it retains CDRH1 consisting of the amino acid sequence shown in SEQ ID NO: 15 (NYLIE), CDRH2 consisting of the amino acid sequence shown in SEQ ID NO: 16 (VINPGSGVTNYNEKFKG), CDRH3 consisting of the amino acid sequence shown in SEQ ID NO: 17 (AEAWFAY), CDRL1 consisting of the amino acid sequence shown in SEQ ID NO: 18 (KSSQSLLYSSNQKNYLA), CDRL2 consisting of the amino acid sequence shown in SEQ ID NO: 19 (WASTRES), and CDRL3 consisting of the amino acid sequence shown in SEQ ID NO: 20 (QRYYGYPWT), which are shown in the sequence listing.

An example of the humanized anti-B7-H3 antibody can be any given combination of: a heavy chain comprising a heavy chain variable region consisting of any one of (1) an amino acid sequence consisting of amino acid residues at positions 20 to 141 of SEQ ID NO: 25, (2) an amino acid sequence having identity of at least 95% with respect to the amino acid sequence in the above (1), and (3) an amino acid sequence comprising a deletion, substitution or addition of one or several amino acids in the amino acid sequence in the above (1); and a light chain comprising a light chain variable region consisting of any one of (4) an amino acid sequence consisting of amino acid residues at positions 21 to 128 of SEQ ID NO: 26, (5) an amino acid sequence having identity of at least 95% with respect to the amino acid sequence in the above (4), and (6) an amino acid sequence comprising a deletion, substitution or addition of one or several amino acids in the amino acid sequence in the above (4).

An example of the above described antibody comprising a preferred combination of the heavy chain and the light chain can be an antibody (M30-H1-L4), which consists of a heavy chain consisting of an amino acid sequence consisting of amino acid residues at positions 20 to 471 of SEQ ID NO: 25, and a light chain consisting of an amino acid sequence consisting of amino acid residues at positions 21 to 233 of SEQ ID NO: 26.

The humanized anti-B7-H3 antibody is not limited to a specific humanized antibody, as long as it retains CDRH1 consisting of the amino acid sequence shown in SEQ ID NO: 27 (NYVMH), CDRH2 consisting of the amino acid sequence shown in SEQ ID NO: 28 (YINPYNDDVKYNEKFKG), CDRH3 consisting of the amino acid sequence shown in SEQ ID NO: 29 (WGYYGSPLYYFDY), CDRL1 consisting of the amino acid sequence shown in SEQ ID NO: 30 (RASSRLIYMH), CDRL2 consisting of the amino acid sequence shown in SEQ ID NO: 31 (ATSNLAS), and CDRL3 consisting of the amino acid sequence shown in SEQ ID NO: 32 (QQWNSNPPT), which are shown in the sequence listing.

An example of the humanized anti-HER2 antibody can be an antibody, which consists of a heavy chain consisting of an amino acid sequence consisting of amino acid residues at positions 1 to 449 of SEQ ID NO: 33, and a light chain consisting of an amino acid sequence consisting of amino acid residues at positions 1 to 214 of SEQ ID NO: 34 (trastuzumab; U.S. Pat. No. 5,821,337).

Moreover, a CDR-modified humanized antibody, in which 1 to 3 amino acid residues in each CDR are substituted with other amino acid residues, is also included in the antibody used in the present invention, as long as the CDR-modified humanized antibody has binding activity to tumor cells.

The antibody used in the present invention further includes a human antibody. Such a human antibody can be obtained by a method of using a human antibody-producing mouse having a human chromosomal fragment comprising the heavy chain and light chain genes of a human antibody (see Tomizuka, K. et. al., Nature Genetics (1997) 16, pp. 133-143; Kuroiwa, Y. et. al., Nucl. Acids Res. (1998) 26, pp. 3447-3448; Yoshida, H. et. al., Animal Cell Technology: Basic and Applied Aspects vol. 10, pp. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, pp. 722-727; etc.).

Furthermore, there are known methods of obtaining a human antibody that is derived from a phage display selected from a human antibody library (see Wormstone, I. M. et. al, Investigative Ophthalmology & Visual Science. (2002) 43(7), pp. 2301-2308; Carmen, S. et. al., Briefings in Functional Genomics and Proteomics (2002), 1(2), pp. 189-203; Siriwardena, D. et. al., Ophthalmology (2002) 109(3), pp. 427-431; etc.).

For instance, a phage display method comprising allowing the variable region of a human antibody to express as a single-chain antibody (scFv) on the surface of a phage, and then selecting a phage binding to an antigen, can be used (Nature Biotechnology (2005), 23, (9), pp. 1105-1116). By analyzing the gene of a phage selected based on its binding activity to an antigen, a DNA sequence encoding the variable region of a human antibody binding to an antigen can be determined. If the DNA sequence of scFv binding to an antigen were elucidated, it would become possible to obtain a human antibody by producing an expression vector having the DNA sequence, and then introducing the expression vector into a suitable host (WO92/01047, WO92/20791, WO93/06213, WO93/11236, WO93/19172, WO95/01438, WO95/15388, Annu. Rev. Immunol (1994) 12, pp. 433-455, Nature Biotechnology (2005) 23(9), pp. 1105-1116).

The binding activity of the above described antibody to an antigen of interest is evaluated, so that a preferred antibody can be selected. The dissociation constant between an antibody and an antigen can be measured by using Biacore T200 (GE Healthcare Bioscience), which involves Surface Plasmon Resonance (SPR) as a detection principle. For instance, an antibody, which is adjusted to have a suitable concentration with respect to an antigen that is solid-phased as a ligand, is allowed to react with an analyte, and its association and dissociation are then measured, so as to obtain an association rate constant ka1, a dissociation rate constant kd1, and a dissociation constant (KD; KD=kd1/ka1). The binding activity to an antigen of interest can be evaluated, not only with the use of Biacore T200, but also by using an apparatus involving Surface Plasmon Resonance (SPR) as a detection principle, KinExA (Sapidyne Instruments) involving Kinetic Exclusion Assay as a detection principle, BLitz System (Pall) involving Bio-Layer Interferometry as a detection principle, an ELISA (Enzyme-Linked ImmunoSorbent Assay) method, or the like.

The activity of internalizing in cells can be confirmed by applying (1) an assay of visualizing an antibody incorporated into cells under a fluorescence microscope, using a secondary antibody (fluorescent label) binding to a therapeutic antibody (Cell Death and Differentiation (2008) 15, 751-761), (2) an assay of measuring the amount of fluorescence incorporated into cells, using a secondary antibody (fluorescent label) binding to a therapeutic antibody (Molecular Biology of the Cell Vol. 15, 5268-5282, December 2004), or (3) a Mab-ZAP assay, in which immunotoxin that binds to a therapeutic antibody is used, and when the immunotoxin is incorporated into cells, toxin is released and cell growth is suppressed (BioTechniques 28: 162-165, January 2000). As such an immunotoxin, a recombinant conjugated protein consisting of a catalytic region of diphtheria toxin and a protein G can also be used.

An example of another indicator used for a comparison of the properties of antibodies can be the stability of antibody. Differential scanning calorimetry (DSC) is a method capable of promptly and precisely measuring a thermal denaturation midpoint (Tm) serving as a good indicator for the relative structural stability of a protein. By using DSC to measure such Tm values and then comparing the obtained values, a difference in thermal stability can be compared. It is known that the preservation stability of an antibody shows a certain degree of correlation with the thermal stability of an antibody (Lori Burton, et. al., Pharmaceutical Development and Technology (2007) 12, pp. 265-273), and using thermal stability as an indicator, a preferred antibody can be selected. Examples of other indicators for selection of an antibody include a high yield in suitable host cells, and low cohesiveness in an aqueous solution. For example, since an antibody with the highest yield does not always exhibit the highest thermal stability, a comprehensive decision is made based on the aforementioned indicators, and an antibody, which is most suitably administered to humans, needs to be selected.

Moreover, by regulating sugar chain modification binding to an antibody, antibody-dependent cytotoxicity can be enhanced. As techniques of regulating the sugar chain modification of an antibody, those described in WO99/54342, WO2000/61739, WO2002/31140, etc. are known, but the techniques are not limited thereto.

When an antibody gene has been isolated and thereafter, the gene introduced into a suitable host to produce an antibody, a suitable combination of a host and an expression vector can be used. A specific example of the antibody gene can be a combination of a gene encoding the heavy chain sequence of the antibody described in the present description and a gene encoding the light chain sequence of the antibody described therein. For transformation of host cells, a heavy chain sequence gene and a light chain sequence gene can be inserted into a single expression vector, or these genes can also be inserted each into different expression vectors. When eukaryotic cells are used as hosts, animal cells, plant cells, eukaryotic microorganisms can be used. Examples of the animal cells include mammalian cells such as COS cells which are monkey cells (Gluzman, Y., Cell (1981) 23, pp. 175-182, ATCC CRL-1650), mouse fibroblasts NIH3T3 (ATCC No. CRL-1658), and a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, pp. 4126-4220). On the other hand, when prokaryotic cells are used as hosts, *Escherichia coli* or *Bacillus subtilis* can be used, for example. An antibody gene of interest is introduced into these cells for transformation, and the transformed cells are then cultured in vitro to obtain an antibody. In the aforementioned culture method, there is the case where the yield is different depending on the sequence of an antibody, and thus, it is possible to select an antibody, which is easily produced as a medicament, from antibodies having equivalent binding activity, using the yield as an indicator.

Isotypes of the antibody used in the present invention are not limited, and examples of the isotype of the present antibody include IgG (IgG1, IgG2, IgG3, and IgG4), IgM, IgA (IgA1 and IgA2), IgD, and IgE. Among others, IgG or IgM is preferable, and IgG1, IgG2 or IgG3 is more preferable.

Examples of the general function of an antibody include antigen-binding activity, activity of neutralizing the activity of an antigen, activity of enhancing the activity of an antigen, antibody-dependent cytotoxicity, complement-dependent cytotoxicity, complement-dependent cellular cytotoxicity, and internalization activity.

Further, the antibody used in the present invention may be a multispecific antibody having specificity to at least two types of different antigens. In general, such a molecule binds to two types of antigen (i.e., a bispecific antibody). However, the "multispecific antibody" in the present invention includes an antibody having specificity to more antigens (e.g., 3 types of antigens).

The antibody used in the present invention may be an antibody having identity (or homology) of 80% to 99% to the heavy chain and/or light chain of the above described antibody. By combining sequences having high homology to the above described heavy chain amino acid sequence and light chain amino acid sequence, an antibody having antigen-binding activity and internalization activity that are equivalent to those of each of the above described antibodies can be selected. Such homology is homology of generally 80% or more, preferably 90% or more, more preferably 95% or more, and most preferably 99% or more. In addition, by combining amino acid sequences comprising a substitution, deletion and/or addition of one to several amino acid residues with respect to the amino acid sequences of a heavy chain and/or a light chain, an antibody having various types of actions that are equivalent to those of each of the above described antibodies can be selected. The number of amino acid residues to be substituted, deleted and/or added is generally 10 or less amino acid residues, preferably 9 or less amino acid residues, more preferably 8 or less amino acid residues, more preferably 7 or less amino acid residues, even more preferably 6 or less amino acid residues, further preferably 5 or less amino acid residues, still further preferably 4 or less amino acid residues, still further preferably 3 or less amino acid residues, still further preferably 2 or less amino acid residues, and most preferably 1 amino acid residue.

It is known that the lysine residue at the carboxyl terminus of the heavy chain of an antibody produced in cultured mammalian cells is deleted (Journal of Chromatography A, 705: 129-134 (1995)), and also, it is known that the two amino acid residues at the heavy chain carboxyl terminus, glycine and lysine, are deleted, and that the proline residue positioned at the carboxyl terminus is newly amidated (Analytical Biochemistry, 360: 75-83 (2007)). However, deletion and modification of these heavy chain sequences do not have an influence on the antigen-binding activity and effector function (activation of a complement, antibody-dependent cytotoxicity, etc.) of an antibody. Accordingly, the present invention also includes an antibody that has undergone the aforementioned modification, and specific examples of such an antibody include a deletion mutant comprising a deletion of 1 or 2 amino acids at the heavy chain carboxyl terminus, and an a deletion mutant formed by amidating the aforementioned deletion mutant (e.g., a heavy chain in which the proline residue at the carboxyl terminal site is amidated). However, deletion mutants regarding a deletion at the carboxyl terminus of the heavy chain of the antibody according to the present invention are not limited to the above described deletion mutants, as long as they retain antigen-binding activity and effector function. Two heavy chains constituting the antibody according to the present invention may be any one type of heavy chain selected from the group consisting of a full length antibody and the above described deletion mutants, or a combination of any two types selected from the aforementioned group. The amount ratio of individual deletion mutants can be influenced by the types of cultured mammalian cells that produce the antibody according to the present invention, and culture conditions. The main ingredient of the antibody according to the present invention can be the case where one amino acid residue is deleted at each of the carboxyl termini of the two heavy chains.

Homology between two types of amino acid sequences can be determined by using the default parameter of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs," Nucleic Acids Res. 25: 3389-3402). The Blast algorithm is also available by accessing www.ncbi.nlm.nih.gov/blast on the internet. It is to be noted that, using the above described Blast algorithm, two types of percentage values, namely, Identity (or Identities) and Positivity (or Positivities), can be calculated. The former is a value obtained when amino acid residues are identical between two types of amino acid sequences, the homology of which is to be obtained. The latter is a numerical value, for which amino acid residues having a similar chemical structure are also considered. In the present description, the value of identity when amino acid residues are identical to each other is defined as the value of homology.

The obtained antibody can be purified until it becomes homogenous. For separation and purification of the antibody, ordinary separation and purification methods, which are applied to proteins, may be used. An antibody can be separated and purified by appropriately selecting methods, for example, from column chromatography, filtration, ultra-filtration, salting-out, dialysis, preparative polyacrylamide gel electrophoresis and isoelectric focusing, and then combining the selected methods (Strategies for Protein Purification and Characterization: A Laboratory Course Manual, Daniel R. Marshak et. al., eds., Cold Spring Harbor Laboratory Press (1996); Antibodies: A Laboratory Manual. Ed Harlow and David Lane, Cold Spring Harbor Laboratory (1988)), but the separation and purification methods are not limited thereto.

Examples of the chromatography include affinity chromatography, ion exchange chromatography, hydrophobic chromatography, gel filtration chromatography, reverse phase chromatography, and adsorption chromatography.

These chromatographic methods can be carried out by using liquid chromatography such as HPLC or FPLC.

Examples of a column used in affinity chromatography include a protein A column and a protein G column.

2. Drug

The drug used in the present invention is not particularly limited, as long as it is a compound having antitumor effects and also having a substituent or a partial structure capable of binding to a linker structure. Regarding such a drug, a part of or the entire linker is cleaved in a tumor cell, and an antitumor compound portion is released, so that antitumor effects are exhibited. If the linker is cleaved at a binding portion to the drug, an antitumor compound is released while having its original structure, so that the original antitumor effects are exhibited. The drug is allowed to bind to the antibody via a linker portion having a specific structure. In the present description, a drug linker including this drug and this linker portion is also referred to a "drug".

Examples of the antitumor compound include calicheamicin, doxorubicin, daunorubicin, mitomycin C, bleomycin, cyclocytidine, vincristine, vinblastine, methotrexate, cisplatin or a derivative thereof, auristatin or a derivative thereof, maytansine or a derivative thereof, taxol or a derivative thereof, and camptothecin or a derivative thereof. Among these compounds, exatecan or monomethyl auristatin E are preferable.

Exatecan ((1S,9S)-1-amino-9-ethyl-5-fluoro-2,3-dihydro-9-hydroxy-4-methyl-1H,12H-benzo[de]pyrano[3',4': 6,7]indolizino[1,2-b]quinoline-10,13(9H,15H)-dione), which is a camptothecin derivative, is a compound represented by the following formula.

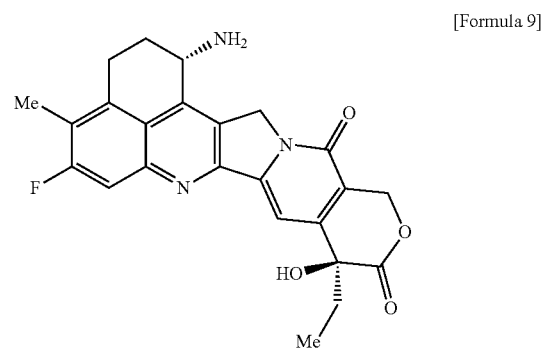 [SMILES: CC[C@@]1(O)C(=O)OCc2c1cc1n(c2=O)Cc2c-1nc1cc(F)c(C)c3c1c2[C@@H](N)CC3]

[Formula 9]

Monomethyl auristatin E ((2R,3R)—N-[(1R,2S)-1-methyl-2-hydroxy-2-phenylethyl]-2-methyl-3-[(2S)-1-[(3R,4S,5S)-3-methoxy-4-[(N-methyl-L-Val-L-Val-)(methyl)amino]-5-methylheptanoyl]-2-pyrrolidinyl]-3-methoxypropanamide) is a compound represented by the following formula.

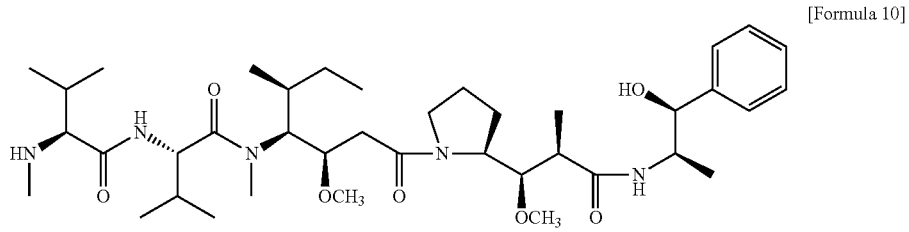 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

[Formula 10]

3. Linker

The drug used in the present invention can be bound to an antibody via a linker. The linker used in the present invention preferably has an N-substituted maleimidyl group. Examples of the linker include a cleavable linker and a non-cleavable linker. An example of the cleavable linker is a peptide linker cleaved by intracellular protease such as lysosomal protease or endosomal protease.

The linker used in the present invention preferably has a structure induced from any one of the following formulae:

Formula 11 discloses "GGFG" as SEQ ID NO: 35.

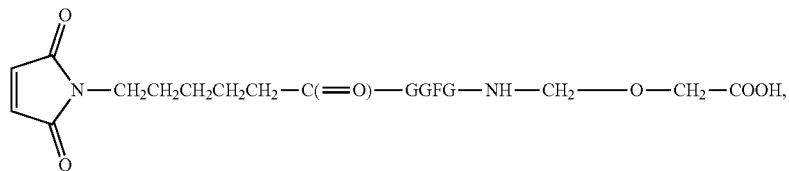

Formula 12 discloses "GGFG" as SEQ ID NO: 35.

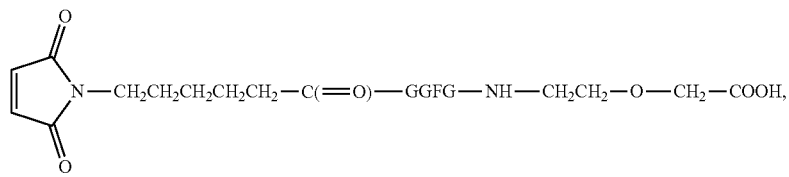

and
Formula 13 discloses "GGFG" as SEQ ID NO: 35.

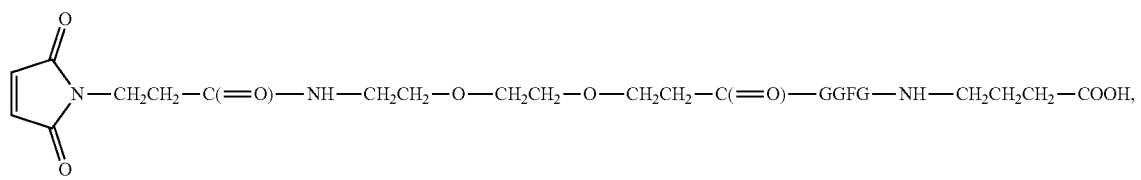

and preferably has a structure induced from the following formula:
Formula 14 discloses "GGFG" as SEQ ID NO: 35.

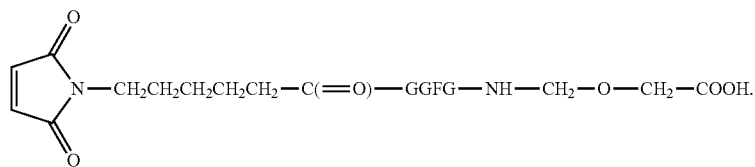

The term "GGFG" means a tetrapeptide residue consisting of glycine-glycine-phenylalanine-glycine (SEQ ID NO: 35).

The linker used in the present invention can be prepared, for example, according to the method described in Example 58 of WO2014/057687.

4. Drug Linker Intermediate

The drug linker intermediate used in the present invention can be produced by reacting the carboxyl group of the above described linker compound with the amino group of an antitumor compound, using a condensing agent, etc.

The drug linker intermediate used in the method of the present invention is not particularly limited, as long as it is a compound subjectable to a reaction with an interchain thiol of an antibody. The present drug linker intermediate is preferably a compound having an N-substituted maleimidyl group, and it is more preferably, Formula 15 discloses "GGFG" as SEQ ID NO: 35.
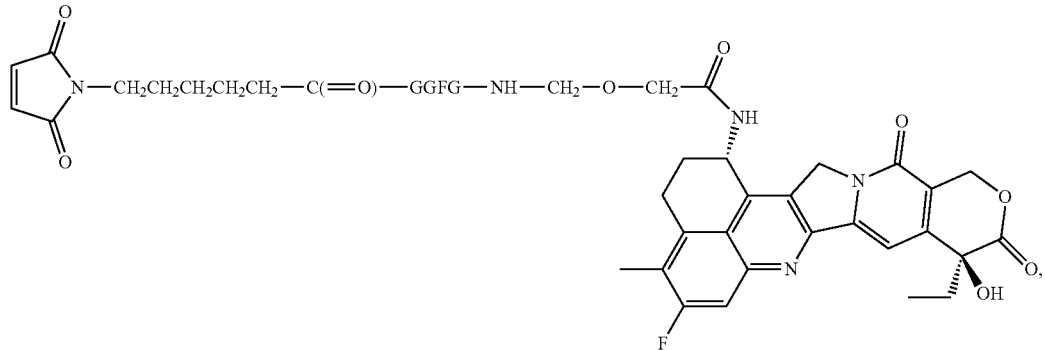
Formula 16 discloses "GGFG" as SEQ ID NO: 35.
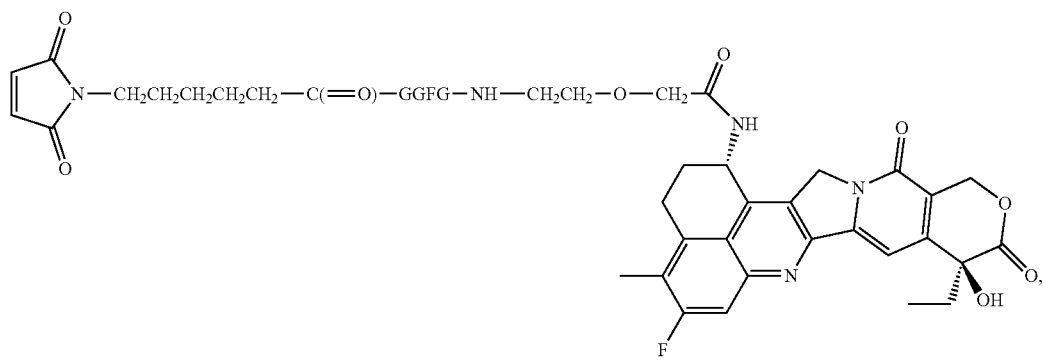
or
Formula 17 discloses "GGFG" as SEQ ID NO: 35.
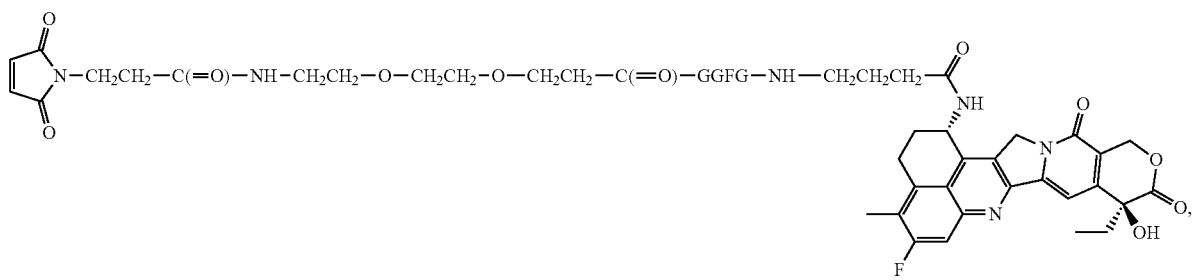

and it is further preferably,
Formula 18 discloses "GGFG" as SEQ ID NO: 35.

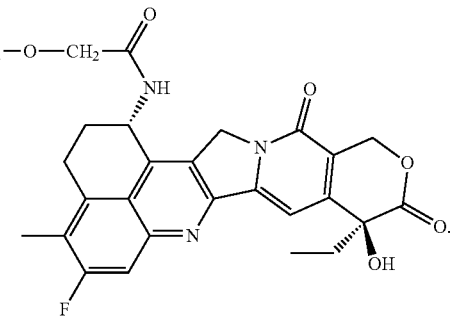

The drug linker intermediate used in the present invention can be prepared, for example, according to the methods described in Example 58, Example 43 and Example 14 of WO2014/057687.

If the present drug linker intermediate is a drug linker intermediate having an N-substituted maleimidyl group, it is allowed to react with an interchain thiol generated by reduction of an interchain disulfide of an antibody, so that the antibody can be allowed to bind to the drug via the linker. Accordingly, the drug linker intermediate is preferably a compound having an N-substituted maleimidyl group. However, the drug linker intermediate used herein is not limited to such a compound, and all types of drug linker intermediates can be applied to the production method of the present invention, as long as they have a functional group for promoting the reaction with an interchain thiol of an antibody.

5. Antibody-Drug Conjugate

Regarding an antibody-drug conjugate, the number of drugs binding to a single antibody molecule is an important factor that has an influence on efficacy and safety. Since an antibody has four interchain disulfides and such a disulfide is constituted with two thiol groups, the number of drug binding to a single antibody molecule is 2, 4, 6, or 8.

Examples of an antibody-drug conjugate in which two drugs bind to a single antibody molecule (hereinafter also referred to as "D2") include an antibody-drug conjugate in which two drug linkers are bound to heavy-light interchain thiols (hereinafter also referred to as "D2-1"), and an antibody-drug conjugate in which two drug linkers are bound to heavy-heavy interchain thiols (hereinafter also referred to as "D2-2") (see FIG. 26).

Figure 27:
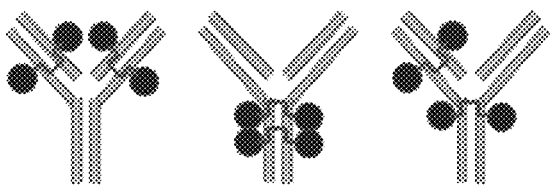
FIG. 27 shows Formula 20 which are examples of an antibody-drug conjugate in which four drugs bind to a single antibody molecule (hereinafter also referred to as "D4") include an antibody-drug conjugate in which four drug linkers are bound to heavy-light interchain thiols (hereinafter also referred to as "D4-1"), an antibody-drug conjugate in which four drug linkers are bound to heavy-heavy interchain thiols (hereinafter also referred to as "D4-2"), and an antibody-drug conjugate in which two drug linkers are bound to heavy-light interchain thiols and two drug linkers are bound to heavy-heavy interchain thiols (hereinafter also referred to as "D4-3").

Examples of an antibody-drug conjugate in which four drugs bind to a single antibody molecule (hereinafter also referred to as "D4") include an antibody-drug conjugate in which four drug linkers are bound to heavy-light interchain thiols (hereinafter also referred to as "D4-1"), an antibody-drug conjugate in which four drug linkers are bound to heavy-heavy interchain thiols (hereinafter also referred to as "D4-2"), and an antibody-drug conjugate in which two drug linkers are bound to heavy-light interchain thiols and two drug linkers are bound to heavy-heavy interchain thiols (hereinafter also referred to as "D4-3") (see FIG. 27).

Figure 28:
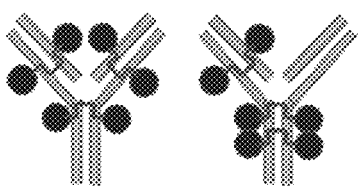
FIG. 28 shows Formula 21 which are examples of an antibody-drug conjugate in which six drugs bind to a single antibody molecule (hereinafter also referred to as "D6") include an antibody-drug conjugate in which four drug linkers are bound to heavy-light interchain thiols and two drug linkers are bound to heavy-heavy interchain thiols (hereinafter also referred to as "D6-1"), and an antibody-drug conjugate in which two drug linkers are bound to heavy-light interchain thiols and four drug linkers are bound to heavy-heavy interchain thiols thereinafter also referred to as "D6-2").

Examples of an antibody-drug conjugate in which six drugs bind to a single antibody molecule (hereinafter also referred to as "D6") include an antibody-drug conjugate in which four drug linkers are bound to heavy-light interchain thiols and two drug linkers are bound to heavy-heavy interchain thiols (hereinafter also referred to as "D6-1"), and an antibody-drug conjugate in which two drug linkers are bound to heavy-light interchain thiols and four drug linkers are bound to heavy-heavy interchain thiols (hereinafter also referred to as "D6-2") (see FIG. 28).

An example of an antibody-drug conjugate in which eight drug linkers are bound to a single antibody molecule (hereinafter also referred to as "D8") (see FIG. 29) is an antibody-drug conjugate in which four drug linkers are bound to heavy-light interchain thiols and four drug linkers are bound to heavy-heavy interchain thiols.

The interchain thiol of an antibody forms a thioether, for example, with the 3-position of the N-substituted maleimidyl group of a drug linker intermediate, and binds thereto. That is, the binding portion of an antibody with a drug linker is represented, for example, by the following formula:

[Formula 23]

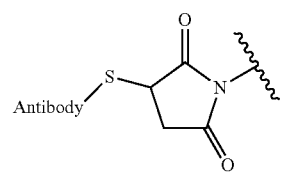

wherein "Antibody-S-" is derived from the antibody.

The drug linker is preferably,
Formula 24 discloses "GGFG" as SEQ ID NO: 35.
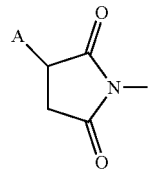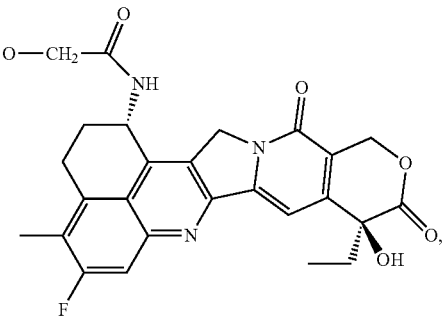
Formula 25 discloses "GGFG" as SEQ ID NO: 35.
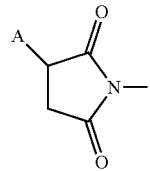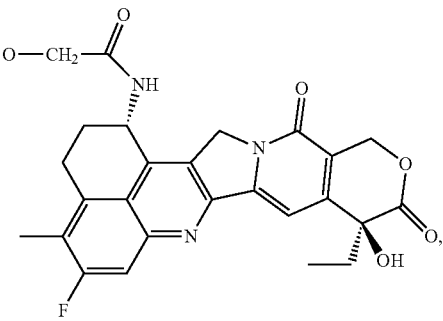
or
Formula 26 discloses "GGFG" as SEQ ID NO: 35.
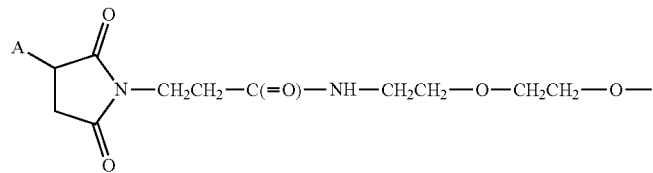
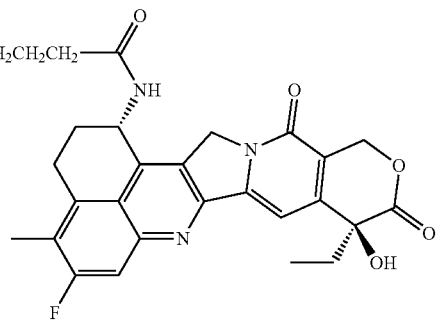

wherein A represents the binding site to the antibody, and it is more preferably, Formula 27 discloses "GGFG" as SEQ ID NO: 35.

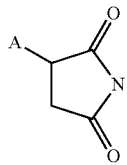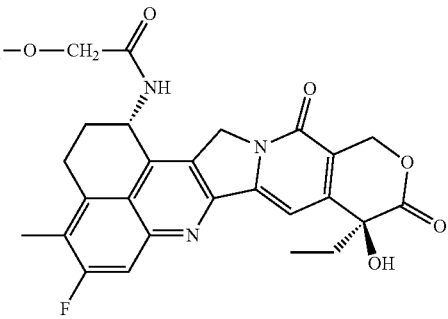

wherein A represents the binding site to the antibody.

An antibody-drug conjugate is produced, while determining reaction conditions such as the amounts of raw materials and/or reagents used in the reaction, so that the number of bound drugs can be controlled. Differing from the chemical reaction of a low molecular weight compound, the antibody-drug conjugate is generally obtained in the form of a mixture to which different numbers of drugs bind. The number of drugs binding to a single antibody molecule is specified and indicated as a mean value, namely, the average number of bound drugs.

The production method of the present invention is a method for producing an antibody-drug conjugate composition in which the number of bound drugs and the binding sites are controlled, and the present production method consists of a first step of selectively reducing heavy-light interchain disulfide(s) of an antibody to convert them to thiol groups, and a second step of reacting drug linker intermediates with the antibody having thiol groups, so as to produce an antibody-drug conjugate composition in which the number of bound drugs and the binding sites are controlled. Hereafter, each step will be described in detail.

(First Step) Reduction of Antibody

An antibody having thiol groups can be produced by reacting an antibody with a reducing agent in a buffer at a temperature of −10° C. to 10° C.

The reaction temperature is preferably −5° C. to 5° C., more preferably −3° C. to 3° C., even more preferably 0° C. to 2° C., and further preferably 0° C. to 1° C.

The amount of the reducing agent is 1 to 4 molar equivalents, and preferably 2 to 3 molar equivalents, based on the amount of a single antibody molecule.

As such a reducing agent, for example, tris(2-carboxyethyl)phosphine or a salt thereof, dithiothreitol, or 2-mercaptoethanol can be used. The reducing agent is preferably tris(2-carboxyethyl)phosphine or a salt thereof, and more preferably tris(2-carboxyethyl)phosphine hydrochloride.

As a buffer, a histidine buffer, a phosphate buffer, a borate buffer, an acetate buffer, a HEPES (4-(2-hydroxyethyl)-1-piperazineethanesulfonic acid) buffer or the like can be used, and among others, a histidine buffer is preferable.

The buffer preferably comprises a chelating agent. Examples of the chelating agent that can be used herein include ethylenediaminetetraacetic acid (hereinafter also referred to as "EDTA") and diethylenetriaminepentaacetic acid. Among others, ethylenediaminetetraacetic acid is preferable. Such a buffer may be used in a concentration of 1 to 20 mM.

The reaction time is preferably 1 to 15 hours, more preferably 3 to 10 hours, and even more preferably 5 to 7 hours.

The pH applied for the reaction is pH 5 to 9, preferably pH 6 to 8, and more preferably pH 6.8 to 7.2.

(Second Step) Conjugation of Antibody to Drug Linker Intermediate

Drug linker intermediates are allowed to react with the antibody having thiol groups obtained in the first step to produce an antibody-drug conjugate composition. The drug linker intermediates are used in an amount of 2 to 10 molar equivalents, and preferably 4 to 6 molar equivalents, based on the amount of a single antibody molecule.

Specifically, a solution in which the drug linker intermediate has been dissolved is added to a buffer comprising the antibody having thiol groups obtained in the first step, so that they may be allowed to react with each other.

Examples of the solvent in which the drug linker intermediate is dissolved, which can be used herein, include organic solvents such as a 50% acetone aqueous solution, a 80% ethanol aqueous solution, a 80% methanol aqueous solution, a 80% isopropanol aqueous solution, a 80% dimethyl sulfoxide aqueous solution, dimethyl sulfoxide (DMSO), dimethylformamide (DMF), dimethylacetamide (DMA), and N-methyl-2-pyrrolidone (NMP). Among these solvents, a 50% acetone aqueous solution or an 80% dimethyl sulfoxide aqueous solution is preferable.

The organic solvent solution, in which the drug linker intermediate has been dissolved, is added in an amount of 1% to 20% v/v to a buffer comprising the antibody having thiol groups, so that they may be allowed to react with each other.

The reaction temperature is preferably −10° C. to 10° C., more preferably −5° C. to 5° C., and even more preferably 0° C. to 2° C.

The reaction time is preferably 0.5 to 2 hours.

The conjugation reaction can be terminated by deactivating the reactivity of unreacted drug linker intermediates with a thiol group-containing reagent.

As such a thiol group-containing reagent, for example, cysteine or N-acetyl-L-cysteine can be used. More specifically, the conjugation reaction can be terminated by adding N-acetyl-L-cysteine in an amount of 1 to 2 molar equivalents to the used drug linker intermediate, and then reacting them at room temperature for 10 to 30 minutes.

After completion of the conjugation reaction, purification can be carried out using a commercially available ultrafiltration membrane or the like. While an acetate buffer, a histidine buffer, a phosphate buffer or the like is added to the reaction product, a low molecular weight portion can be removed by using the ultrafiltration membrane. As such an ultrafiltration membrane, an appropriate ultrafiltration membrane may be used. An ultrafiltration membrane having a molecular weight of 1 kDa to 100 kDa may be used, and an ultrafiltration membrane having a molecular weight of 30 kDa is preferable.

6. Identification of Antibody-Drug Conjugate Composition

The produced antibody-drug conjugate composition is subjected to concentration, buffer exchange, purification, and the measurement of an antibody concentration and the average number of bound drugs, according to the following operations, so that the antibody-drug conjugate composition can be identified.

(1) Concentration of Antibody or Antibody-Drug Conjugate Aqueous Solution

An antibody or an antibody-drug conjugate solution is placed in a vessel of Amicon Ultra (50,000 MWCO, Millipore Corporation), and is then subjected to a centrifugal operation (centrifuged at 2000 G to 3800 G for 5 to 20 minutes), using a centrifuge (Allegra X-15R, Beckman Coulter, Inc.), so that the antibody or the antibody-drug conjugate solution can be concentrated.

(2) Measurement of Antibody Concentration

Using a UV measurement apparatus (Nanodrop 1000, Thermo Fisher Scientific Inc.), the concentration of the antibody can be measured according to the method provided by the manufacturer. During the measurement, 280 nm absorption coefficients (1.3 mLmg$^{-1}$ cm$^{-1}$ to 1.8 mLmg$^{-1}$ cm$^{-1}$) which are different depending on individual antibodies, are used.

(3) Exchange of Buffer for Antibody

A NAP-25 column (Cat. No. 17-0852-02, GE Healthcare Japan Corporation), in which a Sephadex G-25 carrier is used, is equilibrated with a phosphate buffer containing sodium chloride (137 mM) and ethylenediaminetetraacetic acid (5 mM) (10 mM, pH 6.0; hereinafter also referred to as "PBS6.0/EDTA") according to the method provided by the manufacturer. Thereafter, 2.5 mL of an antibody aqueous solution is applied to a single NAP-25 column, and a fraction (3.5 mL) eluted with 3.5 mL of PBS6.0/EDTA is then fractionated. This fraction is concentrated by the same method as that described in the above (1), and the concentration of the antibody is then measured by the same method as that described in the above (2). Thereafter, the concentration of the antibody can be adjusted using PBS6.0/EDTA.

(4) Purification of Antibody-Drug Conjugate Composition

A NAP-25 column is equilibrated with an acetate buffer containing sorbitol (5%) (10 mM, pH 5.5; hereinafter also referred to as "ABS"). To this NAP-25 column, an antibody-drug conjugate reaction aqueous solution (2.5 mL) is applied, and it is then eluted with a buffer in an amount determined by the manufacturer, so as to fractionate an antibody fraction. This fraction is applied again to the NAP-25 column, and then, a gel filtration purification operation involving elution with a buffer is repeated two or three times in total, so as to obtain an antibody-drug conjugate composition, from which unbound drug linker intermediates or low molecular weight compounds (tris(2-carboxyethyl) phosphine hydrochloride, N-acetyl-L-cysteine and dimethyl sulfoxide) have been removed.

(5) Separation Method of Using Hydrophobic Column Chromatography for Antibody-Drug Conjugate Composition (5-1) HPLC Measurement Method An HPLC analysis was carried out under the following measurement conditions.

HPLC system: Shimadzu Science HPLC System

Detector: Ultraviolet absorption spectrometer (measurement wavelength: 280 nm)

Column: TSKgel Butyl-NPR (4.6×100 mm, 2.5 µm; TOSOH CORPORATION)

Column temperature: 30° C.

Mobile phase A: 25 mM Phosphate buffer (pH 7.0) aqueous solution comprising 1.5 M ammonium sulfate Mobile phase B: Mixed solution comprising 75% of 25 mM phosphate buffer (pH 7.0) and 25% of isopropyl alcohol Gradient program: 20%-60% (0 min-20 min), 20%-80% (20 min-20.1 min), 80%-80% (20.1 min-23 min), 80%-20% (23 min-23.1 min), 20%-20% (23.1 min-40 min)

Injected sample amount: 2 µL (5-2) Data Analysis

Regarding the present data, since antibody-drug conjugates are eluted in the order of increasing the number of bound drugs based on a difference in the salt concentration because of the characteristics of the column, the distribution in the number of bonds can be assumed by measuring individual area values. The peaks are D0 (an antibody not bound by any drug linker), D2, D4-1, D4-2, D6 and D8 in the order of elution, and thus, the distribution condition can be grasped.

The content of antibody-drug conjugates, in which the number of bound drugs is 4, in the antibody-drug conjugate composition produced by the production method of the present invention is 50% or more.

The content of D4-1 in the antibody-drug conjugate composition produced by the production method of the present invention is 50% or more, or in the range of 50% to 90%, 50% to 80%, 50% to 70%, or 50% to 60%.

The content of D4-2 in the antibody-drug conjugate composition produced by the production method of the present invention is preferably 5% or less, and more preferably 1% or less.

The content of D4-3 in the antibody-drug conjugate composition produced by the production method of the present invention is preferably 5% or less, and more preferably 1% or less.

(6) Measurement of Antibody Concentration and the Average Number of Bound Drugs in Antibody-Drug Conjugate Composition (UV Method)

The concentration of bound drugs in the antibody-drug conjugate composition can be calculated by measuring the UV absorbance of an antibody-drug conjugate aqueous solution at two wavelengths, 280 nm and 370 nm, and then carrying out the following calculation.

Since the total absorbance at a certain wavelength is equal to a sum of the absorbances of all absorbing chemical species in the system [additivity of absorbance], if it is assumed that the molar absorption coefficients of an antibody and a drug are not changed before and after conjugation of the antibody to the drug, the antibody concentration and the drug concentration in the antibody-drug conjugate composition are represented by the following relational expressions.

$$A_{280}=A_{D,280}+A_{A,280}=\varepsilon_{D,280}C_D+\varepsilon_{A,280}C_A \quad \text{Expression (1)}$$

$$A_{370}=A_{D,370}+A_{A,370}=\varepsilon_{D,370}C_D+\varepsilon_{A,370}C_A \quad \text{Expression (2)}$$

In the above expressions, $A_{280}$ represents the absorbance of an antibody-drug conjugate aqueous solution at 280 nm, $A_{370}$ represents the absorbance of an antibody-drug conjugate aqueous solution at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in an antibody-drug conjugate composition, and $C_D$ represents the drug concentration in an antibody-drug conjugate composition.

Herein, for the values represented by $\varepsilon_{A,280}$, $\varepsilon_{A,370}$, $\varepsilon_{D,280}$ and $\varepsilon_{D,370}$, previously prepared values (estimated calculation values, or measured values obtained by the UV measurement of a compound) are used. For example, the value $\varepsilon_{A,280}$ can be assumed from the amino acid sequence of the antibody according to a known calculation method (Protein Science, 1995, vol. 4, 2411-2423). The value $\varepsilon_{A,370}$ is generally zero. The values $\varepsilon_{D,280}$ and $\varepsilon_{D,370}$ can be obtained by measuring the absorbance of a solution, in which the used conjugate precursor is dissolved in a certain concentration, according to the Lambert-Beer law (absorbance=molar concentration×molar absorption coefficient×cell light path length). The values $A_{280}$ and $A_{370}$ of the antibody-drug conjugate aqueous solution are measured, and the obtained values are then substituted into the formulae (1) and (2) to solve the simultaneous equations, thereby obtaining $C_A$ and $C_D$. Moreover, $C_D$ is divided by $C_A$ to obtain the average number of bound drugs per antibody.

(7) Measurement of the Average Number of Bound Drugs Per Single Antibody Molecule in Antibody-Drug Conjugate Composition (RPC Method)

The average number of bound drugs per single antibody molecule in an antibody-drug conjugate composition can also be obtained by the below-mentioned high performance liquid chromatography (HPLC) analysis using a reversed phase chromatography (RPC) method, instead of the aforementioned UV method.

(7-1) Preparation of Sample Used for HPLC Analysis (Reduction of Antibody-Drug Conjugate)

An antibody-drug conjugate solution (approximately 1 mg/mL, 60 μL) is mixed with a dithiothreitol (DTT) aqueous solution (100 mM, 15 μL). The mixture is incubated at 37° C. for 30 minutes, so as to obtain a sample, in which interchain disulfides of the antibody-drug conjugate have been cleaved, and thereafter, the obtained sample is used in an HPLC analysis.

(7-2) HPLC Analysis

An HPLC analysis is carried out under the following measurement conditions.

HPLC system: Agilent 1290 HPLC system (Agilent Technologies)

Detector: Ultraviolet absorption spectrometer (measurement wavelength: 280 nm)

Column: PLRP-S (2.1×50 mm, 8 μm, 1000 Å; Agilent Technologies, P/N PL1912-1802)

Column temperature: 80° C.

Mobile phase A: 0.04% Trifluoroacetic acid (TFA) aqueous solution

Mobile phase B: Acetonitrile solution containing 0.04% TFA

Gradient program: 29%-36% (0 min-12.5 min), 36%-42% (12.5 min-15 min), 42%-29% (15 min-15.1 min), 29%-29% (15.1 min-25 min)

Injected sample amount: 15 μL (7-3) Data Analysis (7-3-1) When compared with the light chain ($L_0$) and heavy chain ($H_0$) of an antibody to which any drug is not bound, in the case of a light chain to which a drug is bound (a light chain to which one drug is bound: $L_1$) and heavy chains to which a drug(s) is(are) bound (a heavy chain to which one drug is bound: $H_1$, a heavy chain to which two drugs are bound: $H_2$, and a heavy chain to which three drugs are bound: $H_3$), hydrophobicity is increased in proportion to the number of bound drugs, and the retention time is prolonged. Thus, elution takes place in the order of $L_0$, $L_1$, $H_0$, $H_1$, $H_2$, and $H_3$. As a result of making a comparison in terms of the retention time between $L_0$ and $H_0$, the detection peak can be assigned to any one of $L_0$, $L_1$, $H_0$, $H_1$, $H_2$, and H3 (see FIG. 30).

(7-3-2) Since a drug linker absorbs UV, peak area values are corrected according to the following expressions, using the molar absorption coefficients of a light chain, a heavy chain, and a drug linker, depending on the number of bound drug linkers.

$$\text{Light chain peak area correction value } (L_i) = \text{Peak area} \times \frac{\text{Molar absorption coefficent of light chain}}{\text{Molar absorption coefficient of light chain} + \text{the number of bound drugs} \times \text{molar absorption coefficient of drug linker}}$$ [Expression 1]

$$\text{Heavy chain peak area correction value } (H_i) = \text{Peak area} \times \frac{\text{Molar absorption coefficent of heavy chain}}{\text{Molar absorption coefficient of heavy chain} + \text{the number of bound drugs} \times \text{molar absorption coefficient of drug linker}}$$ [Expression 2]

Herein, with regard to the molar absorption coefficients (280 nm) of the light chain and heavy chain of each antibody, values assumed from the amino acid sequences of the light chain and heavy chain of each antibody according to a known calculation method (Protein Science, 1995, vol. 4, 2411-2423) can be used. Moreover, with regard to the molar absorption coefficient (280 nm) of a drug linker, the actually measured molar absorption coefficient (280 nm) of a compound prepared by reacting each drug linker intermediate with mercaptoethanol or N-acetyl cysteine and then converting an N-substituted maleimidyl group to a succinimide thioether can be used.

(7-3-3) The peak area ratio (%) of each chain to a total of peak area correction values is calculated according to the following expression.

$$\text{Light chain peak area ratio} = \frac{A_{Li}}{A_{L0} + A_{L1}} \times 100$$ [Expression 3]

$$\text{Heavy chain peak area ratio} = \frac{A_{Hi}}{A_{H0} + A_{H1} + A_{H2} + A_{H3}} \times 100$$

Peak area correction value of each of $A_{Li}$, $A_{Hi}$: $L_i$, $H_i$

If $L_1$ and $H_1$ have been preferentially generated, it can be assumed that the heavy-light interchain disulfides have been selectively reduced. On the other hand, if $L_0$ and $H_2$ have been preferentially generated, it can be assumed that the heavy-heavy interchain disulfides have been selectively reduced.

(7-3-4) The average number of bound drugs in an antibody-drug conjugate composition is calculated according to the following expression.

The average number of bound drugs=($L_0$ peak area ratio×0+$L_1$ peak area ratio×1+$H_0$ peak area ratio×0+$H_1$ peak area ratio×1+$H_2$ peak area ratio×2+$H_3$ peak area ratio×3)/100×2

The average number of bound drugs in the antibody-drug conjugate composition produced by the production method of the present invention is preferably 3.5 to 4.5, and more preferably 4.0 to 4.1.

7. Medicament Comprising Antibody-Drug Conjugate Composition

After the antibody-drug conjugate composition obtained by the present invention has been transferred into tumor cells, the linker portion thereof is cleaved, and the drug is released in the tumor cells.

In the case of an antibody-drug conjugate represented by the following formula:

Formula 29 discloses "GGFG" as SEQ ID NO: 35.

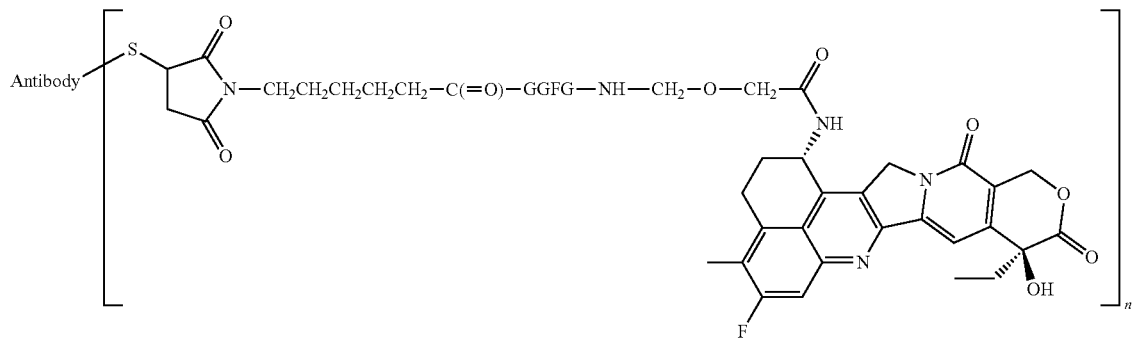

a compound represented by the following formula:

[Formula 30]

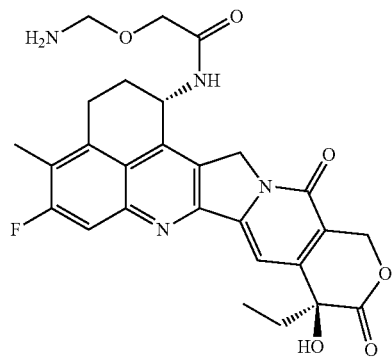

is released. Since this compound has an unstable aminal structure, it is further hydrolyzed, so that a compound represented by the following formula:

[Formula 31]

can be generated.

In the case of an antibody-drug conjugate represented by the following formula:

Formula 32 discloses "GGFG" as SEQ ID NO: 35.

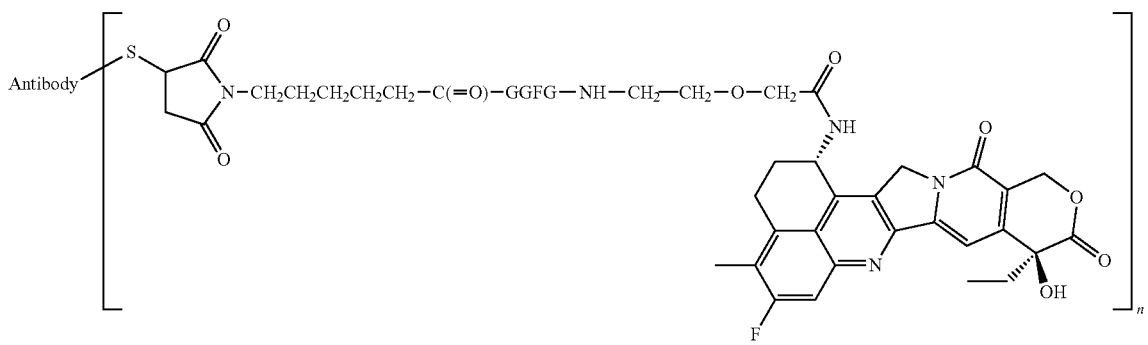

a compound represented by the following formula:

[Formula 33]

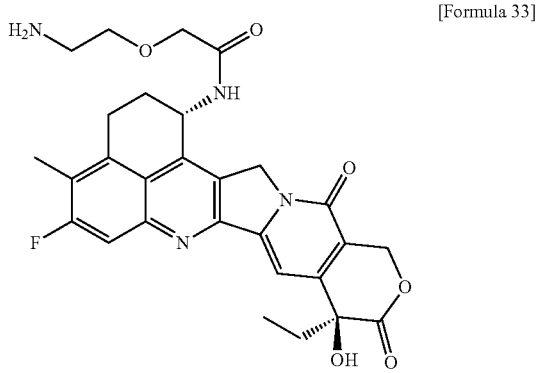 [SMILES: CC[C@@]1(O)C(=O)OCc2c1cc1n(c2=O)Cc2c-1nc1cc(F)c(C)c3c1c2[C@@H](NC(=O)COCCN)CC3]

is released.

In the case of an antibody-drug conjugate represented by the following formula:

Formula 34 discloses "GGFG" as SEQ ID NO: 35.

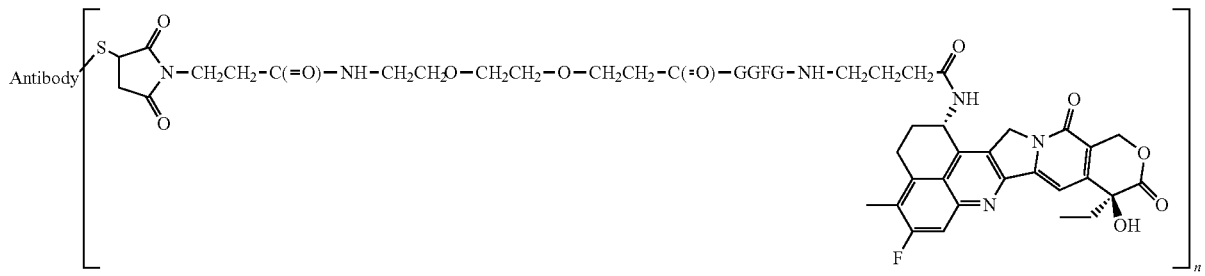

a compound represented by the following formula:

[Formula 35]

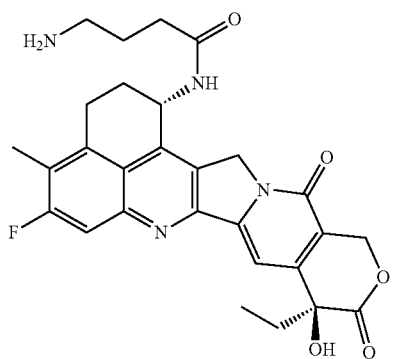

is released.

Since the antibody-drug conjugate composition obtained by the present invention exhibits cytotoxicity on cancer cells, it can be used as an active ingredient of a pharmaceutical composition for treating and/or preventing cancer.

That is to say, the antibody-drug conjugate composition obtained by the present invention can be selected and used as an agent for chemotherapy that is a principal treatment method in cancer therapy, and as a result of the use thereof, the growth of cancer cells can be retarded, the proliferation thereof can be suppressed, and further, cancer cells can be destroyed. By doing so, the release from symptoms caused by cancer or the improvement of QOL can be achieved for cancer patients, and the life of the cancer patients can be kept, so that therapeutic effects can be achieved. Even in the case where the destroying of cancer cells cannot be achieved, higher QOL of cancer patients can be achieved by the suppression or control of the growth of the cancer cells, so that the survival of the patients can be achieved for a longer period of time.

The antibody-drug conjugate composition obtained by the present invention can be used, not only in the form of a drug alone in such drug therapy, but also in the form of an agent that is combined with other therapies in adjuvant therapy. The present antibody-drug conjugate composition can be combined with surgical operation, radiation therapy, hormone therapy, etc. Moreover, the present antibody-drug conjugate composition can also be used as an agent used for drug therapy in neoadjuvant therapy.

In addition to the aforementioned therapeutic use, the antibody-drug conjugate composition obtained by the present invention can be expected to have the effect of suppressing the growth of very small metastatic cancer cells and further destroying such metastatic cancer cells. For instance, the present antibody-drug conjugate composition can be expected to have the effect of suppressing and destroying cancer cells in a body fluid in a metastatic process, or the effect of suppressing and destroying very small cancer cells, which are immediately after having adhered to any tissues. Therefore, the present antibody-drug conjugate composition can be expected to have the effect of suppressing and preventing cancer metastasis, particularly after the removal of cancer by surgical operation.

The antibody-drug conjugate composition obtained by the present invention is not only administered to a patient by systemic therapy, but it can also be expected that the antibody-drug conjugate composition will be topically administered to cancer tissues and will exhibit therapeutic effects thereon.

Examples of the type of cancer include lung cancer, kidney cancer, urothelial cancer, colon cancer, prostate cancer, glioblastoma multiforme, ovarian cancer, pancreatic cancer, breast cancer, melanoma, liver cancer, bladder cancer, stomach cancer, cervical cancer, uterine cancer, head and neck cancer, esophageal cancer, bile duct cancer, thyroid cancer, lymphoma, acute myelocytic leukemia, acute lymphocytic leukemia, chronic myelogenous leukemia, and multiple myeloma, but are not limited thereto.

The antibody-drug conjugate composition obtained by the present invention can be used as an active ingredient of a pharmaceutical composition for treating autoimmune disease, or a pharmaceutical composition for suppressing a rejection reaction against transplantation.

When a pharmaceutical composition comprising the antibody-drug conjugate composition obtained by the present invention is administered to a mammal (e.g., a human, a horse, a bovine, a swine, etc., and preferably, a human), it can be administered systemically or topically, and preferably by parenteral administration.

Examples of the administration route for parenteral administration include intradermal, intramuscular, intraperitoneal, intravenous and subcutaneous routes, but are not limited thereto. Examples of the administration method include injection and bolus injection, and the administration method is preferably injection.

The pharmaceutical composition of the present invention can be prepared by selecting a suitable form depending on the administration method, and then applying a commonly used method of preparing various types of preparations. For instance, the antibody-drug conjugate composition obtained by the present invention is mixed with a solvent such as a sterilized liquid (including water and oil (oil derived from petroleum, animals, vegetables, or synthetic oil (e.g., peanut oil, soybean oil, mineral oil, sesame oil, etc.)), a saline, a dextrose aqueous solution, or a glycerol aqueous solution, and additives such as a moisturizer, an emulsifier, or a pH buffer, which are described in "Remington's Pharmaceutical Sciences" written by E. W. Martin, and the like, so as to prepare the pharmaceutical composition of the present invention.

The pharmaceutical composition of the present invention may comprise a solubilizer, a local anesthetic (e.g., lignocaine) for relieving pain at an injection site, etc. The pharmaceutical composition of the present invention may be supplied in an aspect in which an active ingredient, a solvent and the like are each placed in different vessels. Moreover, when the pharmaceutical composition of the present invention is administered by injection, it may be administered, for example, in the form of an injection bottle containing an active ingredient and a sterilized-drug-grade water or saline. When the pharmaceutical composition of the present invention is administered by injection, the active ingredient may be mixed with sterilized water for injection or saline, before the administration thereof.

The pharmaceutical composition of the present invention may comprise an antibody-drug conjugate composition and at least one cancer therapeutic agent other than the aforementioned antibody-drug conjugate composition. The antibody-drug conjugate composition obtained by the present invention can also be administered together with other cancer therapeutic agents, and the present antibody-drug conjugate composition can thereby enhance anticancer effects. Other anticancer agents used for such a purpose may be administered to an individual subject, simultaneously, separately, or continuously with the present antibody-drug conjugate composition. Otherwise, such other anticancer agents may also be administered at administration intervals that are different from those of the present antibody-drug conjugate composition. Examples of such a cancer therapeutic agent include carboplatin, cisplatin, gemcitabine, irinotecan (CPT-11), paclitaxel, pemetrexed, sorafenib, vinblastin, the agents described in International Publication No. WO2003/038043, and further, LH-RH analogs (leuprorelin, goserelin, etc.), estramustine-phosphate, estrogen antagonists (tamoxifen, raloxifene, etc.), and aromatase inhibitors (anastrozole, letrozole, exemestane, etc.). However, the type of the cancer therapeutic agent is not limited, as long as it is an agent having antitumor activity.

The pharmaceutical composition of the present invention may also be provided in the form of a freeze-dried preparation or a liquid preparation. When the present pharmaceutical composition is provided as a freeze-dried preparation, it may be a preparation comprising suitable preparation additives that are used in the concerned technical field. Also, when the present pharmaceutical composition is provided as a liquid preparation, it may be a preparation comprising suitable preparation additives that are used in the concerned technical field.

The composition of the pharmaceutical composition of the present invention and the concentration of an active ingredient thereof are changed depending on an administration method. In the case of the antibody-drug conjugate composition comprised in the pharmaceutical composition of the present invention, as the affinity of the antibody-drug conjugate for the antigen is increased, namely, as the affinity is increased in terms of the dissociation constant (Kd value) of the antibody-drug conjugate to the antigen (i.e., as the Kd value is decreased), the antibody-drug conjugate composition is able to exhibit medicinal effects, although it is administered in a small amount. Accordingly, for determination of the applied dose of the antibody-drug conjugate composition, the dose can be determined based on the condition of the affinity of the antibody-drug conjugate for the antigen. When the antibody-drug conjugate composition produced by the production method of the present invention is administered to a human, the present antibody-drug conjugate composition may be administered, for example, at a dose of approximately 0.001 to 100 mg/kg to the human, once, or divided over several administrations, at intervals of once per 1 to 180 days.

The present invention will be specifically described in the following Examples. However, these examples are not intended to limit the scope of the present invention. In addition, the following Examples are not restrictively interpreted in any sense. Moreover, the reagents, solvents and starting materials described in the present description can be easily acquired from commercially available supply sources, unless otherwise specified.

EXAMPLES (Example 1) Construction of Humanized Anti-TROP2 Antibody Expression Vector and Production of Antibody (i) Construction of Humanized Anti-TROP2 Antibody Heavy Chain (hTINA1-H1) Expression Vector A DNA fragment comprising a DNA sequence encoding the variable region of a humanized anti-TROP2 antibody heavy chain (hTINA1-H1) that is represented by nucleotide numbers 36 to 437 in the nucleotide sequence of a humanized anti-TROP2 antibody heavy chain (hTINA1-H1) shown in SEQ ID NO: 2 in the sequence listing was synthesized (Artificial Gene Synthesis Service, GENEART). Using the synthesized DNA fragment as a template, a DNA fragment comprising a DNA sequence encoding the variable region of a humanized anti-TROP2 antibody heavy chain (hTINA1-H1) was amplified with KOD-Plus- (TOYOBO) and the following primer set. Thereafter, an expression vector for chimeric and humanized antibody IgG1-type heavy chains, pCMA-G1, was cleaved with the restriction enzyme BlpI, and the DNA fragment was then inserted into the cleaved site, using In-Fusion HD PCR cloning kit (CLONTECH), so as to construct a humanized anti-TROP2 antibody heavy chain (hTINA1-H1) expression vector. The obtained expression vector was named "pCMA-G1/hTINA1-H1".

Primer Set:

```
                         (SEQ ID NO: 21: primer EG-Inf-F)
     5'-agctcccagatgggtgctgagc-3'

(SEQ ID NO: 22: primer EG1-Inf-R)
     5'-gggcccttggtggaggctgagc-3'
```

(ii) Construction of Humanized Anti-TROP2 Antibody Light Chain (hTINA1-L1) Expression Vector A DNA fragment comprising a DNA sequence encoding the variable region of a humanized anti-TROP2 antibody light chain (hTINA1-L1) that is represented by nucleotide numbers 38 to 402 in the nucleotide sequence of a humanized anti-TROP2 antibody light chain (hTINA1-L1) shown in SEQ ID NO: 4 in the sequence listing was synthesized (Artificial Gene Synthesis Service, GENEART). Using the synthesized DNA fragment as a template, a DNA fragment comprising a DNA sequence encoding the variable region of a humanized anti-TROP2 antibody light chain (hTINA1-L1) was amplified with KOD-Plus- (TOYOBO) and the following primer set. Thereafter, an expression vector for chimeric and humanized antibody light chains, pCMA-LK, was cleaved with the restriction enzyme BsiWI, and the DNA fragment was then inserted into the cleaved site, using In-Fusion HD PCR cloning kit (CLONTECH), so as to construct a humanized anti-TROP2 antibody light chain (hTINA1-L1) expression vector. The obtained expression vector was named "pCMA-LK/hTINA1-L1".

Primer Set:

```
                         (SEQ ID NO: 23: primer CM-LKF)
     5'-ctgtggatctccggcgcgtacggc-3'

(SEQ ID NO: 24: primer KCL-Inf-R)
     5'-ggaggggcggccaccgtacg-3'
```

(iii) Production of Humanized Anti-TROP2 Antibody (hTINA1-H1L1)

FreeStyle 293F cells (Invitrogen) were subcultured and cultured according to the instruction manual. Specifically, $1.2 \times 10^9$ FreeStyle 293F cells (Invitrogen), which were in the logarithmic growth phase, were inoculated in a 3 L Fernbach Erlenmeyer Flask (CORNING), and were then diluted with a FreeStyle 293 expression medium (Invitrogen) to adjust to $1.0 \times 10^6$ cells/mL. Thereafter, the cells were subjected to shaking culture at 37° C. in an 8% $CO_2$ incubator at 90 rpm for 1 hour. Thereafter, Polyethyleneimine (Polyscience #24765; 3.6 mg) was dissolved in Opti-Pro SFM (Invitrogen; 20 mL), and thereafter, a light chain expression vector (0.8 mg) and a heavy chain expression vector (0.4 mg), which had been prepared using PureLink HiPure Plasmid kit (Invitrogen), were added to Opti-Pro SFM (Invitrogen; 20 mL). The expression vector/Opti-Pro SFM mixed solution (20 mL) was added to the Polyethyleneimine/Opti-Pro SFM mixed solution (20 mL), and thereafter, the obtained mixture was gently stirred and was then left for 5 minutes. Thereafter, the FreeStyle 293F cells were added to the reaction mixture. The thus obtained mixture was subjected to shaking culture at 37° C. in an 8% $CO_2$ incubator for 7 days at 90 rpm, and the obtained culture supernatant was then filtrated with Disposable Capsule Filter (ADVANTEC #CCS-045-E1H).

The humanized anti-TROP2 antibody obtained by the combination of pCMA-G1/hTINA1-H1 with pCMA-LK/hTINA1-L1 was named "hTINA1-H1L1".

(iv) Purification of Humanized Anti-TROP2 Antibody (hTINA1-H1L1)

An antibody was purified from the culture supernatant obtained in the above (iii) by a two-step process, namely, by rProtein A affinity chromatography (4° C.-6° C.) and ceramic hydroxyapatite (room temperature). After the purification by rProtein A affinity chromatography and after the purification using ceramic hydroxyapatite, a buffer substitution step was carried out at 4° C. to 6° C. First, the culture supernatant was applied to MabSelect SuRe (HiTrap column, manufactured by GE Healthcare Bioscience), which had been equilibrated with PBS. After the entire culture supernatant had been placed in the column, the column was washed with PBS in an amount of two times or more of the volume of the column. Subsequently, elution was carried out using a 2 M arginine hydrochloride solution (pH 4.0), so as to collect a fraction comprising the antibody. The fraction was substituted with PBS according to dialysis (Slide-A-Lyzer Dialysis Cassette, Thermo Scientific), and thereafter, an antibody solution, which had been five times diluted with a buffer consisting of 5 mM sodium phosphate and 50 mM MES (pH 7.0), was applied to a ceramic hydroxyapatite column (Bio-Scale CHTType-I Hydroxyapatite Column, JAPAN Bio-Rad Laboratories K. K.), which had been equilibrated with a buffer consisting of 5 mM NaPi, 50 mM MES and 30 mM NaCl (pH 7.0). Subsequently, linear concentration gradient elution was carried out using sodium chloride, and a fraction comprising the antibody was collected. The fraction was substituted with HBSor (25 mM histidine/5% sorbitol, pH 6.0) according to dialysis (Slide-A-Lyzer Dialysis Cassette, Thermo Scientific). Finally, the resultant was concentrated using Centrifugal UF Filter Device VIVAS-PIN20 (cut-off molecular weight: UF10K, Sartorius, 4° C.), and the IgG concentration was adjusted to 20 mg/mL or more, so as to prepare a purified sample.

(v) Buffer Exchange for Humanized Anti-TROP2 Antibody (hTINA1-H1L1) and Adjustment of Concentration A NAP-25 column (Cat. No. 17-0852-02, GE Healthcare Japan Corporation), in which a Sephadex G-25 carrier was used, was equilibrated with a phosphate buffer containing sodium chloride (137 mM) and ethylenediaminetetraacetic acid (5 mM) (10 mM, pH 6.0; hereinafter also referred to as "PBS6.0/EDTA") according to the method provided by the manufacturer. 2.5 mL of an antibody aqueous solution comprising the humanized anti-TROP2 antibody (hTINA1-H1L1) produced in the above (iv) was applied to a single NAP-25 column described above, and a fraction (3.5 mL) eluted with 3.5 mL of PBS6.0/EDTA was collected. This fraction was placed in a vessel of Amicon Ultra (50,000 MWCO, Millipore Corporation), and was then subjected to a centrifugation operation (centrifuged at 2000 G to 3800 G for 5 to 20 minutes) using a centrifuge (Allegra X-15R, Beckman Coulter, Inc.), so as to concentrate the antibody solution. Using a UV measurement apparatus (Nanodrop 1000, Thermo Fisher Scientific Inc.), the concentration of the antibody was measured according to the method provided by the manufacturer. For the measurement, the concentration of the antibody was measured using a 280 nm absorption coefficient (1.54 mLmg$^{-1}$ cm$^{-1}$), and thereafter, using PBS6.0/EDTA, the antibody concentration was adjusted to 21.8 mg/mL.

(Example 2) Production of Drug Linker Intermediate

N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, which is represented by the following formula, was synthesized by the method described in Example 58 of WO2014/057687.

Formula 36 discloses "GGFG" as SEQ ID NO: 35.

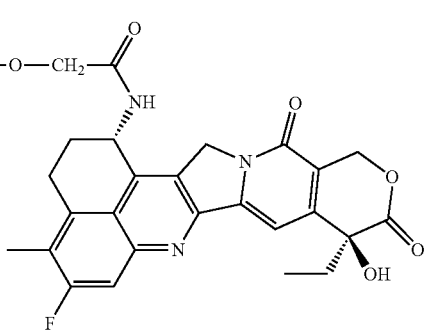

(Example 3) Production of Humanized Anti-TROP2 Antibody ADC Composition

(Example 3-1) Production of Humanized Anti-TROP2 Antibody (hTINA1-H1L1) ADC Composition According to Conventional Method (i) Reduction of Antibody A humanized anti-TROP2 antibody (hTINA1-H1L1) (15 mL; corresponding to 327 mg, concentration: 21.8 mg/mL; 25 mM histidine buffer) was placed in a glass reaction vessel, and further, a 25 mM histidine buffer (18 mL, pH 5.0) was added thereto. To the present reaction solution, a 0.5 M EDTA aqueous solution (0.027 mL; 6 equivalents based on the antibody) was added, and thereafter, a 0.1 g/mL polysorbate 20 aqueous solution (0.033 mL; 0.01% based on the antibody) was added thereto. Thereafter, a 0.3 M disodium hydrogen phosphate aqueous solution was added to the reaction mixture, so that the mixture was adjusted to pH 7.12. Under stirring at 24° C., a 1.00 mg/mL tris(2-carboxyethyl)phosphine hydrochloride aqueous solution (1.58 mL; 2.45 equivalents per single antibody molecule) was added to the reaction mixture, and the obtained mixture was then heated for 3 hours to result in an internal temperature of 35° C. to 36° C., so that interchain disulfides of the antibody were reduced.

(ii) Conjugation of Antibody to Drug Linker Intermediate

The solution obtained in the above (i) was cooled, and a 6.67 mg/mL 50% acetone aqueous solution (1.71 mL; 5.2 equivalents per single antibody molecule) of the compound obtained in Example 2 was then added to the reaction solution at an internal temperature of 16° C. to 17° C. under stirring over 60 minutes. The obtained mixture was stirred at the same temperature as described above for 20 minutes, so that the drug linker intermediate was allowed to bind to the antibody. Subsequently, a 50 mM N-acetylcysteine aqueous solution (0.135 mL; 3 equivalents per single antibody molecule) was added to the reaction mixture, and the thus obtained mixture was further stirred at the same temperature as described above for 20 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 500 mL, so that low molecular weight substances were removed. Thereafter, the remaining solution was concentrated to obtain 17.6 mL of a solution containing a humanized anti-TROP2 antibody (hTINA1-H1L1) ADC composition.

(iv) Evaluation of Properties

[Common Operation A] Measurement of the Average Number of Bound Drugs Per Single Antibody Molecule in Antibody-Drug Conjugate Composition The average number of bound drugs per single antibody molecule in an antibody-drug conjugate composition was obtained by a high performance liquid chromatography (HPLC) analysis of using the following method.

1. Preparation of Sample Used in HPLC Analysis (Reduction of Antibody-Drug Conjugate)

An antibody-drug conjugate solution (approximately 1 mg/mL, 60 μL) was mixed with a dithiothreitol (DTT) aqueous solution (100 mM, 15 μL). The mixture was incubated at 37° C. for 30 minutes to prepare a sample in which the disulfides between the heavy chain and the light chain and between the heavy chain and the heavy chain of the antibody-drug conjugate were cleaved. The obtained sample was used in an HPLC analysis.

2. HPLC Analysis

An HPLC analysis was carried out under the following measurement conditions.

HPLC system: Shimadzu Science HPLC System

Detector: Ultraviolet absorption spectrometer (measurement wavelength: 280 nm)

Column: PLRP-S (2.1×50 mm, 8 μm, 1000 Å; Agilent Technologies)

Column temperature: 80° C.

Mobile phase A: 0.05% Trifluoroacetic acid (TFA) aqueous solution

Mobile phase B: Acetonitrile solution containing 0.04% TFA

Gradient program: 29%-36% (0 min-12.5 min), 36%-42% (12.5-15 min), 42%-29% (15 min-15.1 min), 29%-29% (15.1 min-25 min)

Injected sample amount: 15 μL

4. Data Analysis

When compared with the light chain ($L_0$) and heavy chain ($H_0$) of an antibody to which a drug did not bind, in the case of a light chain to which a drug bound (a light chain to which one drug bound: $L_1$) and heavy chains to which a drug(s) bound (a heavy chain to which one drug bound: $H_1$, a heavy chain to which two drugs bound: $H_2$, and a heavy chain to which three drugs bound: $H_3$), hydrophobicity was increased in proportion to the number of bound drugs, and the retention time was prolonged. Thus, elution took place in the order of $L_0$, $L_1$, $H_0$, $H_1$, $H_2$, and $H_3$. As a result of making a comparison in terms of the retention time between $L_0$ and $H_0$, the detection peak was assigned to any one of $L_0$, $L_1$, $H_0$, $H_1$, $H_2$, and $H_3$.

Since a drug linker absorbed UV, peak area values were corrected according to the following expressions, using the molar absorption coefficients of a light chain, a heavy chain, and a drug linker, depending on the number of bound drug linkers.

$$\text{Light chain peak area correction value } (L_i) = \text{Peak area} \times \frac{\text{Molar absorption coefficent of light chain}}{\text{Molar absorption coefficient of light chain} + \text{the number of bound drugs} \times \text{molar absorption coefficient of drug linker}} \quad [\text{Expression 4}]$$

$$\text{Heavy chain peak area correction value } (H_i) = \text{Peak area} \times \frac{\text{Molar absorption coefficent of heavy chain}}{\text{Molar absorption coefficient of heavy chain} + \text{the number of bound drugs} \times \text{molar absorption coefficient of drug linker}} \quad [\text{Expression 5}]$$

Herein, with regard to the molar absorption coefficients (280 nm) of the light chain and heavy chain of each antibody, values assumed from the amino acid sequences of the light chain and heavy chain of each antibody according to a known calculation method (Protein Science, 1995, vol. 4, 2411-2423) were used. In the case of the humanized anti-TROP2 antibody (hTINA1-H1L1), based on its amino acid sequence, the number 27640 was used as an estimated value for the molar absorption coefficient of the light chain, and the number 83810 was used as an estimated value for the molar absorption coefficient of the heavy chain. Moreover, with regard to the molar absorption coefficient (280 nm) of a drug linker, the actually measured molar absorption coefficient (280 nm) of a compound prepared by reacting each drug linker intermediate with mercaptoethanol or N-acetyl cysteine and then converting an N-substituted maleimidyl group to a succinimide thioether was used.

The peak area ratio (%) of each chain to a total of peak area correction values was calculated according to the following expression.

$$\text{Light chain peak area ratio} = \frac{A_{Li}}{A_{L0} + A_{L1}} \times 100 \quad [\text{Expression 6}]$$

$$\text{Heavy chain peak area ratio} = \frac{A_{Hi}}{A_{H0} + A_{H1} + A_{H2} + A_{H3}} \times 100$$

Peak area correction value of each of $A_{Li}$, $A_{Hi}$: $L_i$, $H_i$

The average number of bound drugs per single antibody molecule in an antibody-drug conjugate composition was calculated according to the following expression.

The average number of bound drugs=($L_0$ peak area ratio×0+$L_1$ peak area ratio×1+$H_0$ peak area ratio×0+$H_1$ peak area ratio×1+$H_2$ peak area ratio×2+$H_3$ peak area ratio×3)/100×2

The concentration of the antibody was found to be 16.49 mg/mL, the yield of the antibody was found to be 290 mg (86%), and the average number of bound drugs (n) per single antibody molecule, which was measured by the common operation A, was found to be 4.4. The HPLC chromatograph representing the peak area ratio (%) of each chain is shown in FIG. 5.

[Common Operation B] Separation Method Involving Hydrophobic Column Chromatography for Antibody-Drug Conjugate Composition 1. HPLC Measurement Method An HPLC analysis was carried out under the following measurement conditions.

HPLC system: Shimadzu Science HPLC System
Detector: Ultraviolet absorption spectrometer (measurement wavelength: 280 nm)
Column: TSKgel Butyl-NPR (4.6×100 mm, 2.5 µm; TOSOH CORPORATION)
Column temperature: 30° C.
Mobile phase A: 25 mM Phosphate buffer (pH 7.0) aqueous solution comprising 1.5 M ammonium sulfate
Mobile phase B: Mixed solution comprising 75% of 25 mM phosphate buffer (pH 7.0) and 25% of isopropyl alcohol
Gradient program: 20%-60% (0 min-20 min), 20%-80% (20 min-20.1 min), 80%-80% (20.1 min-23 min), 80%-20% (23 min-23.1 min), 20%-20% (23.1 min-40 min)
Injected sample amount: 2 µL 2. Data Analysis Regarding the present data, since antibody-drug conjugates were eluted in the order of increasing the number of bound drugs based on a difference in the salt concentration because of the characteristics of the column, a distribution in the number of bonds was assumed by measuring individual area values. The peaks were D0 (an antibody not bound by any drug linker), D2, D4-1, D4-2, D6 and D8 in the order of elution, and the distribution conditions were the following: D0: 4.8%, D2: 16.8%, D4-1: 24.6%, D4-2: 13.1%, D6: 24.8%, and D8: 12.6% (FIG. 6).

(Example 3-2) Production of Humanized Anti-TROP2 Antibody (hTINA1-H1L1) ADC Composition According to the Method of the Present Invention (i) Reduction of Antibody A humanized anti-TROP2 antibody (hTINA1-H1L1) (22.9 mL: corresponding to 500 mg, concentration: 21.8 mg/mL; 25 mM histidine buffer) was placed in a glass reaction vessel, and further, a 25 mM histidine buffer (22 mL, pH 5.0) was added thereto. To the present reaction solution, a 0.5 M EDTA aqueous solution (0.0344 mL; 5 equivalents based on the antibody) was added, and thereafter, a 0.1 g/mL polysorbate 20 aqueous solution (0.050 mL; 0.01% based on the antibody) was added thereto. Thereafter, a 0.3 M disodium hydrogen phosphate aqueous solution was added to the reaction mixture, so that the mixture was adjusted to pH 7.12, and then, the mixture was cooled. Under stirring, a 1.00 mg/mL tris(2-carboxyethyl)phosphine hydrochloride aqueous solution (2.54 mL; 2.58 equivalents per single antibody molecule) was added to the reaction mixture at an internal temperature of 0° C. to 1° C., and the obtained mixture was then stirred for 6 hours at an internal temperature of 0° C. to 1° C., so that interchain disulfides of the antibody were reduced.

(ii) Conjugation of Antibody to Drug Linker Intermediate

A 6.03 mg/mL 50% acetone aqueous solution (2.99 mL; 5.1 equivalents per single antibody molecule) of the compound obtained in Example 2 was added to the solution obtained in the above (i) at an internal temperature of 0° C. to 2° C. under stirring over 10 minutes. The obtained mixture was stirred at the same temperature as described above for 40 minutes, so that the drug linker intermediate was allowed to bind to the antibody. Subsequently, a 50 mM N-acetylcysteine aqueous solution (0.206 mL; 3 equivalents per single antibody molecule) was added to the reaction mixture, and the thus obtained mixture was further stirred at the same temperature as described above for 10 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 700 mL, so that low molecular weight substances were removed. Thereafter, the remaining solution was concentrated to obtain 23.6 mL of a solution containing a humanized anti-TROP2 antibody (hTINA1-H1L1) ADC composition.

(iv) Evaluation of Properties

The average number of bound drugs was measured in the same manner as the common operation A described in Example 3-1, (iv). In the case of the humanized anti-TROP2 antibody (hTINA1-H1L1), based on its amino acid sequence, the number 27640 was used as an estimated value for the molar absorption coefficient of the light chain, and the number 83810 was used as an estimated value for the molar absorption coefficient of the heavy chain.

The concentration of the antibody was found to be 19.63 mg/mL, the yield of the antibody was found to be 463 mg (92%), and the average number of bound drugs (n) per single antibody molecule, which was measured by the common operation A, was found to be 4.1. The HPLC chromatograph representing the peak area ratio (%) of each chain is shown in FIG. 7.

The area value of the number of bound drugs was measured in the same manner as the common operation B described in Example 3-1, (iv). The distribution condition of the number of bound drugs was as follows: D0: 1.9%, D2: 19.5%, D4-1: 53.3%, D6: 18.5%, and D8: 5.5% (FIG. 8).

(v) Results

The average number of bound drugs in the humanized anti-TROP2 antibody ADC composition produced by the conventional method (Example 3-1) was 4.4, and the content of D4-1 therein was 24.6%. On the other hand, the average number of bound drugs in the humanized anti-TROP2 antibody ADC composition produced by the method of the present invention (Example 3-2) was 4.1, and the content of D4-1 therein was 53.3%.

(Example 4) Construction of Humanized Anti-CD98 Antibody Expression Vector and Production of Antibody (i) Construction of Humanized Anti-CD98 Antibody Heavy Chain (hM23-H1) Expression Vector A DNA fragment (nucleotide numbers 36 to 422) comprising a DNA sequence encoding the variable region of a humanized anti-CD98 antibody heavy chain (hM23-H1) that is represented by nucleotide numbers 58 to 405 in the nucleotide sequence of a humanized anti-CD98 antibody heavy chain (hM23-H1) shown in SEQ ID NO: 11 was synthesized (Artificial Gene Synthesis Service, GENEART). Using the synthesized DNA fragment as a template, a DNA fragment comprising a DNA sequence encoding the variable region of hM23-H1 was amplified with KOD-Plus- (TOYOBO) and the following primer set. Thereafter, an expression vector for chimeric and humanized antibody IgG1-type heavy chains, pCMA-G1, cleaved with the restriction enzyme BlpI, and the DNA fragment was then inserted into the cleaved site, using In-Fusion HD PCR cloning kit (CLONTECH), so as to construct a humanized anti-CD98 antibody heavy chain (hM23-H1) expression vector. The obtained expression vector was named "pCMA-G1/hM23-H1".

Primer Set:

```
                              (SEQ ID NO: 21: primer EG-Inf-F)
    5'-AGCTCCCAGATGGGTGCTGAGC-3'

(SEQ ID NO: 22: primer EG1-Inf-R)
    5'-GGGCCCTTGGTGGAGGCTGAGC-3'
```

(ii) Construction of Humanized Anti-CD98 Antibody Light Chain (hM23-L1) Expression Vector A DNA fragment (nucleotide numbers 38 to 420) comprising a DNA sequence encoding the variable region of a humanized anti-CD98 antibody light chain (hM23-L1) that is represented by nucleotide numbers 61 to 405 in the nucleotide sequence of a humanized anti-CD98 antibody light chain (hM23-L1) shown in SEQ ID NO: 13 was synthesized (Artificial Gene Synthesis Service, GENEART). Using the synthesized DNA fragment as a template, a DNA fragment comprising a DNA sequence encoding the variable region of a humanized anti-CD98 antibody light chain (hM23-L1) was amplified with KOD-Plus- (TOYOBO) and the following primer set. Thereafter, an expression vector for chimeric and humanized antibody light chains, pCMA-LK, was cleaved with the restriction enzyme BsiWI, and the DNA fragment was then inserted into the cleaved site, using In-Fusion HD PCR cloning kit (CLONTECH), so as to construct a humanized anti-CD98 antibody light chain (hM23-L1) expression vector. The obtained expression vector was named "pCMA-LK/hM23-L1".

Primer Set:

```
                              (SEQ ID NO: 23: primer CM-LKF)
    5'-CTGTGGATCTCCGGCGCGTACGGC-3'

(SEQ ID NO: 24: primer KCL-Inf-R)
    5'-GGAGGGGGCGGCCACCGTACG-3'
```

(iii) Production of Humanized Anti-CD98 Antibody (hM23-H1L1)

A humanized anti-CD98 antibody was produced by the same method as that applied in Example 1, (iii). A humanized anti-CD98 antibody obtained by the combination of pCMA-G1/hM23-H1 with pCMA-LK/hM23-L1 was named "hM23-H1L1".

(iv) Purification of Humanized Anti-CD98 Antibody (hM23-H1L1)

An antibody was purified from the culture supernatant obtained in the above (iii) by the same method as that applied in Example 1, (iv).

(v) Buffer Exchange for Humanized Anti-CD98 Antibody (hM23-H1L1) and Adjustment of Concentration The humanized anti-CD98 antibody (hM23-H1L1) purified in the above (iv) was subjected to the exchange of the buffer and the adjustment of the concentration thereof by the same method as that applied in Example 1, (v). During the operation, the concentration of the antibody was measured using a 280 nm absorption coefficient (1.65 mLmg$^{-1}$ cm$^{-1}$), and thereafter, the antibody concentration was adjusted to 40 mg/mL using PBS6.0/EDTA.

(Example 5) Production of Humanized Anti-CD98 Antibody ADC Composition (Example 5-1) Production of Humanized Anti-CD98 Antibody (hM23-H1L1) ADC Composition According to Conventional Method (i) Reduction of Antibody A humanized anti-CD98 antibody (hM23-H1L1) (12 mL: corresponding to 480 mg, concentration: 40 mg/mL; 25 mM histidine buffer) was placed in a glass reaction vessel, and further, a 25 mM histidine buffer (36 mL, pH 5.0) was added thereto. To the present reaction solution, a 0.5 M EDTA aqueous solution (CALBIOCHEM; 0.0394 mL; 6 equivalents based on the antibody) was added, and thereafter, a 0.1 g/mL polysorbate 20 (NOF CORPORATION) aqueous solution (0.048 mL; 0.01% based on the antibody) was added thereto. Thereafter, a 0.3 M disodium hydrogen phosphate aqueous solution was added to the reaction mixture, so that the mixture was adjusted to pH 7.10. Under stirring at 21° C., a 1.00 mg/mL tris(2-carboxyethyl)phosphine hydrochloride (Nacalai Tesque, Inc.) aqueous solution (2.17 mL; 2.31 equivalents per single antibody molecule) was added to the reaction mixture, and the obtained mixture was then heated for 3 hours to result in an internal temperature of 35° C. to 36° C., so that interchain disulfides of the antibody were reduced.

(ii) Conjugation of Antibody to Drug Linker Intermediate

The solution obtained in the above (i) was cooled, and a 6.20 mg/mL 50% acetone aqueous solution (2.74 mL; 5.2 equivalents per single antibody molecule) of the compound obtained in Example 2 was then added to the reaction solution at an internal temperature of 17° C. to 18° C. under stirring over 7 minutes. The obtained mixture was stirred at the same temperature as described above for 40 minutes, so that the drug linker intermediate was allowed to bind to the antibody. Subsequently, a 50 mM N-acetylcysteine (Kishida Chemical Co., Ltd.) aqueous solution (0.197 mL; 3 equivalents per single antibody molecule) was added to the reaction mixture, and the thus obtained mixture was further stirred at the same temperature as described above for 30 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 600 mL, so that low molecular weight substances were removed. Thereafter, the remaining solution was concentrated to obtain 21.6 mL of a solution containing a humanized anti-CD98 antibody (hM23-H1L1) ADC composition.

(iv) Evaluation of Properties

The average number of bound drugs was measured in the same manner as the common operation A described in Example 3-1, (iv). In the case of the humanized anti-CD98 antibody (hM23-H1L1), based on its amino acid sequence, the number 41370 was used as an estimated value for the molar absorption coefficient of the light chain, and the number 77810 was used as an estimated value for the molar absorption coefficient of the heavy chain.

The concentration of the antibody was found to be 20.8 mg/mL, the yield of the antibody was found to be 449 mg (91%), and the average number of bound drugs (n) per single antibody molecule, which was measured by the common operation A, was found to be 4.0. The HPLC chromatograph representing the peak area ratio (%) of each chain is shown in FIG. 9.

The area value of the number of bound drugs was measured in the same manner as the common operation B described in Example 3-1, (iv). The distribution condition of the number of bound drugs was as follows: D0: 4.2%, D2: 24.2%, D4-1: 27.8%, D4-2: 13.3%, D6: 20.8%, and D8: 7.6% (FIG. 10).

(Example 5-2) Production of Humanized Anti-CD98 Antibody (hM23-H1L1) ADC Composition According to the Method of the Present Invention (i) Reduction of Antibody A humanized anti-CD98 antibody (hM23-H1L1) (12.5 mL: corresponding to 500 mg, concentration: 40 mg/mL; 25 mM histidine buffer) was placed in a glass reaction vessel, and further, a 25 mM histidine buffer (27.5 mL, pH 5.0) was added thereto. To the present reaction solution, a 0.5 M EDTA aqueous solution (CALBIOCHEM; 0.041 mL; 6 equivalents based on the antibody) was added, and thereafter, a 0.1 g/mL polysorbate 20 (NOF CORPORATION) aqueous solution (0.050 mL; 0.01% based on the antibody) was added thereto. Thereafter, a 0.3 M disodium hydrogen phosphate aqueous solution was added to the reaction mixture, so that the mixture was adjusted to pH 7.10. The reaction solution was cooled, and under stirring at an internal temperature of 0° C. to 1° C., a 1.00 mg/mL tris(2-carboxyethyl)phosphine hydrochloride (Nacalai Tesque, Inc.) aqueous solution (2.75 mL; 2.80 equivalents per single antibody molecule) was added to the reaction mixture, and the obtained mixture was then stirred for 6 hours to result in an internal temperature of 0° C. to 1° C., so that interchain disulfides of the antibody were reduced.

(ii) Conjugation of Antibody to Drug Linker Intermediate

A 6.08 mg/mL 50% acetone aqueous solution (3.14 mL; 5.4 equivalents per single antibody molecule) of the compound obtained in Example 2 was added to the solution obtained in the above (i) at an internal temperature of 0.7° C. to 1.2° C. under stirring over 10 minutes. The obtained mixture was stirred at the same temperature as described above for 50 minutes, so that the drug linker intermediate was allowed to bind to the antibody. Subsequently, a 50 mM N-acetylcysteine (Kishida Chemical Co., Ltd.) aqueous solution (0.205 mL; 3 equivalents per single antibody molecule) was added to the reaction mixture, and the thus obtained mixture was further stirred at the same temperature as described above for 30 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 600 mL, so that low molecular weight substances were removed. Thereafter, the remaining solution was concentrated to obtain 23.6 mL of a solution containing a humanized anti-CD98 antibody (hM23-H1L1) ADC composition.

(iv) Evaluation of Properties

The average number of bound drugs was measured in the same manner as the common operation A described in Example 3-1, (iv). In the case of the humanized anti-CD98 antibody (hM23-H1L1), based on its amino acid sequence, the number 41370 was used as an estimated value for the molar absorption coefficient of the light chain, and the number 77810 was used as an estimated value for the molar absorption coefficient of the heavy chain.

The concentration of the antibody was found to be 19.91 mg/mL, the yield of the antibody was found to be 470 mg (94%), and the average number of bound drugs (n) per single antibody molecule, which was measured by the common operation A, was found to be 4.1. The HPLC chromatograph representing the peak area ratio (%) of each chain is shown in FIG. 11.

The area value of the number of bound drugs was measured in the same manner as the common operation B described in Example 3-1, (iv). The distribution condition of the number of bound drugs was as follows: D0: 2.2%, D2: 18.1%, D4-1: 51.0%, D6: 20.6%, and D8: 7.6% (FIG. 12).

(v) Results

The average number of bound drugs in the humanized anti-CD98 antibody ADC composition produced by the conventional method (Example 5-1) was 4.0, and the content of D4-1 therein was 27.8%. On the other hand, the average number of bound drugs in the humanized anti-CD98 antibody ADC composition produced by the method of the present invention (Example 5-2) was 4.1, and the content of D4-1 therein was 51.0%.

(Example 6) Production of Humanized Anti-B7-H3 Antibody ADC Composition (Example 6-1) Production of Humanized Anti-B7-H3 Antibody (M30-H1-L4) ADC Composition According to Conventional Method (i) Reduction of Antibody A humanized anti-B7-H3 antibody (M30-H1-L4) (produced according to the method described in Reference Example 1 of WO2014/057687, 12.4 mL: corresponding to 250 mg, concentration: 20.1 mg/mL; 25 mM citrate buffer) was placed in a glass reaction vessel, and a 25 mM histidine buffer (18 mL, pH 7.5) was further added thereto. To the present reaction solution, a 0.5 M EDTA aqueous solution (CALBIOCHEM; 0.018 mL; 5 equivalents based on the antibody) was added, and thereafter, a 0.1 g/mL polysorbate 80 (NOF CORPORATION) aqueous solution (0.013 mL; 0.01% based on the antibody) was added thereto. Thereafter, a 0.3 M disodium hydrogen phosphate aqueous solution was added to the reaction mixture, so that the mixture was adjusted to pH 7.02. Under stirring at 35° C., a 1.00 mg/mL tris(2-carboxyethyl)phosphine hydrochloride (Nacalai Tesque, Inc.) aqueous solution (1.05 mL; 2.15 equivalents per single antibody molecule) was added to the reaction mixture, and the obtained mixture was then heated for 2 hours to result in an internal temperature of 35° C. to 36° C., so that interchain disulfides of the antibody were reduced.

(ii) Conjugation of Antibody to Drug Linker Intermediate

The solution obtained in the above (i) was cooled, and a 6.22 mg/mL 50% acetone aqueous solution (1.36 mL; 4.8 equivalents per single antibody molecule) of the compound obtained in Example 2 was then added to the reaction solution at an internal temperature of 15° C. to 16° C. under stirring over 4 minutes. The obtained mixture was stirred at the same temperature as described above for 20 minutes, so that the drug linker intermediate was allowed to bind to the antibody. Subsequently, a 50 mM N-acetylcysteine (Kishida Chemical Co., Ltd.) aqueous solution (0.102 mL; 3 equivalents per single antibody molecule) was added to the reaction mixture, and the thus obtained mixture was further stirred at the same temperature as described above for 20 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 300 mL, so that low molecular weight substances were removed. Thereafter, the remaining solution was concentrated to obtain 13.1 mL of a solution containing a humanized anti-B7-H3 antibody (M30-H1-L4) ADC composition.

(iv) Evaluation of Properties

The average number of bound drugs was measured in the same manner as the common operation A described in Example 3-1, (iv). In the case of the humanized anti-B7-H3 antibody (M30-H1-L4), based on its amino acid sequence, the number 30160 was used as an estimated value for the molar absorption coefficient of the light chain, and the number 87250 was used as an estimated value for the molar absorption coefficient of the heavy chain.

The concentration of the antibody was found to be 18.4 mg/mL, the yield of the antibody was found to be 241 mg (94%), and the average number of bound drugs (n) per single antibody molecule, which was measured by the common operation A, was found to be 3.8. The HPLC chromatograph representing the peak area ratio (%) of each chain is shown in FIG. 15.

The area value of the number of bound drugs was measured in the same manner as the common operation B described in Example 3-1, (iv). The distribution condition of the number of bound drugs was as follows: D0: 6.5%, D2: 30.5%, D4-1: 27.9%, D4-2: 12.3%, D6: 17.7%, and D8: 4.9% (FIG. 16).

(Example 6-2) Production of Humanized Anti-B7-H3 Antibody (M30-H1-L4) ADC Composition According to the Method of the Present Invention (i) Reduction of Antibody A humanized anti-B7-H3 antibody (M30-H1-L4) (produced according to the method described in Reference Example 1 of WO2014/057687, 27.1 mL: corresponding to 500 mg, concentration: 18.5 mg/mL; 10 mM histidine buffer) was placed in a glass reaction vessel, and further, a 10 mM histidine aqueous solution (25 mL) was added thereto. To the present reaction solution, sucrose (MERCK; 1.25 g) and a 0.5 M EDTA aqueous solution (CALBIOCHEM; 0.041 mL; 6 equivalents based on the antibody)

were added, and thereafter, a 0.1 g/mL polysorbate 80 (NOF CORPORATION) aqueous solution (0.050 mL; 0.01% based on the antibody) was added thereto. Thereafter, a 0.3 M disodium hydrogen phosphate aqueous solution was added to the reaction mixture, so that the mixture was adjusted to pH 7.08. The reaction solution was cooled, and under stirring at an internal temperature of 0° C. to 1° C., a 1.00 mg/mL tris(2-carboxyethyl)phosphine hydrochloride (Nacalai Tesque, Inc.) aqueous solution (2.08 mL; 2.13 equivalents per single antibody molecule) was added to the reaction mixture, and the obtained mixture was then stirred for 5.5 hours to result in an internal temperature of 0° C. to 1° C., so that interchain disulfides of the antibody were reduced.

(ii) Conjugation of Antibody to Drug Linker Intermediate

A 6.04 mg/mL 50% acetone aqueous solution (2.82 mL; 4.8 equivalents per single antibody molecule) of the compound obtained in Example 2 was added to the solution obtained in the above (i) at an internal temperature of 0° C. to 1° C. under stirring over 20 minutes. The obtained mixture was stirred at the same temperature as described above for 20 minutes, so that the drug linker intermediate was allowed to bind to the antibody. Subsequently, a 50 mM N-acetylcysteine (Kishida Chemical Co., Ltd.) aqueous solution (0.205 mL; 3 equivalents per single antibody molecule) was added to the reaction mixture, and the thus obtained mixture was further stirred at the same temperature as described above for 20 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 800 mL, so that low molecular weight substances were removed. Thereafter, the remaining solution was concentrated to obtain 23.6 mL of a solution containing a humanized anti-B7-H3 antibody (M30-H1-L4) ADC composition.

(iv) Evaluation of Properties

The average number of bound drugs was measured in the same manner as the common operation A described in Example 3-1, (iv). In the case of the humanized anti-B7-H3 antibody (M30-H1-L4), based on its amino acid sequence, the number 30160 was used as an estimated value for the molar absorption coefficient of the light chain, and the number 87250 was used as an estimated value for the molar absorption coefficient of the heavy chain.

The concentration of the antibody was found to be 19.4 mg/mL, the yield of the antibody was found to be 455 mg (89%), and the average number of bound drugs (n) per single antibody molecule, which was measured by the common operation A, was found to be 4.1. The HPLC chromatograph representing the peak area ratio (%) of each chain is shown in FIG. 17.

The area value of the number of bound drugs was measured in the same manner as the common operation B described in Example 3-1, (iv). The distribution condition of the number of bound drugs was as follows: D0: 2.7%, D2: 22.3%, D4-1: 58.4%, D6: 14.1%, and D8: 2.4% (FIG. 18).

(v) Results

The average number of bound drugs in the humanized anti-B7-H3 antibody ADC composition produced by the conventional method (Example 6-1) was 3.8, and the content of D4-1 therein was 27.9%. On the other hand, the average number of bound drugs in the humanized anti-B7-H3 antibody ADC composition produced by the method of the present invention (Example 6-2) was 4.1, and the content of D4-1 therein was 58.4%.

(Example 7) Production of Humanized Anti-HER2 Antibody ADC Composition (Example 7-1) Production of Humanized Anti-HER2 Antibody ADC Composition According to Conventional Method (i) Reduction of Antibody A humanized anti-HER2 antibody (trastuzumab; U.S. Pat. No. 5,821,337) (22.3 mL: corresponding to 500 mg, concentration: 22.4 mg/mL; 25 mM histidine buffer) was placed in a glass reaction vessel, and a 25 mM histidine buffer (27 mL, pH 5.0) was further added thereto. To the present reaction solution, a 0.5 M EDTA aqueous solution (0.034 mL; 5 equivalents based on the antibody) was added, and thereafter, a 0.1 g/mL polysorbate 20 aqueous solution (0.050 mL; 0.01% based on the antibody) was added thereto. Thereafter, a 0.3 M disodium hydrogen phosphate aqueous solution was added to the reaction mixture, so that the mixture was adjusted to pH 7.12. Under stirring at 22° C., a 1.00 mg/mL tris(2-carboxyethyl)phosphine hydrochloride aqueous solution (2.12 mL; 2.15 equivalents per single antibody molecule) was added to the reaction mixture, and the obtained mixture was then stirred for 3 hours to result in an internal temperature of 22° C. to 25° C., so that interchain disulfides of the antibody were reduced.

(ii) Conjugation of Antibody to Drug Linker Intermediate

The solution obtained in the above (i) was cooled, and a 6.15 mg/mL 50% acetone aqueous solution (2.77 mL; 4.8 equivalents per single antibody molecule) of the compound obtained in Example 2 was then added to the reaction solution at an internal temperature of 11° C. to 13° C. under stirring over 20 minutes. The obtained mixture was stirred at the same temperature as described above for 20 minutes, so that the drug linker intermediate was allowed to bind to the antibody. Subsequently, a 50 mM N-acetylcysteine aqueous solution (0.206 mL; 3 equivalents per single antibody molecule) was added to the reaction mixture, and the thus obtained mixture was further stirred at the same temperature as described above for 20 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 600 mL, so that low molecular weight substances were removed. Thereafter, the remaining solution was concentrated to obtain 22.7 mL of a solution containing a humanized anti-HER2 antibody ADC composition.

(iv) Evaluation of Properties

The average number of bound drugs was measured in the same manner as the common operation A described in Example 3-1, (iv). In the case of the humanized anti-HER2 antibody (trastuzumab), based on its amino acid sequence, the number 26150 was used as an estimated value for the molar absorption coefficient of the light chain, and the number 81290 was used as an estimated value for the molar absorption coefficient of the heavy chain.

The concentration of the antibody was found to be 20.39 mg/mL, the yield of the antibody was found to be 462 mg (90%), and the average number of bound drugs (n) per single antibody molecule, which was measured by the common operation A, was found to be 3.9. The HPLC chromatograph representing the peak area ratio (%) of each chain is shown in FIG. 21.

The area value of the number of bound drugs was measured in the same manner as the common operation B described in Example 3-1, (iv). The distribution condition of the number of bound drugs was as follows: D0: 3.6%, D2: 26.1%, D4-1: 34.1%, D4-2: 13.6%, D6: 17.6%, and D8: 5.0% (FIG. 22).

(Example 7-2) Production of Humanized Anti-HER2 Antibody ADC Composition According to the Method of the Present Invention (i) Reduction of Antibody A humanized anti-HER2 antibody (trastuzumab; U.S. Pat. No. 5,821,337) (22.3 mL: corresponding to 500 mg, concentration: 22.4 mg/mL; 25 mM histidine buffer) was placed in a glass reaction vessel, and a 25 mM histidine buffer (25 mL, pH 5.0) was further added thereto. To the present reaction solution, a 0.5 M EDTA aqueous solution (0.034 mL; 5 equivalents based on the antibody) was added, and thereafter, a 0.1 g/mL polysorbate 20 aqueous solution (0.050 mL; 0.01% based on the antibody) was added thereto. Thereafter, a 0.3 M disodium hydrogen phosphate aqueous solution was added to the reaction mixture, so that the mixture was adjusted to pH 7.13, and then the mixture was cooled. Under stirring, a 1.00 mg/mL tris(2-carboxyethyl) phosphine hydrochloride aqueous solution (2.37 mL; 2.40 equivalents per single antibody molecule) was added to the reaction mixture at an internal temperature of 0° C. to 1° C., and the obtained mixture was then stirred at an internal temperature of 0° C. to 1° C. for 6 hours, so that interchain disulfides of the antibody were reduced.

(ii) Conjugation of Antibody to Drug Linker Intermediate

A 6.14 mg/mL 50% acetone aqueous solution (2.84 mL; 4.9 equivalents per single antibody molecule) of the compound obtained in Example 2 was added to the solution obtained in the above (i) at an internal temperature of 0° C. to 2° C. under stirring over 10 minutes. The obtained mixture was stirred at the same temperature as described above for 40 minutes, so that the drug linker intermediate was allowed to bind to the antibody. Subsequently, a 50 mM N-acetylcysteine aqueous solution (0.206 mL; 3 equivalents per single antibody molecule) was added to the reaction mixture, and the thus obtained mixture was further stirred at the same temperature as described above for 50 minutes. The reaction of the drug linker intermediate was terminated, and the pH of the reaction mixture was then adjusted to pH 5.0 using a 10% acetic acid aqueous solution.

(iii) Purification

Employing Pellicon XL (Millipore Japan, 50 cm$^2$), the solution obtained in the above (ii) was circulated, while a 10 mM histidine buffer (pH 5.0) was added thereto using a roller pump, and a washing operation was carried out until the amount of water discharged became 600 mL, so that low molecular weight substances were removed. Thereafter, the remaining solution was concentrated to obtain 21.7 mL of a solution containing a humanized anti-HER2 antibody ADC composition.

(iv) Evaluation of Properties

The average number of bound drugs was measured in the same manner as the common operation A described in Example 3-1, (iv). In the case of the humanized anti-HER2 antibody (trastuzumab), based on its amino acid sequence, the number 26150 was used as an estimated value for the molar absorption coefficient of the light chain, and the number 81290 was used as an estimated value for the molar absorption coefficient of the heavy chain.

The concentration of the antibody was found to be 21.2 mg/mL, the yield of the antibody was found to be 459 mg (89%), and the average number of bound drugs (n) per single antibody molecule, which was measured by the common operation A, was found to be 4.0. The HPLC chromatograph representing the peak area ratio (%) of each chain is shown in FIG. 23.

The area value of the number of bound drugs was measured in the same manner as the common operation B described in Example 3-1, (iv). The distribution condition of the number of bound drugs was as follows: D0: 2.8%, D2: 23.8%, D4-1: 55.2%, D6: 15.0%, and D8: 3.3% (FIG. 24).

(v) Results

The average number of bound drugs in the humanized anti-HER2 antibody ADC composition produced by the conventional method (Example 7-1) was 3.9, and the content of D4-1 therein was 34.1%. On the other hand, the average number of bound drugs in the humanized anti-HER2 antibody ADC composition produced by the method of the present invention (Example 7-2) was 4.0, and the content of D4-1 therein was 55.2%.

(Test Example 1) Therapeutic Efficacy of Antibody-Drug Conjugate Composition

Mice: 5- to 6-week-old female BALB/c-nu/nu mice (Charles River Laboratories International, Inc.) were acclimatized under SPF conditions for 4 to 7 days, before the use for experiments. The mice were fed with a sterilized solid feed (FR-2, Funabashi Farms Co., Ltd) and sterilized tap water (prepared by adding a 5-15 ppm sodium hypochlorite solution to tap water).

Measurement and calculation expression: The major axis and minor axis of a tumor were measured two or more times a week, using electronic digital calipers (CD-15C, Mitutoyo Corp.), and the volume (mm$^3$) of the tumor was then calculated. The applied calculation expression is as follows.

$$\text{Tumor volume (mm}^3\text{)} = \tfrac{1}{2} \times \text{major axis (mm)} \times [\text{minor axis (mm)}]^2$$

A human pancreatic adenocarcinoma cell line CFPAC-1 ($4 \times 10^6$ cells), which had been purchased from ATCC, was suspended in a normal saline. Thereafter, the obtained solution was subcutaneously implanted into the female BALB/c-nu/nu mice (Day 0), and the mice were then randomly divided into groups on Day 11. After completion of the grouping, the humanized anti-TROP2 antibody ADC composition produced according to the conventional method (Example 3-1) and the humanized anti-TROP2 antibody ADC composition produced according to the method of the present invention (Example 3-2) were each administered to the mice, via caudal vein, at a dose of 0.3 mg/kg, 1 mg/kg, or 3 mg/kg. The antibody-drug conjugate compositions were all diluted with Acetate-Buffered Saline (pH 5.5) (Nacalai Tesque, Inc.), and thereafter, the obtained solution was then administered in a liquid amount of 10 mL/kg to each mouse. The therapeutic efficacy was determined, using the minimum dose capable of regression of the tumor volume (regression dose) as an indicator. The regression dose of the humanized anti-TROP2 antibody ADC composition produced by the conventional method was 1 mg/kg, whereas the regression dose of the humanized anti-TROP2 antibody ADC composition produced by the method of the present invention was also 1 mg/kg (FIG. 19). Thus, it was demonstrated that the antibody-drug conjugate composition produced by the production method of the present invention has therapeutic efficacy equivalent to that of the antibody-drug conjugate composition produced by the conventional production method.

(Test Example 2) Safety of Antibody-Drug Conjugate Composition

The humanized anti-TROP2 antibody ADC composition produced according to the conventional method (Example 3-1) and the humanized anti-TROP2 antibody ADC composition produced according to the method of the present invention (Example 3-2) were each administered to cynomolgus monkeys of cross-species at intervals of once per three weeks, a total of three times. The monkeys were observed until the day following the final administration, and the maximum dose that did not provide severe toxicity (HNSTD) was analyzed. As a result, the HNSTD of the humanized anti-TROP2 antibody ADC composition produced by the conventional method was 10 mg/kg, whereas the HNSTD of the humanized anti-TROP2 antibody ADC composition produced by the method of the present invention was 30 mg/kg. Hence, it was demonstrated that the antibody-drug conjugate composition produced by the production method of the present invention has safety that is more excellent than that of the antibody-drug conjugate composition produced by the conventional production method.
(Consideration 1)

From the results of Examples 3, 4, 6 and 7, the average number of bound drugs in the antibody-drug conjugate composition produced by the conventional production method, and the average number of bound drugs in the antibody-drug conjugate composition produced by the production method of the present invention, were both found to be 3.5 to 4.5. On the other hand, the content of antibody-drug conjugates in which four drug linkers are bound to heavy-light interchain thiols, in the antibody-drug conjugate composition produced by the conventional production method was 35% or less, whereas the same content as described above in the antibody-drug conjugate composition produced by the production method of the present invention was 50% or more. As such, it was demonstrated that an antibody-drug conjugate composition wherein the average number of bound drugs is 3.5 to 4.5, and the content of antibody-drug conjugates in which four drug linkers are bound to heavy-light interchain thiols is 50% or more, can be selectively produced by using the production method of the present invention.
(Consideration 2)

From the results of Test Example 2, it was demonstrated that the antibody-drug conjugate composition produced by the production method of the present invention has safety that is more excellent than that of the antibody-drug conjugate composition produced by the conventional production method.

From the aforementioned results, it was demonstrated that the antibody-drug conjugate composition of the present invention (an antibody-drug conjugate composition wherein the average number of bound drugs is 3.5 to 4.5, and the content of antibody-drug conjugates in which four drug linkers are bound to heavy-light interchain thiols is 50% or more) has safety that is more excellent than that of the antibody-drug conjugate composition produced by the conventional production method (an antibody-drug conjugate composition wherein the average number of bound drugs is 3.5 to 4.5, and the content of antibody-drug conjugates in which four drug linkers are bound to heavy-light interchain thiols is 35% or less).

Sequence Listing Free Text
SEQ ID NO: 1: The nucleotide sequence of humanized anti-TROP2 antibody heavy chain (hTINA1-H1)
SEQ ID NO: 2: The amino acid sequence of humanized anti-TROP2 antibody heavy chain (hTINA1-H1)
SEQ ID NO: 3: The nucleotide sequence of humanized anti-TROP2 antibody light chain (hTINA1-L1)
SEQ ID NO: 4: The amino acid sequence of humanized anti-TROP2 antibody light chain (hTINA1-L1)
SEQ ID NO: 5: The amino acid sequence of anti-TROP2 antibody (TINA1) CDRH1
SEQ ID NO: 6: The amino acid sequence of anti-TROP2 antibody (TINA1) CDRH2
SEQ ID NO: 7: The amino acid sequence of anti-TROP2 antibody (TINA1) CDRH3
SEQ ID NO: 8: The amino acid sequence of anti-TROP2 antibody (TINA1) CDRL1
SEQ ID NO: 9: The amino acid sequence of anti-TROP2 antibody (TINA1) CDRL2
SEQ ID NO: 10: The amino acid sequence of anti-TROP2 antibody (TINA1) CDRL3
SEQ ID NO: 11: The nucleotide sequence of humanized anti-CD98 antibody heavy chain (hM23-H1)
SEQ ID NO: 12: The amino acid sequence of humanized anti-CD98 antibody heavy chain (hM23-H1)
SEQ ID NO: 13: The nucleotide sequence of humanized anti-CD98 antibody light chain (hM23-L1)
SEQ ID NO: 14: The amino acid sequence of humanized anti-CD98 antibody light chain (hM23-L1)
SEQ ID NO: 15: The amino acid sequence of anti-CD98 antibody (M23) CDRH1
SEQ ID NO: 16: The amino acid sequence of anti-CD98 antibody (M23) CDRH2
SEQ ID NO: 17: The amino acid sequence of anti-CD98 antibody (M23) CDRH3
SEQ ID NO: 18: The amino acid sequence of anti-CD98 antibody (M23) CDRL1
SEQ ID NO: 19: The amino acid sequence of anti-CD98 antibody (M23) CDRL2
SEQ ID NO: 20: The amino acid sequence of anti-CD98 antibody (M23) CDRL3
SEQ ID NO: 21: The nucleotide sequence of primer EG-Inf-F
SEQ ID NO: 22: The nucleotide sequence of primer EG1-Inf-R
SEQ ID NO: 23: The nucleotide sequence of primer CM-LKF
SEQ ID NO: 24: The nucleotide sequence of primer KCL-Inf-R
SEQ ID NO: 25: The amino acid sequence of humanized anti-B7-H3 antibody heavy chain (M30-H1)
SEQ ID NO: 26: The amino acid sequence of humanized anti-B7-H3 antibody light chain (M30-L4)
SEQ ID NO: 27: The amino acid sequence of anti-B7-H3 antibody (M30) CDRH1
SEQ ID NO: 28: The amino acid sequence of anti-B7-H3 antibody (M30) CDRH2
SEQ ID NO: 29: The amino acid sequence of anti-B7-H3 antibody (M30) CDRH3
SEQ ID NO: 30: The amino acid sequence of anti-B7-H3 antibody (M30) CDRL1

SEQ ID NO: 31: The amino acid sequence of anti-B7-H3 antibody (M30) CDRL2
SEQ ID NO: 32: The amino acid sequence of anti-B7-H3 antibody (M30) CDRL3
SEQ ID NO: 33: The amino acid sequence of humanized anti-HER2 antibody heavy chain
SEQ ID NO: 34: The amino acid sequence of humanized anti-HER2 antibody light chain

The invention claimed is:

1. A method for producing an antibody-drug conjugate composition, comprising:
   (i) a step of reacting an antibody with a reducing agent in a buffer to reduce interchain disulfides, wherein the buffer comprises a chelating agent; and
   (ii) a step of reacting drug linker intermediates with the antibody having thiol groups obtained in the step (i), wherein
   the reaction temperature in the step (i) is −10° C. to 10° C., and
   the average number of bound drugs in the produced antibody-drug conjugate composition is 3.5 to 4.5, and the content of the antibody-drug conjugates in which four drug linkers are bound to heavy-light interchain thiols, in the produced antibody-drug conjugate composition is 50% or more.

2. The production method according to claim 1, wherein the average number of bound drugs in the produced antibody-drug conjugate composition is 4.0 to 4.1.

3. The production method according to claim 1, wherein the reaction temperature in the step (i) is −5° C. to 5° C.

4. The production method according to claim 3, wherein the reaction temperature in the step (i) is −3° C. to 3° C.

5. The production method according to claim 4, wherein the reaction temperature in the step (i) is 0° C. to 2° C.

6. The production method according to claim 5, wherein the reaction temperature in the step (i) is 0° C. to 1° C.

7. The production method according to claim 1, wherein the reducing agent is used in an amount of 2 to 3 molar equivalents per molecule of the antibody.

8. The production method according to claim 1, wherein the reducing agent is tris(2-carboxyethyl)phosphine or a salt thereof.

9. The production method according to claim 8, wherein the salt of tris(2-carboxyethyl)phosphine is tris(2-carboxyethyl)phosphine hydrochloride.

10. The production method according to claim 1, wherein the buffer is a histidine buffer.

11. The production method according to claim 1, wherein the chelating agent is ethylenediaminetetraacetic acid.

12. The production method according to claim 1, wherein the antibody is an anti-TROP2 antibody, an anti-CD98 antibody, an anti-B7-H3 antibody, or an anti-HER2 antibody.

13. The production method according to claim 1, wherein the drug linker intermediate has an N-substituted maleimidyl group.

14. The production method according to claim 13, wherein
the drug linker intermediate is (SEQ ID NO: 35)

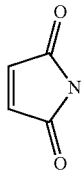 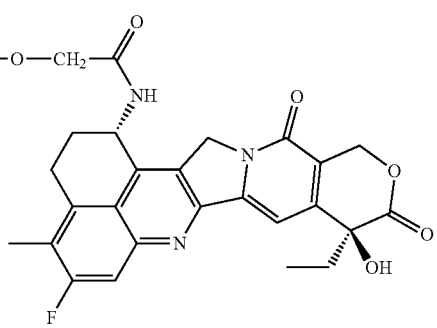

(SEQ ID NO: 35)

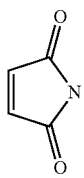 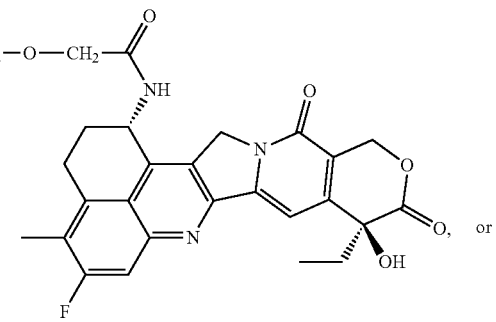

, or (SEQ ID NO: 35)

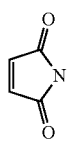 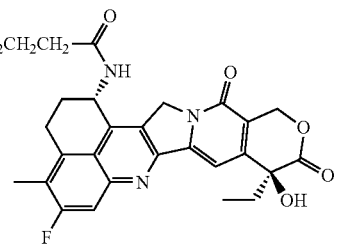

wherein -GGFG- (SEQ ID NO: 35) represents a tetrapeptide residue consisting of glycine-glycine-phenylalanine-glycine.

15. The production method according to claim 12, wherein the antibody is an anti-TROP2 antibody.

16. The production method according to claim 15, wherein the anti-TROP2 antibody retains CDRH1 consisting of the amino acid sequence shown in SEQ ID NO: 5 (TAGMQ), CDRH2 consisting of the amino acid sequence shown in SEQ ID NO: 6 (WINTHSGVPKYAEDFKG), CDRH3 consisting of the amino acid sequence shown in SEQ ID NO: 7 (SGFGSSYWYFDV), CDRL1 consisting of the amino acid sequence shown in SEQ ID NO: 8 (KASQDVSTAVA), CDRL2 consisting of the amino acid sequence shown in SEQ ID NO: 9 (SASYRYT), and CDRL3 consisting of the amino acid sequence shown in SEQ ID NO: 10 (QQHYITPLT).

17. The production method according to claim 15, wherein the anti-TROP2 antibody consists of a heavy chain consisting of an amino acid sequence consisting of amino acid residues at positions 20 to 470 of SEQ ID NO: 2, and a light chain consisting of an amino acid sequence consisting of amino acid residues at positions 21 to 234 of SEQ ID NO: 4.

18. The production method according to claim 15, wherein the anti-TROP2 antibody consists of a heavy chain consisting of an amino acid sequence consisting of amino acid residues at positions 20 to 469 of SEQ ID NO: 2, and a light chain consisting of an amino acid sequence consisting of amino acid residues at positions 21 to 234 of SEQ ID NO: 4.

19. The production method according to claim 12, wherein the antibody is an anti-B7-H3 antibody.

20. The production method according to claim 19, wherein the anti-B7-H3 antibody retains CDRH1 consisting of the amino acid sequence shown in SEQ ID NO: 27 (NYVMH), CDRH2 consisting of the amino acid sequence shown in SEQ ID NO: 28 (YINPYNDDVKYNEKFKG), CDRH3 consisting of the amino acid sequence shown in SEQ ID NO: 29 (WGYYGSPLYYFDY), CDRL1 consisting of the amino acid sequence shown in SEQ ID NO: 30 (RASSRLIYMH), CDRL2 consisting of the amino acid sequence shown in SEQ ID NO: 31 (ATSNLAS), and CDRL3 consisting of the amino acid sequence shown in SEQ ID NO: 32 (QQWNSNPPT).

21. The production method according to claim 19, wherein the anti-B7-H3 antibody consists of a heavy chain consisting of an amino acid sequence consisting of amino acid residues at positions 20 to 471 of SEQ ID NO: 25, and a light chain consisting of an amino acid sequence consisting of amino acid residues at positions 21 to 233 of SEQ ID NO: 26.

22. The production method according to claim 19, wherein the anti-B7-H3 antibody consists of a heavy chain consisting of an amino acid sequence consisting of amino acid residues at positions 20 to 470 of SEQ ID NO: 25, and a light chain consisting of an amino acid sequence consisting of amino acid residues at positions 21 to 233 of SEQ ID NO: 26.

23. The production method according to claim 12, wherein the antibody is an anti-HER2 antibody.

24. The production method according to claim 23, wherein the anti-HER2 antibody consists of a heavy chain consisting of an amino acid sequence consisting of amino acid residues at positions 1 to 449 of SEQ ID NO: 33, and a light chain consisting of an amino acid sequence consisting of amino acid residues at positions 1 to 214 of SEQ ID NO: 34.

25. The production method according to claim 23, wherein the anti-HER2 antibody consists of a heavy chain consisting of an amino acid sequence shown in SEQ ID NO: 33, and a light chain consisting of an amino acid sequence shown in SEQ ID NO: 34.

26. The production method according to claim 14, wherein the drug linker intermediate is (SEQ ID NO: 35)

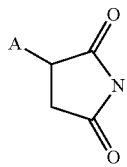
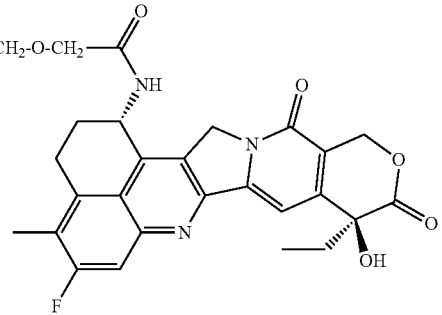

wherein -GGFG- (SEQ ID NO: 35) represents a tetrapeptide residue consisting of glycine-glycine-phenylalanine-glycine.

* * * * *

SEQUENCE LISTING

```
<160> NUMBER OF SEQ ID NOS: 35

<210> SEQ ID NO 1
<211> LENGTH: 1410
<212> TYPE: DNA
<213> ORGANISM: Artificial Sequence
<220> FEATURE:
<223> OTHER INFORMATION: hTINA1-H1
<220> FEATURE:
<221> NAME/KEY: CDS
<222> LOCATION: (1)..(1410)

<400> SEQUENCE: 1
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtg | ctg | agc | cag | gtg | cag | ctg | gtg | cag | tct | ggc | gcc | gaa | gtg | aag | aaa | 96 |
|---|---|---|---|---|---|---|---|---|---|---|---|---|---|---|---|---|
| Val | Leu | Ser | Gln | Val | Gln | Leu | Val | Gln | Ser | Gly | Ala | Glu | Val | Lys | Lys | |
| | | | 20 | | | | | 25 | | | | | 30 | | | |

| cca | ggc | gcc | agc | gtg | aag | gtg | tcc | tgc | aag | gcc | agc | ggc | tac | acc | ttt | 144 |
|---|---|---|---|---|---|---|---|---|---|---|---|---|---|---|---|---|
| Pro | Gly | Ala | Ser | Val | Lys | Val | Ser | Cys | Lys | Ala | Ser | Gly | Tyr | Thr | Phe | |
| | | 35 | | | | | 40 | | | | | 45 | | | | |

| acc | acc | gcc | ggc | atg | cag | tgg | gtg | cgc | cag | gct | cct | gga | cag | ggc | ctg | 192 |
|---|---|---|---|---|---|---|---|---|---|---|---|---|---|---|---|---|
| Thr | Thr | Ala | Gly | Met | Gln | Trp | Val | Arg | Gln | Ala | Pro | Gly | Gln | Gly | Leu | |
| | 50 | | | | | 55 | | | | | 60 | | | | | |

| gaa | tgg | atg | ggc | tgg | atc | aac | acc | cac | agc | ggc | gtg | ccc | aaa | tac | gcc | 240 |
|---|---|---|---|---|---|---|---|---|---|---|---|---|---|---|---|---|
| Glu | Trp | Met | Gly | Trp | Ile | Asn | Thr | His | Ser | Gly | Val | Pro | Lys | Tyr | Ala | |
| 65 | | | | 70 | | | | | 75 | | | | | 80 | | |

| gag | gac | ttc | aag | ggc | aga | gtg | acc | atc | agc | gcc | gac | acc | agc | acc | tcc | 288 |
|---|---|---|---|---|---|---|---|---|---|---|---|---|---|---|---|---|
| Glu | Asp | Phe | Lys | Gly | Arg | Val | Thr | Ile | Ser | Ala | Asp | Thr | Ser | Thr | Ser | |
| | | | | 85 | | | | | 90 | | | | | 95 | | |

| aca | gcc | tac | ctg | cag | ctg | agc | agc | ctg | aag | tcc | gag | gac | acc | gcc | gtg | 336 |
|---|---|---|---|---|---|---|---|---|---|---|---|---|---|---|---|---|
| Thr | Ala | Tyr | Leu | Gln | Leu | Ser | Ser | Leu | Lys | Ser | Glu | Asp | Thr | Ala | Val | |
| | | | 100 | | | | | 105 | | | | | 110 | | | |

| tac | tac | tgc | gcc | aga | agc | ggc | ttc | ggc | agc | agc | tac | tgg | tac | ttc | gac | 384 |
|---|---|---|---|---|---|---|---|---|---|---|---|---|---|---|---|---|
| Tyr | Tyr | Cys | Ala | Arg | Ser | Gly | Phe | Gly | Ser | Ser | Tyr | Trp | Tyr | Phe | Asp | |
| | | 115 | | | | | 120 | | | | | 125 | | | | |

| gtg | tgg | ggc | cag | ggc | acc | ctc | gtg | acc | gtc | agc | tca | gcc | tcc | acc | aag | 432 |
|---|---|---|---|---|---|---|---|---|---|---|---|---|---|---|---|---|
| Val | Trp | Gly | Gln | Gly | Thr | Leu | Val | Thr | Val | Ser | Ser | Ala | Ser | Thr | Lys | |
| | 130 | | | | | 135 | | | | | 140 | | | | | |

| ggc | cca | agc | gtc | ttc | ccc | ctg | gca | ccc | tcc | tcc | aag | agc | acc | tct | ggc | 480 |
|---|---|---|---|---|---|---|---|---|---|---|---|---|---|---|---|---|
| Gly | Pro | Ser | Val | Phe | Pro | Leu | Ala | Pro | Ser | Ser | Lys | Ser | Thr | Ser | Gly | |
| 145 | | | | 150 | | | | | 155 | | | | | 160 | | |

| ggc | aca | gcc | gcc | ctg | ggc | tgc | ctg | gtc | aag | gac | tac | ttc | ccc | gaa | ccc | 528 |
|---|---|---|---|---|---|---|---|---|---|---|---|---|---|---|---|---|
| Gly | Thr | Ala | Ala | Leu | Gly | Cys | Leu | Val | Lys | Asp | Tyr | Phe | Pro | Glu | Pro | |
| | | | | 165 | | | | | 170 | | | | | 175 | | |

| gtg | acc | gtg | agc | tgg | aac | tca | ggc | gcc | ctg | acc | agc | ggc | gtg | cac | acc | 576 |
|---|---|---|---|---|---|---|---|---|---|---|---|---|---|---|---|---|
| Val | Thr | Val | Ser | Trp | Asn | Ser | Gly | Ala | Leu | Thr | Ser | Gly | Val | His | Thr | |
| | | | 180 | | | | | 185 | | | | | 190 | | | |

| ttc | ccc | gct | gtc | ctg | cag | tcc | tca | gga | ctc | tac | tcc | ctc | agc | agc | gtg | 624 |
|---|---|---|---|---|---|---|---|---|---|---|---|---|---|---|---|---|
| Phe | Pro | Ala | Val | Leu | Gln | Ser | Ser | Gly | Leu | Tyr | Ser | Leu | Ser | Ser | Val | |
| | | 195 | | | | | 200 | | | | | 205 | | | | |

| gtg | acc | gtg | ccc | tcc | agc | agc | ttg | ggc | acc | cag | acc | tac | atc | tgc | aac | 672 |
|---|---|---|---|---|---|---|---|---|---|---|---|---|---|---|---|---|
| Val | Thr | Val | Pro | Ser | Ser | Ser | Leu | Gly | Thr | Gln | Thr | Tyr | Ile | Cys | Asn | |
| | 210 | | | | | 215 | | | | | 220 | | | | | |

| gtg | aat | cac | aag | ccc | agc | aac | acc | aag | gtg | gac | aag | aga | gtt | gag | ccc | 720 |
|---|---|---|---|---|---|---|---|---|---|---|---|---|---|---|---|---|
| Val | Asn | His | Lys | Pro | Ser | Asn | Thr | Lys | Val | Asp | Lys | Arg | Val | Glu | Pro | |

```
aaa tct tgt gac aaa act cac aca tgc cca ccc tgc cca gca cct gaa      768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
    450                 455                 460 tcc ctg tct ccc ggc aaa                                             1410
Ser Leu Ser Pro Gly Lys
465                 470
```

<210> SEQ ID NO 2
<211> LENGTH: 470
<212> TYPE: PRT
<213> ORGANISM: Artificial Sequence
<220> FEATURE:
<223> OTHER INFORMATION: Synthetic Construct

<400> SEQUENCE: 2

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

```
                35                  40                  45
Thr Thr Ala Gly Met Gln Trp Val Arg Gln Ala Pro Gly Gln Gly Leu
         50                  55                  60

Glu Trp Met Gly Trp Ile Asn Thr His Ser Gly Val Pro Lys Tyr Ala
 65                  70                  75                  80

Glu Asp Phe Lys Gly Arg Val Thr Ile Ser Ala Asp Thr Ser Thr Ser
                 85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460
```

Ser Leu Ser Pro Gly Lys
465                 470

<210> SEQ ID NO 3
<211> LENGTH: 702
<212> TYPE: DNA
<213> ORGANISM: Artificial Sequence
<220> FEATURE:
<223> OTHER INFORMATION: hTINA1-L1
<220> FEATURE:
<221> NAME/KEY: CDS
<222> LOCATION: (1)..(702)

<400> SEQUENCE: 3

| | | | | | | | | | | | | | | | | |
|---|---|---|---|---|---|---|---|---|---|---|---|---|---|---|---|---|
| atg | gtg | ctg | cag | acc | cag | gtg | ttc | atc | tcc | ctg | ctg | ctg | tgg | atc | tcc | 48 |
| Met | Val | Leu | Gln | Thr | Gln | Val | Phe | Ile | Ser | Leu | Leu | Leu | Trp | Ile | Ser | |
| 1 | | | | 5 | | | | | 10 | | | | | 15 | | |
| ggc | gcg | tac | ggc | gac | atc | cag | atg | acc | cag | agc | cct | agc | agc | ctg | agc | 96 |
| Gly | Ala | Tyr | Gly | Asp | Ile | Gln | Met | Thr | Gln | Ser | Pro | Ser | Ser | Leu | Ser | |
| | | | 20 | | | | | 25 | | | | | 30 | | | |
| gcc | agc | gtg | ggc | gac | aga | gtg | acc | atc | aca | tgc | aag | gcc | agc | cag | gac | 144 |
| Ala | Ser | Val | Gly | Asp | Arg | Val | Thr | Ile | Thr | Cys | Lys | Ala | Ser | Gln | Asp | |
| | | 35 | | | | | 40 | | | | | 45 | | | | |
| gtg | tcc | aca | gcc | gtg | gcc | tgg | tat | cag | cag | aag | cct | ggc | aag | gcc | ccc | 192 |
| Val | Ser | Thr | Ala | Val | Ala | Trp | Tyr | Gln | Gln | Lys | Pro | Gly | Lys | Ala | Pro | |
| 50 | | | | | 55 | | | | | 60 | | | | | | |
| aag | ctg | ctg | atc | tac | agc | gcc | agc | tac | cgg | tac | acc | ggc | gtg | ccc | agc | 240 |
| Lys | Leu | Leu | Ile | Tyr | Ser | Ala | Ser | Tyr | Arg | Tyr | Thr | Gly | Val | Pro | Ser | |
| 65 | | | | | 70 | | | | | 75 | | | | | 80 | |
| aga | ttt | tct | ggc | agc | ggc | tcc | ggc | acc | gac | ttc | acc | ctg | aca | atc | agc | 288 |
| Arg | Phe | Ser | Gly | Ser | Gly | Ser | Gly | Thr | Asp | Phe | Thr | Leu | Thr | Ile | Ser | |
| | | | | 85 | | | | | 90 | | | | | 95 | | |
| agc | ctg | cag | ccc | gag | gac | ttc | gcc | gtg | tac | tac | tgc | cag | cag | cac | tac | 336 |
| Ser | Leu | Gln | Pro | Glu | Asp | Phe | Ala | Val | Tyr | Tyr | Cys | Gln | Gln | His | Tyr | |
| | | | 100 | | | | | 105 | | | | | 110 | | | |
| atc | acc | ccc | ctg | acc | ttt | ggc | cag | ggc | acc | aag | ctg | gaa | atc | aag | cgt | 384 |
| Ile | Thr | Pro | Leu | Thr | Phe | Gly | Gln | Gly | Thr | Lys | Leu | Glu | Ile | Lys | Arg | |
| | | 115 | | | | | 120 | | | | | 125 | | | | |
| acg | gtg | gcc | gcc | ccc | tcc | gtg | ttc | atc | ttc | ccc | ccc | tcc | gac | gag | cag | 432 |
| Thr | Val | Ala | Ala | Pro | Ser | Val | Phe | Ile | Phe | Pro | Pro | Ser | Asp | Glu | Gln | |
| | 130 | | | | | 135 | | | | | 140 | | | | | |
| ctg | aag | tcc | ggc | acc | gcc | tcc | gtg | gtg | tgc | ctg | ctg | aat | aac | ttc | tac | 480 |
| Leu | Lys | Ser | Gly | Thr | Ala | Ser | Val | Val | Cys | Leu | Leu | Asn | Asn | Phe | Tyr | |
| 145 | | | | | 150 | | | | | 155 | | | | | 160 | |
| ccc | aga | gag | gcc | aag | gtg | cag | tgg | aag | gtg | gac | aac | gcc | ctg | cag | tcc | 528 |
| Pro | Arg | Glu | Ala | Lys | Val | Gln | Trp | Lys | Val | Asp | Asn | Ala | Leu | Gln | Ser | |
| | | | | 165 | | | | | 170 | | | | | 175 | | |
| ggg | aac | tcc | cag | gag | agc | gtg | acc | gag | cag | gac | agc | aag | gac | agc | acc | 576 |
| Gly | Asn | Ser | Gln | Glu | Ser | Val | Thr | Glu | Gln | Asp | Ser | Lys | Asp | Ser | Thr | |
| | | | 180 | | | | | 185 | | | | | 190 | | | |
| tac | agc | ctg | agc | agc | acc | ctg | acc | ctg | agc | aaa | gcc | gac | tac | gag | aag | 624 |
| Tyr | Ser | Leu | Ser | Ser | Thr | Leu | Thr | Leu | Ser | Lys | Ala | Asp | Tyr | Glu | Lys | |
| | | 195 | | | | | 200 | | | | | 205 | | | | |
| cac | aag | gtg | tac | gcc | tgc | gag | gtg | acc | cac | cag | ggc | ctg | agc | tcc | ccc | 672 |
| His | Lys | Val | Tyr | Ala | Cys | Glu | Val | Thr | His | Gln | Gly | Leu | Ser | Ser | Pro | |
| | 210 | | | | | 215 | | | | | 220 | | | | | |
| gtc | acc | aag | agc | ttc | aac | agg | ggg | gag | tgt | | | | | | | 702 |
| Val | Thr | Lys | Ser | Phe | Asn | Arg | Gly | Glu | Cys | | | | | | | |
| 225 | | | | | 230 | | | | | | | | | | | |

<210> SEQ ID NO 4

<211> LENGTH: 234
<212> TYPE: PRT
<213> ORGANISM: Artificial Sequence
<220> FEATURE:
<223> OTHER INFORMATION: Synthetic Construct

<400> SEQUENCE: 4

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 5
<211> LENGTH: 5
<212> TYPE: PRT
<213> ORGANISM: Mus musculus

<400> SEQUENCE: 5

```
Thr Ala Gly Met Gln
1               5
```

<210> SEQ ID NO 6
<211> LENGTH: 17
<212> TYPE: PRT
<213> ORGANISM: Mus musculus

<400> SEQUENCE: 6

```
Trp Ile Asn Thr His Ser Gly Val Pro Lys Tyr Ala Glu Asp Phe Lys
1               5                   10                  15

Gly
```

<210> SEQ ID NO 7

```
<211> LENGTH: 12
<212> TYPE: PRT
<213> ORGANISM: Mus musculus

<400> SEQUENCE: 7

Ser Gly Phe Gly Ser Ser Tyr Trp Tyr Phe Asp Val
1               5                   10

<210> SEQ ID NO 8
<211> LENGTH: 11
<212> TYPE: PRT
<213> ORGANISM: Mus musculus

<400> SEQUENCE: 8

Lys Ala Ser Gln Asp Val Ser Thr Ala Val Ala
1               5                   10

<210> SEQ ID NO 9
<211> LENGTH: 7
<212> TYPE: PRT
<213> ORGANISM: Mus musculus

<400> SEQUENCE: 9

Ser Ala Ser Tyr Arg Tyr Thr
1               5

<210> SEQ ID NO 10
<211> LENGTH: 9
<212> TYPE: PRT
<213> ORGANISM: Mus musculus

<400> SEQUENCE: 10

Gln Gln His Tyr Ile Thr Pro Leu Thr
1               5

<210> SEQ ID NO 11
<211> LENGTH: 1395
<212> TYPE: DNA
<213> ORGANISM: Artificial Sequence
<220> FEATURE:
<223> OTHER INFORMATION: hM23-H1
<220> FEATURE:
<221> NAME/KEY: CDS
<222> LOCATION: (1)..(1395)

<400> SEQUENCE: 11
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtg | ctg | agc | cag | gtg | cag | ctg | gtg | cag | tct | ggc | gcc | gaa | gtg | aag | aaa | 96 |
| Val | Leu | Ser | Gln | Val | Gln | Leu | Val | Gln | Ser | Gly | Ala | Glu | Val | Lys | Lys | |
| | | | 20 | | | | | 25 | | | | | 30 | | | |
| cca | ggc | gcc | agc | gtg | aag | gtg | tcc | tgc | aag | gcc | agc | ggc | tac | gcc | ttc | 144 |
| Pro | Gly | Ala | Ser | Val | Lys | Val | Ser | Cys | Lys | Ala | Ser | Gly | Tyr | Ala | Phe | |
| | | 35 | | | | | 40 | | | | | 45 | | | | |
| agc | aac | tac | ctg | atc | gag | tgg | gtg | cgc | cag | gcc | cct | gga | cag | gga | ctg | 192 |
| Ser | Asn | Tyr | Leu | Ile | Glu | Trp | Val | Arg | Gln | Ala | Pro | Gly | Gln | Gly | Leu | |
| | 50 | | | | | 55 | | | | | 60 | | | | | |
| gaa | tgg | atg | ggc | gtg | atc | aac | cct | ggc | agc | ggc | gtg | acc | aac | tac | aac | 240 |
| Glu | Trp | Met | Gly | Val | Ile | Asn | Pro | Gly | Ser | Gly | Val | Thr | Asn | Tyr | Asn | |
| 65 | | | | | 70 | | | | | 75 | | | | | 80 | |
| gag | aag | ttc | aag | ggc | aga | gtg | acc | atc | acc | gcc | gac | acc | agc | acc | tcc | 288 |
| Glu | Lys | Phe | Lys | Gly | Arg | Val | Thr | Ile | Thr | Ala | Asp | Thr | Ser | Thr | Ser | |
| | | | | 85 | | | | | 90 | | | | | 95 | | |

| | | |
|---|---|---|
| acc gcc tac atg gaa ctg agc agc ctg cgg agc gag gac acc gcc gtg<br>Thr Ala Tyr Met Glu Leu Ser Ser Leu Arg Ser Glu Asp Thr Ala Val<br>100 105 110 | | 336 |
| tac tat tgt gcc aga gcc gag gct tgg ttt gcc tac tgg ggc cag gga<br>Tyr Tyr Cys Ala Arg Ala Glu Ala Trp Phe Ala Tyr Trp Gly Gln Gly<br>115 120 125 | | 384 |
| acc ctc gtg acc gtc agc tca gcc tcc acc aag ggc cca agc gtc ttc<br>Thr Leu Val Thr Val Ser Ser Ala Ser Thr Lys Gly Pro Ser Val Phe<br>130 135 140 | | 432 |
| ccc ctg gca ccc tcc tcc aag agc acc tct ggc ggc aca gcc gcc ctg<br>Pro Leu Ala Pro Ser Ser Lys Ser Thr Ser Gly Gly Thr Ala Ala Leu<br>145 150 155 160 | | 480 |
| ggc tgc ctg gtc aag gac tac ttc ccc gaa ccc gtg acc gtg agc tgg<br>Gly Cys Leu Val Lys Asp Tyr Phe Pro Glu Pro Val Thr Val Ser Trp<br>165 170 175 | | 528 |
| aac tca ggc gcc ctg acc agc ggc gtg cac acc ttc ccc gct gtc ctg<br>Asn Ser Gly Ala Leu Thr Ser Gly Val His Thr Phe Pro Ala Val Leu<br>180 185 190 | | 576 |
| cag tcc tca gga ctc tac tcc ctc agc agc gtg gtg acc gtg ccc tcc<br>Gln Ser Ser Gly Leu Tyr Ser Leu Ser Ser Val Val Thr Val Pro Ser<br>195 200 205 | | 624 |
| agc agc ttg ggc acc cag acc tac atc tgc aac gtg aat cac aag ccc<br>Ser Ser Leu Gly Thr Gln Thr Tyr Ile Cys Asn Val Asn His Lys Pro<br>210 215 220 | | 672 |
| agc aac acc aag gtg gac aag aga gtt gag ccc aaa tct tgt gac aaa<br>Ser Asn Thr Lys Val Asp Lys Arg Val Glu Pro Lys Ser Cys Asp Lys<br>225 230 235 240 | | 720 |
| act cac aca tgc cca ccc tgc cca gca cct gaa ctc ctg ggg gga ccc<br>Thr His Thr Cys Pro Pro Cys Pro Ala Pro Glu Leu Leu Gly Gly Pro<br>245 250 255 | | 768 |
| tca gtc ttc ctc ttc ccc cca aaa ccc aag gac acc ctc atg atc tcc<br>Ser Val Phe Leu Phe Pro Pro Lys Pro Lys Asp Thr Leu Met Ile Ser<br>260 265 270 | | 816 |
| cgg acc cct gag gtc aca tgc gtg gtg gtg gac gtg agc cac gaa gac<br>Arg Thr Pro Glu Val Thr Cys Val Val Val Asp Val Ser His Glu Asp<br>275 280 285 | | 864 |
| cct gag gtc aag ttc aac tgg tac gtg gac ggc gtg gag gtg cat aat<br>Pro Glu Val Lys Phe Asn Trp Tyr Val Asp Gly Val Glu Val His Asn<br>290 295 300 | | 912 |
| gcc aag aca aag ccc cgg gag gag cag tac aac agc acg tac cgg gtg<br>Ala Lys Thr Lys Pro Arg Glu Glu Gln Tyr Asn Ser Thr Tyr Arg Val<br>305 310 315 320 | | 960 |
| gtc agc gtc ctc acc gtc ctg cac cag gac tgg ctg aat ggc aag gag<br>Val Ser Val Leu Thr Val Leu His Gln Asp Trp Leu Asn Gly Lys Glu<br>325 330 335 | | 1008 |
| tac aag tgc aag gtc tcc aac aaa gcc ctc cca gcc ccc atc gag aaa<br>Tyr Lys Cys Lys Val Ser Asn Lys Ala Leu Pro Ala Pro Ile Glu Lys<br>340 345 350 | | 1056 |
| acc atc tcc aaa gcc aaa ggc cag ccc cgg gaa cca cag gtg tac acc<br>Thr Ile Ser Lys Ala Lys Gly Gln Pro Arg Glu Pro Gln Val Tyr Thr<br>355 360 365 | | 1104 |
| ctg ccc cca tcc cgg gag gag atg acc aag aac cag gtc agc ctg acc<br>Leu Pro Pro Ser Arg Glu Glu Met Thr Lys Asn Gln Val Ser Leu Thr<br>370 375 380 | | 1152 |
| tgc ctg gtc aaa ggc ttc tat ccc agc gac atc gcc gtg gag tgg gag<br>Cys Leu Val Lys Gly Phe Tyr Pro Ser Asp Ile Ala Val Glu Trp Glu<br>385 390 395 400 | | 1200 |
| agc aat ggc cag ccc gag aac aac tac aag acc acc cct ccc gtg ctg<br>Ser Asn Gly Gln Pro Glu Asn Asn Tyr Lys Thr Thr Pro Pro Val Leu<br>405 410 415 | | 1248 |

```
gac tcc gac ggc tcc ttc ttc ctc tac agc aag ctc acc gtg gac aag     1296
Asp Ser Asp Gly Ser Phe Phe Leu Tyr Ser Lys Leu Thr Val Asp Lys
            420                 425                 430 agc agg tgg cag cag ggc aac gtc ttc tca tgc tcc gtg atg cat gag     1344
Ser Arg Trp Gln Gln Gly Asn Val Phe Ser Cys Ser Val Met His Glu
        435                 440                 445 gct ctg cac aac cac tac acc cag aag agc ctc tcc ctg tct ccc ggc     1392
Ala Leu His Asn His Tyr Thr Gln Lys Ser Leu Ser Leu Ser Pro Gly
    450                 455                 460 aaa                                                                 1395
Lys
465

<210> SEQ ID NO 12
<211> LENGTH: 465
<212> TYPE: PRT
<213> ORGANISM: Artificial Sequence
<220> FEATURE:
<223> OTHER INFORMATION: Synthetic Construct

<400> SEQUENCE: 12

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Ser Asn Tyr Leu Ile Glu Trp Val Arg Gln Ala Pro Gly Gln Gly Leu
    50                  55                  60

Glu Trp Met Gly Val Ile Asn Pro Gly Ser Gly Val Thr Asn Tyr Asn
65                  70                  75                  80

Glu Lys Phe Lys Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ala Glu Ala Trp Phe Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
```

```
                275                 280                 285
Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 13
<211> LENGTH: 720
<212> TYPE: DNA
<213> ORGANISM: Artificial Sequence
<220> FEATURE:
<223> OTHER INFORMATION: hM23-L1
<220> FEATURE:
<221> NAME/KEY: CDS
<222> LOCATION: (1)..(720)

<400> SEQUENCE: 13 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc gtg atg acc cag agc cct gac agc ctg gcc      96
Gly Ala Tyr Gly Asp Ile Val Met Thr Gln Ser Pro Asp Ser Leu Ala
            20                  25                  30 gtg tct ctg gga gag aga gcc acc atc aac tgc aag agc agc cag agc     144
Val Ser Leu Gly Glu Arg Ala Thr Ile Asn Cys Lys Ser Ser Gln Ser
        35                  40                  45 ctg ctg tac tcc agc aac cag aag aac tac ctg gcc tgg tat cag cag     192
Leu Leu Tyr Ser Ser Asn Gln Lys Asn Tyr Leu Ala Trp Tyr Gln Gln
    50                  55                  60 aag ccc ggc cag cct ccc aag ctg ctg atc tac tgg gcc agc acc aga     240
Lys Pro Gly Gln Pro Pro Lys Leu Leu Ile Tyr Trp Ala Ser Thr Arg
65                  70                  75                  80 gaa agc ggc gtg ccc gat aga ttc agc ggc agc gga agc ggc acc gac     288
Glu Ser Gly Val Pro Asp Arg Phe Ser Gly Ser Gly Ser Gly Thr Asp
                85                  90                  95 ttc acc ctg aca atc agc tcc ctg cag gcc gag gac gtg gcc gtg tac     336
Phe Thr Leu Thr Ile Ser Ser Leu Gln Ala Glu Asp Val Ala Val Tyr
            100                 105                 110
```

| | | | | | | | | | | | | | | | |
|---|---|---|---|---|---|---|---|---|---|---|---|---|---|---|---|
| tac | tgc | cag | cgg | tac | tac | ggc | tac | ccc | tgg | acc | ttt | ggc | cag | ggc | acc | 384 |
| Tyr | Cys | Gln | Arg | Tyr | Tyr | Gly | Tyr | Pro | Trp | Thr | Phe | Gly | Gln | Gly | Thr | |
| | | 115 | | | | | 120 | | | | | 125 | | | | |

```
tac tgc cag cgg tac tac ggc tac ccc tgg acc ttt ggc cag ggc acc    384
Tyr Cys Gln Arg Tyr Tyr Gly Tyr Pro Trp Thr Phe Gly Gln Gly Thr
        115                 120                 125 aag gtg gaa atc aag cgt acg gtg gcc gcc ccc tcc gtg ttc atc ttc    432
Lys Val Glu Ile Lys Arg Thr Val Ala Ala Pro Ser Val Phe Ile Phe
130                 135                 140 ccc ccc tcc gac gag cag ctg aag tcc ggc acc gcc tcc gtg gtg tgc    480
Pro Pro Ser Asp Glu Gln Leu Lys Ser Gly Thr Ala Ser Val Val Cys
145                 150                 155                 160 ctg ctg aat aac ttc tac ccc aga gag gcc aag gtg cag tgg aag gtg    528
Leu Leu Asn Asn Phe Tyr Pro Arg Glu Ala Lys Val Gln Trp Lys Val
                165                 170                 175 gac aac gcc ctg cag tcc ggg aac tcc cag gag agc gtg acc gag cag    576
Asp Asn Ala Leu Gln Ser Gly Asn Ser Gln Glu Ser Val Thr Glu Gln
                180                 185                 190 gac agc aag gac agc acc tac agc ctg agc agc acc ctg acc ctg agc    624
Asp Ser Lys Asp Ser Thr Tyr Ser Leu Ser Ser Thr Leu Thr Leu Ser
            195                 200                 205 aaa gcc gac tac gag aag cac aag gtg tac gcc tgc gag gtg acc cac    672
Lys Ala Asp Tyr Glu Lys His Lys Val Tyr Ala Cys Glu Val Thr His
210                 215                 220 cag ggc ctg agc tcc ccc gtc acc aag agc ttc aac agg ggg gag tgt    720
Gln Gly Leu Ser Ser Pro Val Thr Lys Ser Phe Asn Arg Gly Glu Cys
225                 230                 235                 240
```

<210> SEQ ID NO 14
<211> LENGTH: 240
<212> TYPE: PRT
<213> ORGANISM: Artificial Sequence
<220> FEATURE:
<223> OTHER INFORMATION: Synthetic Construct

<400> SEQUENCE: 14

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Arg Tyr Tyr Gly Tyr Pro Trp Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
```

```
            195                 200                 205
Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 15
<211> LENGTH: 5
<212> TYPE: PRT
<213> ORGANISM: Mus musculus

<400> SEQUENCE: 15

Asn Tyr Leu Ile Glu
1               5

<210> SEQ ID NO 16
<211> LENGTH: 17
<212> TYPE: PRT
<213> ORGANISM: Mus musculus

<400> SEQUENCE: 16

Val Ile Asn Pro Gly Ser Gly Val Thr Asn Tyr Asn Glu Lys Phe Lys
1               5                   10                  15

Gly

<210> SEQ ID NO 17
<211> LENGTH: 7
<212> TYPE: PRT
<213> ORGANISM: Mus musculus

<400> SEQUENCE: 17

Ala Glu Ala Trp Phe Ala Tyr
1               5

<210> SEQ ID NO 18
<211> LENGTH: 17
<212> TYPE: PRT
<213> ORGANISM: Mus musculus

<400> SEQUENCE: 18

Lys Ser Ser Gln Ser Leu Leu Tyr Ser Asn Gln Lys Asn Tyr Leu
1               5                   10                  15

Ala

<210> SEQ ID NO 19
<211> LENGTH: 7
<212> TYPE: PRT
<213> ORGANISM: Mus musculus

<400> SEQUENCE: 19

Trp Ala Ser Thr Arg Glu Ser
1               5

<210> SEQ ID NO 20
<211> LENGTH: 9
<212> TYPE: PRT
<213> ORGANISM: Mus musculus

<400> SEQUENCE: 20

Gln Arg Tyr Tyr Gly Tyr Pro Trp Thr
1               5
```

-continued

<210> SEQ ID NO 21
<211> LENGTH: 22
<212> TYPE: DNA
<213> ORGANISM: Artificial Sequence
<220> FEATURE:
<223> OTHER INFORMATION: primer EG-Inf-F

<400> SEQUENCE: 21
agctcccaga tgggtgctga gc                                              22

<210> SEQ ID NO 22
<211> LENGTH: 22
<212> TYPE: DNA
<213> ORGANISM: Artificial Sequence
<220> FEATURE:
<223> OTHER INFORMATION: primer EG1-Inf-R

<400> SEQUENCE: 22
gggcccttgg tggaggctga gc                                              22

<210> SEQ ID NO 23
<211> LENGTH: 24
<212> TYPE: DNA
<213> ORGANISM: Artificial Sequence
<220> FEATURE:
<223> OTHER INFORMATION: primer CM-LKF

<400> SEQUENCE: 23
ctgtggatct ccggcgcgta cggc                                            24

<210> SEQ ID NO 24
<211> LENGTH: 21
<212> TYPE: DNA
<213> ORGANISM: Artificial Sequence
<220> FEATURE:
<223> OTHER INFORMATION: primer KCL-Inf-R

<400> SEQUENCE: 24 ggaggggggcg gccaccgtac g                                              21

<210> SEQ ID NO 25
<211> LENGTH: 471
<212> TYPE: PRT
<213> ORGANISM: Artificial Sequence
<220> FEATURE:
<223> OTHER INFORMATION: M30-H1

<400> SEQUENCE: 25

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Arg Gln Ala Pro Gly Gln Gly Leu
    50                  55                  60

Glu Trp Met Gly Tyr Ile Asn Pro Tyr Asn Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe

```
            115                 120                 125
Asp Tyr Trp Gly Gln Gly Thr Leu Val Thr Val Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 26
<211> LENGTH: 233
<212> TYPE: PRT
<213> ORGANISM: Artificial Sequence
<220> FEATURE:
<223> OTHER INFORMATION: M30-L4

<400> SEQUENCE: 26

Met Val Leu Gln Thr Gln Val Phe Ile Ser Leu Leu Leu Trp Ile Ser
```

```
1               5                   10                  15
Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
            50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230

<210> SEQ ID NO 27
<211> LENGTH: 5
<212> TYPE: PRT
<213> ORGANISM: Mus musculus

<400> SEQUENCE: 27

Asn Tyr Val Met His
1               5

<210> SEQ ID NO 28
<211> LENGTH: 17
<212> TYPE: PRT
<213> ORGANISM: Mus musculus

<400> SEQUENCE: 28

Tyr Ile Asn Pro Tyr Asn Asp Asp Val Lys Tyr Asn Glu Lys Phe Lys
1               5                   10                  15

Gly

<210> SEQ ID NO 29
<211> LENGTH: 13
<212> TYPE: PRT
<213> ORGANISM: Mus musculus

<400> SEQUENCE: 29

Trp Gly Tyr Tyr Gly Ser Pro Leu Tyr Tyr Phe Asp Tyr
1               5                   10
```

<210> SEQ ID NO 30
<211> LENGTH: 10
<212> TYPE: PRT
<213> ORGANISM: Mus musculus

<400> SEQUENCE: 30

Arg Ala Ser Ser Arg Leu Ile Tyr Met His
1               5                   10

<210> SEQ ID NO 31
<211> LENGTH: 7
<212> TYPE: PRT
<213> ORGANISM: Mus musculus

<400> SEQUENCE: 31

Ala Thr Ser Asn Leu Ala Ser
1               5

<210> SEQ ID NO 32
<211> LENGTH: 9
<212> TYPE: PRT
<213> ORGANISM: Mus musculus

<400> SEQUENCE: 32

Gln Gln Trp Asn Ser Asn Pro Pro Thr
1               5

<210> SEQ ID NO 33
<211> LENGTH: 450
<212> TYPE: PRT
<213> ORGANISM: Artificial Sequence
<220> FEATURE:
<223> OTHER INFORMATION: Heavy chain of Trastuzumab

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 34
<211> LENGTH: 214
<212> TYPE: PRT
<213> ORGANISM: Artificial Sequence
<220> FEATURE:
<223> OTHER INFORMATION: Light chain of Trastuzumab

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Phe Gly
1
```

UNITED STATES PATENT AND TRADEMARK OFFICE
CERTIFICATE OF CORRECTION

PATENT NO. : 11,173,213 B2
APPLICATION NO. : 15/579512
DATED : November 16, 2021
INVENTOR(S) : Shigeru Noguchi, Ken Sakurai and Daisuke Okajima It is certified that error appears in the above-identified patent and that said Letters Patent is hereby corrected as shown below:

In the Claims

Claim 26, Column 102, Lines 18-40:
Please replace with:
26. The production method according to claim 14, wherein the drug linker intermediate is

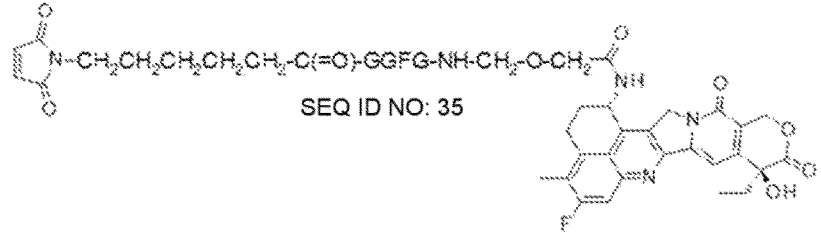

wherein -GGFG- (SEQ ID NO: 35) represents a tetrapeptide residue consisting of glycine-glycine-phenylalanine-glycine.

Signed and Sealed this
Twentieth Day of December, 2022

Katherine Kelly Vidal
Director of the United States Patent and Trademark Office